US008592394B2

(12) United States Patent
Ilan et al.

(10) Patent No.: US 8,592,394 B2
(45) Date of Patent: *Nov. 26, 2013

(54) SYNTHETIC DERIVATIVES BETA GLYCOLIPIDS AND COMPOSITIONS THEREOF FOR THE TREATMENT OF PATHOLOGIC DISORDERS

(75) Inventors: Yaron Ilan, Givat Massua (IL); Arie Dagan, Jerusalem (IL)

(73) Assignee: Enzo Therapeutics, Inc., Farmingdale, NY (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/587,752

(22) Filed: Oct. 13, 2009

(65) Prior Publication Data

US 2010/0221358 A1 Sep. 2, 2010

Related U.S. Application Data

(63) Continuation-in-part of application No. 12/586,100, filed on Sep. 17, 2009, which is a continuation-in-part of application No. 10/675,980, filed on Sep. 30, 2003.

(51) Int. Cl.
*A01N 43/04* (2006.01)
*A61K 31/70* (2006.01)
(52) U.S. Cl.
USPC ............. 514/62; 514/25; 514/866; 514/909
(58) Field of Classification Search
USPC ..................... 514/62, 25, 866, 909
See application file for complete search history.

(56) References Cited

U.S. PATENT DOCUMENTS

| 6,756,504 B2 * | 6/2004 | Dagan et al. ............... 554/52 |
| 7,897,580 B2 * | 3/2011 | Ilan ............................. 514/25 |
| 2007/0117778 A1 * | 5/2007 | Ilan ............................. 514/54 |
| 2009/0221516 A1 * | 9/2009 | Tashiro et al. ............... 514/25 |

FOREIGN PATENT DOCUMENTS

| WO | WO 01/79152 A1 * | 10/2001 | ............ C07C 215/68 |
| WO | WO03/027058 | 4/2003 | |
| WO | WO2005/032462 | 4/2005 | |
| WO | WO2007/060652 | 5/2007 | |
| WO | WO 2007/099999 A1 * | 9/2007 | ............. C07H 15/04 |

OTHER PUBLICATIONS

Hansen, B.C. (1999) The Metabolic Syndrome X. Annals New York Academy of Sciences, vol. 892, p. 1-24.*
Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"Immunodeficiency Disorders" from the Merck Manual Home Edition [online]. [Retrieved Mar. 18, 2011]. Retrieved from the Internet <http://www.merckmanuals.com/home/print/sec16/ch184/ch184a.html>.*
"Immune System" from KidsHealth [online]. [Retrieved Mar. 24, 2011]. Retrieved from the internet <http://kidshealth.org/teen/your_body/body_basics/immune.html> Published Jun. 18, 2007.*
Mackay, I.R., Rosen, F.S. (2001) Autoimmune Diseases, New England Journal of Medicine, vol. 345, No. 5, p. 340-350.*
"Neurological disorders" from health-cares.net [online], [retrieved Jan. 6, 2010]. Retrieved from the internet <http://neurology.health-cares.net/>, published online Feb. 7, 2005.*
"Degenerative nervous system diseases" from health-cares.net [online], [retrieved Jan. 6, 2010]. Retrieved from the internet <http://neurology.health-cares.net/degenerative-system.php>, published online Jun. 26, 2005.*
Merck Manual Home Edition, subject "Viral Infections" [online], [Retrieved on Oct. 16, 2008]. Retrieved from the internet <http://www.merck.com/mmhe/print/sec17/ch198/ch198a.html>.*
Todar, K. (2008) "Bacterial Resistance to Antibiotics" in Todar's Online Textbook of Bacteriology, [online], [Retrieved on Dec. 28, 2008]. Retrieved from the internet <http://www.textbookofbacteriology.net/resantimicrobial.html>, p. 1-4.*
Gatenby, R.A., Gawlinski, E.T. (2003) The Glycolytic Phenotype in Carcinogenesis and Tumor Invasion: Insights through Mathematical Models. Cancer Research, vol. 63, p. 3847-3854.*
Hoffman, E.P. (2000) "Genetic Changes in Cancer: Second of Three Parts" [online], [Retrieved on Apr. 14, 2011]. Retrieved from the internet <http://www.candlelighters.org/Research/genetics2.aspx>.*
Rouhi, A.M. (2004) Metabolic Syndrome. Chemical & Engineering News, vol. 82, No. 47, p. 83-99.*
Holland, W.L. et al. (2007) Inhibition of Ceramide Synthesis Ameliorates Glucocorticoid-, Saturated-Fat-, and Obesity-Induced Insulin Resistance. Cell Metabolism, vol. 5, p. 167-179.*
Summers, S.A., Nelson, D.H. (2005) A Role for Sphingolipids in Producing the Common Features of Type 2 Diabetes, Metabolic Syndrome X, and Cushing's Syndrome. Diabetes, vol. 54, p. 591-602.*
Adar et al., Aggregation of red blood cells in patients with Gaucher disease, British Journal of Haematology 2006, 432-437, 134.
Adar et al., Increased red blood cell aggregation in patients with Gaucher disease is non-inflammatory, Clinical Hemorheology and Microcirculation 2008, 113-118, 40.
Ajuebor and Swain, Role of chemokines and chemokine receptors in the gastrointestinal tract, Immunology 2002, 137-143, 105.
Araki et al., Synthetic Glycolipid Ligands for Human iNKT Cells as Potential Therapeutic Agents for Immunotherapy, Current Medicinal Chemistry 2008, 2337-2345, 15.
Bendelac et al., The Biology of NKT Cells, Annu. Rev. Immunol. 2007, 297-336, 25.
Bezbradica et al., Distinct Roles of Dendritic Cells and B Cells in Va14Ja18 Natural T Cell Activation In Vivo, The Journal of Immunology 2005, 4696-4705, 174.
Biburger and Tiegs et al., Alpha-Galactosylceramide-Induced Liver Injury in Mice Is Mediated by TNF-alpha but Independent of Kupffer Cells, The Journal of Immunology 2005, 1540-1550, 175.

(Continued)

*Primary Examiner* — Scarlett Goon
(74) *Attorney, Agent, or Firm* — Anna D. DiGabriele Petti, Esq.

(57) ABSTRACT

The invention relates to novel synthetic derivatives of β-glycolipids and uses thereof as immunomodulators. More particularly, the invention relates to synthetic derivatives of β-glycolipids, specifically, the compounds of any one of Formula I, II III and IV or any mixture or combination thereof, and particularly the ALIB-97 (Formula II) derivative and uses thereof for the treatment of different pathologic disorders, particularly, immune-related hepatic disorders and pathologies associated with the metabolic syndrome.

15 Claims, 27 Drawing Sheets

(56) References Cited

OTHER PUBLICATIONS

Brigl and Brenner, CD1: Antigen Presentation and T Cell Function, Annu. Rev. Immunol. 2004, 817-890, 22.

Brutkiewicz et al., CD1d-Mediated Antigen Presentation to Natural Killer T (NKT) Cells, Critical Reviews in Immunology 2003, 403-419, 23(5&6).

Randy R. Brutkiewicz, CD1d Ligands: The Good, the Bad, and the Ugly, The Journal of Immunology 2006, 769-775, 177.

Chiu et al., Multiple defects in antigen presentation and T cell development by mice expressing cytoplasmic tail-truncated CD1d, Nature Immunology 2002, 55-60, 3(1).

Curat et al., From Blood Monocytes to Adipose Tissue—Resident Macrophages Induction of Diapedesis by Human Mature Adipocytes, Diabetes 2004,1285-1292, 53.

Dao et al., Development of CD1d-restricted NKT cells in the mouse thymus, Eur. J. Immunol. 2004, 3542-3552, 34.

Darnell et al., Jak-STAT Pathways and Transcriptional Activation in Response to IFNs and Other Extracellular Signaling Proteins, Science New Series 1994, 1415-1421, 264(5164).

Epstein and Yaccoby, The SCID-hu Myeloma Model, Methods in Molecular Medicine, 2005, 183-190, 113.

Exley and Koziel, To Be or Not to Be NKT: Natural Killer T Cells in the Liver, Hepatology 2004,1033-1040, 40.

Fernandez-Real and Ricart, Insulin Resistance and Chronic Cardiovascular Inflammatory Syndrome, Endocrine Reviews 2003, 278-301, 24(3).

Godfrey and Kronenberg, Going both ways: immune regulation via CD1d-dependent NKT cells, J. Clin. Invest. 2004,1379-1388,114.

Godfrey et al. The Elusive NKT Cell Antigen—Is the Search Over?, Science 2004, 1687-1689, 306.

Goker-Alpan and Sidransky, Risky business: Gaucher disease and multiple myeloma, Blood 2005, 4546-4547, 105.

Halder et al., Type II NKT cell—mediated anergy induction in type I NKT cells prevents inflammatory liver disease, J. Clin. Invest 2007, 2302-2312, 117(8).

Hammond and Kronenberg, Natural killer T cells: natural or unnatural regulators of autoimmunity?, Current Opinion in Immunology 2003, 683-689, 15.

Hammond and Godfrey, NKT cells: Potential targets for autoimmune disease therapy?, Tissue Antigens 2002, 353-363, 59.

Hansen and Schofield, Regulation of immunity and pathogenesis in infectious diseases by CD1d-restricted NKT cells, International Journal for Parasitology 2004, 15-25, 34.

Haratz et al., Autoimmune hemolytic anemia in Gaucher's disease, Journal of Molecular Medicine 1990 94-95, 68(2).

Gokhan Hotamisligil, Inflammation and metabolic disorders, Nature 2006, 860-867, 444.

Hotamisligil et al., Adipose Expression of Tumor Necrosis Factor-a: Direct Role in Obesity-Linked Insulin Resistance, Science 1993, 87-91, 259(5091).

Huber et al., Role of CD1d in Coxsackievirus B3-Induced Myocarditis, The Journal of Immunology 2003, 3147-3153, 170.

Ilan et al., Alleviation of Acute and Chronic Graft-Versus-Host Disease in a Murine Model Is Associated with Glucocerebroside-Enhanced Natural Killer T Lymphocyte Plasticity, Transplantation 2007, 458-467, 83(4), abstract only.

Jaruga et al., Crucial Role of IL-4/STAT6 in T Cell-Mediated Hepatitis: Up-Regulating Eotaxins and IL-5 and Recruiting Leukocytes, The Journal of Immunology, 2003, 3233-3244, 171.

Kaneko et al., Augmentation of Valpha14 NKT Cell—mediated Cytotoxicity by Interleukin 4 in an Autocrine Mechanism Resulting in the Development of Concanavalin A—induced Hepatitis, J. Exp. Med. 2000,105-114, 191(1).

Kaneto et al., Oxidative Stress and the JNK Pathway in Diabetes, Current Diabetes Reviews 2005, 65-72, 1.

Kawano et al., CD1d-Restricted and TCR-Mediated Activation of Valpha14 NKT Cells by Glycosylceramides, Science 1997, 1626-1629, 278.

Kershaw and Flier, Adipose Tissue as an Endocrine Organ, J Clin Endocrinol Metab 2004, 2548-2556, 89.

Kodama and Brenner, c-Jun N-Terminal Kinase Signaling in the Pathogenesis of Nonalcoholic Fatty Liver Disease: Multiple Roles in Multiple Steps, Hepatology 2009, 6-8, 49.

Kronenberg, Mitchell,Toward an Understanding of NKT Cell Biology: Progress and Paradoxes, Annu. Rev. Immunol. 2005, 877-900, 26.

Lalazar et al., beta-Glycosphingolipids-mediated lipid raft alteration is associated with redistribution of NKT cells and increased intrahepatic CD8+ T lymphocyte trapping, J. Lipid Res. 2008,1884-1893, 49.

Lalazar et al., Glycolipids as Immune Modulatory Tools, Mini-Reviews in Medicinal Chemistry 2006,1249-1253, 6.

Lalazar et al., Modulation of intracellular machinery by beta-glycolipids is associated with alteration of NKT lipid rafts and amelioration of concanavalin-induced hepatitis, Molecular Immunology 2008, 3517-3525, 45.

Landgren et al., Risk of malignant disease among 1525 adult male US veterans with Gaucher disease, Arch Intern Med 2007, 1189-1194, 167.

Liu and Rondinone, JNK: Bridging the insulin signaling and inflammatory pathway, Current Opinion in Investigational Drugs 2005, 979-987, 6(10).

Livovsky et al., Administration of beta-glycolipids overcomes an unfavorable nutritional dependent host milieu: a role for a soy-free diet and natural ligands in intrahepatic CD8+ lymphocyte trapping and NKT cell redistribution, International Immunopharmacology 2008, 1298-1305, 8.

Malhi and Gores, Molecular Mechanisms of Lipotoxicity in Nonalcoholic Fatty Liver Disease, Semin Liver Dis 2008, 360-369, 28.

Margalit et al., Glucocerebroside treatment ameliorates ConA hepatitis by inhibition of NKT lymphocytes, Am J Physiol Gastrointest Liver Physiol 2005, G917-G925, 289.

Margalit et al., Glucocerebroside Ameliorates the Metabolic Syndrome in OB/OB Mice, JPET 2006, 105-110, 319 (1).

Matteoni et al., Nonalcoholic Fatty Liver Disease: A Spectrum of Clinical and Pathological Severity, Gastroenterology 1999, 1413-1419, 116.

Mayeux, Richard, Epidemiology of Neurodegeneration, Annu. Rev. Neurosci. 2003, 81-104, 26.

Mitchell et al., Chemical Shift Phase-Difference and Suppression Magnetic Resonance Imaging Techniques in Animals, Phantoms, and Humans, Invest. Radiol. 1991, 1041-1052, 26.

Mitsui et al., Mutations for Gaucher Disease Confer High Susceptibility to Parkinson Disease, Arch Neurol. 2009, 571-576, 66(5).

Miyagi et al., Concanavalin A Injection Activates Intrahepatic Innate Immune Cells to Provoke an Antitumor Effect in Murine Liver, Hepatology 2004, 1190-1196, 40.

Miyake and Yamamura, Therapeutic Potential of Glycolipid Ligands for Natural Killer (NK) T Cells in the Suppression of Autoimmune Diseases, Current Drug Targets—Immune, Endocrine & Metabolic Disorders, 2005, 315-322, 5.

Miyake and Yamamura, NKT Cells and Autoimmune Diseases: Unraveling the Complexity, Curr. Top. Microbiol. Immunol. 2007, 251-265, 314.

Mizrahi et al., beta-G lycoglycosphingolipid-induced augmentation of the anti-HBV immune response is associated with altered CD8 and NKT lymphocyte distribution: A novel adjuvant for HBV vaccination, Vaccine 2008, 2589-2595, 26.

Namimoto et al., Adrenal Masses: Quantification of Fat Content with Double-Echo Chemical Shift In-Phase and Opposed-Phase FLASH MR Images for Differentiation of Adrenal Adenomas, Radiology 2001, 642-646, 218.

Nicoletti et al., Murine Concanavalin A-induced hepatitis is prevented by interleukin 12 (IL-12) antibody and exacerbated by exogenous IL-12 through an interferon-gamma-dependent mechanism, Hepatology 2000, 728-733, 32.

Nicoletti et al., Essential pathogenetic role for interferon (IFN-)gamma in concanavalin A-induced T cell-dependent hepatitis: Exacerbation by exogenous IFN-gamma and prevention by IFN-gamma receptor-immunoglobulin fusion protein, Cytokine 2000, 315-323, 12(4).

Oh et al., Role of type II NKT cells in the suppression of graft-versus-host disease, Crit. Rev. Immunol. 2008, 249-267, 28(3).

(56) References Cited

OTHER PUBLICATIONS

Oki et al., The clinical implication and molecular mechanism of preferential IL-4 production by modified glycolipid-stimulated NKT cells, J. Clin. Invest. 2004, 1631-1640, 113.

Onoe et al., Th1 or Th2 balance regulated by interaction between dendritic cells and NKT cells, Immunol Res 2007, 319-332, 38.

Ortaldo et al., Dissociation of NKT Stimulation, Cytokine Induction, and NK Activation In Vivo by the Use of Distinct TCR-Binding Ceramides, J Immunol 2004, 943-953, 172.

Osman et al., Activation of hepatic NKT cells and subsequent liver injury following administration of alpha-galactosylceramide, Eur. J. Immunol. 2000, 1919-1928, 30.

Porubsky et al., Normal development and function of invariant natural killer T cells in mice with isoglobotrihexosylceramide (iGb3) deficiency, PNAS 2007, 5977-5982, 104(14).

Sandberg and Ljunggren, Development and function of CD1d-restricted NKT cells: influence of sphingolipids, SAP and sex, Trends in Immunology 2005, 347-349, 26.

Selkoe, Dennis, Alzheimer's disease: Genes, proteins, and therapy, Physiol. Rev. 2001, 741-766, 81(2).

Shevach, Ethan, From vanilla to 28 flavors: Multiple varieties of T regulatory cells, Immunity 2006, 195-201, 25.

Singh et al., Differential Effects of JNK1 and JNK2 Inhibition on Murine Steatohepatitis and Insulin Resistance, Hepatology 2009, 87-96, 49.

Singh et al., Natural Killer T Cell Activation Protects Mice Against Experimental Autoimmune Encephalomyelitis, J. Exp. Med. 2001, 1801-1811, 194(12).

Skold and Behar, Role of CD1d-Restricted NKT Cells in Microbial Immunity, Infection and Immunity, 2003, 5447-5455, 71(10).

Smith et al., Traditional sampling with laboratory analysis and solid phase microextraction sampling with field gas chromatography/mass spectrometry by military industrial hygienists, AIHA Journal 2002, 284-292, 63.

Smyth et al., NKT cells—conductors of tumor immunity?, Curr. Opin. Immunology 2002, 165-171, 14.

Stanic et al., Another View of T Cell Antigen Recognition: Cooperative Engagement of Glycolipid Antigens by Va14Ja18 Natural TCR, The Journal of Immunology 2003, 171, 4539-4551, 171.

Stanic et al., Innate self recognition by an invariant, rearranged T-cell receptor and its immune consequences, Immunology 2003, 171-184, 109.

Takeda and Okumura, Human Cell 2001, 159-163, 14(3).

Takeda et al., Critical contribution of liver natural killer T cells to a murine model of hepatitis, PNAS 2000, 5498-5503, 97(10).

Taniguchi et al., The regulatory role of Valpha14 NKT cells in innate and acquired immune response, Annu. Rev. Immunol. 2003, 483-513, 21.

Tessmer et al., NKT cell immune responses to viral infection, Expert Opin. Ther. Targets 2009, 153-162, 13(2).

Tiegs, G., Cellular and Cytokine-Mediated Mechanisms of Inflammation and its Modulation in Immune-Mediated Liver Injury, Z Gastroenterol 2007, 63-70, 45.

Tomura et al., A Novel Function of Valpha14+CD4+NKT Cells: Stimulation of IL-12 Production by Antigen-Presenting Cells in the Innate Immune System, J Immunol 1999, 93-101, 163.

Torisu et al., Suppressor of Cytokine Signaling 1 Protects Mice Against Concanavalin A-Induced Hepatitis by Inhibiting Apoptosis, Hepatology 2008, 1644-1654, 47.

Trayhurn et al., Adipose Tissue and Adipokines—Energy Regulation from the Human Perspective, J. Nutr. 2006, 1935S-1939S, 136.

Trop et al., Liver associated lymphocytes expressing NK1.1 are essential for oral immune tolerance induction in a murine model, Hepatology 1999, 746-755, 29.

Tsuji, M., Glycolipids and phospholipids as natural CD1d-binding NKT cell ligands, Cell. Mol. Life Sci. 2006, 1889-1898, 63.

Tupin et al., The unique role of natural killer T cells in the response to microorganisms, Nature Rev. Microbiology 2007, 405-417, 5.

Uemura et al., Role of human non-invariant NKT lymphocytes in the maintenance of type 2 T helper environment during pregnancy, International Immunology, 2008, 405-412, 20(3).

Vanderkerken et al., The 5T2MM murine model of multiple myeloma, Methods in Mol. Med. 2005, 191-205, 113.

Luc Van Kaer, NKT cells: T lymphocytes with innate effector functions, Curr. Opin. in Immunology 2007, 354-364, 19.

Luc Van Kaer, α-Galactosylceramide therapy for autoimmune diseases: prospects and obstacles, Nature Revs Immunology 2005, 31-42, 5.

Weiner, Howard L., Oral tolerance: immune mechanisms and treatment of automimmune diseases, Rev. Immunology Today 1997, 335-343, 18(7).

Weisberg et al., Obesity is associated with macrophage accumulation in adipose tissue, J. Clin. Invest. 2003, 1796-1808, 112.

Wilson and Van Kaer, Natural Killer T Cells as Targets for Therapeutic Intervention in Autoimmune Diseases, Current Pharmaceutical Design 2003, 201-220, 9.

Xu et al., Chronic inflammation in fat plays a crucial role in the development of obesity-related insulin resistance, J. Clin. Invest. 2003, 1821-1830, 112.

Yamamura et al., NKT Cell-Stimulating Synthetic Glycolipids as Potential Therapeutics for Autoimmune Disease, Current Topics in Medicinal Chemistry 2004, 561-567, 4.

Yang et al., Role of Interferon-γ in GVHD and GVL, Cellular & Molecular Immunology 2005, 323-329, 2(5).

Yu et al., Production and characterization of monoclonal antibodies against complexes of the NKT cell ligand α-galactosylceramide bound to mouse CD1d, Journal of Immunological Methods 2007, 11-23, 323.

Yu et al., Modulation of CD1d-restricted NKT cell responses by using N-acyl variants of alpha-galactosylceramides, PNAS 2005, 3383-3388, 102(9).

Zajonc et al., Structure and function of a potent agonist for the semi-invariant natural killer T cell receptor, Naure Immunology 2005, 810-818, 6(8).

Zhou, Dapeng, The Immunological Function of iGb3, Current Protein and Peptide Science 2006, 325-333, 7.

Zigmund et al., beta-Glucosylceramide: a novel method for enhancement of natural killer T lymphoycte plasticity in murine models of immune-mediated disorders, Gut 2007, 82-89, 56.

Zigmund et al., beta-Glycosphingolipids improve glucose intolerance and hepatic steatosis of the Cohen diabetic rat, Am J Physiol Endocrinol Metab 2009, E72-E78, 296.

Zigmund et al., Treatment of non-alcoholic steatohepatitis by beta-glucoceramide: A phase I/II clinical study, Hepatology 2006, 180A, 44, Poster #1256, Title only.

\* cited by examiner

US 8,592,394 B2

SYNTHETIC DERIVATIVES BETA GLYCOLIPIDS AND COMPOSITIONS THEREOF FOR THE TREATMENT OF PATHOLOGIC DISORDERS

REFERENCE TO RELATED PATENT APPLICATIONS

This application is a continuation-in-part of U.S. patent application Ser. No. 12/586,100 filed on Sep. 17, 2009, which is a continuation-in-part of U.S. patent application Ser. No. 10/675,980 filed on Sep. 30, 2003.

FIELD OF THE INVENTION

The invention relates to novel synthetic derivatives of β-glycolipids and uses thereof as immunomodulators. More particularly, the invention provides the compounds of any one of Formula I, II III and IV or any mixture or combination thereof, as well as compositions and methods thereof for the treatment of immune-related disorders.

BACKGROUND OF THE INVENTION

All publications mentioned throughout this application are fully incorporated herein by reference, including all references cited therein.

Immune therapy involves the exposure of components of the immune system to various elements (cytokines, disease associated antigens and natural metabolites) to combat disease processes in which a dysregulated immune response is thought to play a role. Immune dysregulation is thought to play a major part in the pathogenesis or disease course of a great number of disease processes, including various neoplastic, inflammatory, infectious and genetic entities.

These disorders can be perceived as a dysbalance between pro-inflammatory (Th1) and anti-inflammatory (Th2) cytokines, and few of them are described herein below.

Natural killer T (NKT) cells are a highly conserved subset of lymphocytes that can be broadly categorized into two groups [Brigl, M. and Brenner M. B. Annu. Rev. Immunol. 22: 817-90 (2004)]. In mice, invariant NKT (iNKT; also referred to as classical or type I NKT) cells express a conserved invariant αβ T cell receptor (TCR), encoded by the Vα14 (Vα24 in humans) and Jα18 gene segments, paired with a set of Vβ chains [Bendelac. A. et al. Annu. Rev. Immunol. 25:297-336 (2007)]. These cells are CD1d-dependent, reactive to α-Galctosyl-ceramide (α-GalCer), and are potent producers of both interleukin 4 (IL-4) and interferon gamma (IFN-γ). Non-classical or type II NKT cells, which use variable TCRs, are distinct from type I NKT cells and have been identified in both humans and mice [Chiu, Y. H. et al. Nat. Immunol. 3:55-60 (2002); Godfrey, D. I. et al. Science, 306: 1687-9 (2004)]. Type II (non-classical) NKT cells, which may be either CD161-positive or negative, are also CD1d-dependent and potent IL-4 and IFN-γ producers. However they have more diversely structured TCR α and β chains and are not α-Gal-Cer reactive [Brigl, M. and Brenner M. B. Annu. Rev. Immunol. 22: 817-90 (2004); Bendelac. A. et al. Annu. Rev. Immunol. 25:297-336 (2007)].

The CD1 glycoprotein family resembles classical peptide antigen presenting molecules except that the nonpolar, hydrophobic, antigen-binding groove has evolved to present lipid antigens [Brigl, M. and Brenner M. B. Annu. Rev. Immunol. 22: 817-90 (2004)]. Antigens presented by CD1d and/or the level at which they are presented can have profound effects on immune regulation of autoimmune, infectious, and malignant disorders [Brutkiewicz, R. R. J. Immunol. 177: 769-75 (2006); Brutkiewicz, R. R. et al. Crit. Rev. Immunol. 23: 403-19 (2003); Van Kaer, L. Curr. Opin. Immunol. 19: 354-64 (2007)]. Abnormalities in the number and function of NKT cells have been observed in patients with autoimmune diseases and in a variety of mouse strains genetically predisposed for the development of autoimmune diseases [Miyake, S and Yamamura, T. Curr. Drug Targets Immune Endocr. Metabol. Disord. 5: 315-22 (2005)]. Targeting CD1d-mediated antigen presentation can serve as a novel approach for intervening in autoimmune diseases [Brutkiewicz, R. R. et al. Crit. Rev. Immunol. 23: 403-19 (2003); Singh, A. K. et al. J. Exp. Med. 194: 1801-11 (2001); Sandberg, J. K. and Ljunggren, H. G. Trends Immunol. 26: 347-9 (2005)].

Type I and type II NKT cells share some important characteristics. However, their distinct developmental and selection requirements indicate that they have distinct specificities [Godfrey, D. I. et al. Science, 306: 1687-9 (2004)]. As both type I and type II NKT cells are CD1d-dependent, any phenotype observed in CD1d-deficient mice might be due to a deficiency in type II NKT cells rather than type I NKT cells [Huber, S. et al. J. Immunol. 170: 3147-53 (2003); Exley, M. A. and Koziel, M. J. Hepatology, 40:1033-40 (2004); Dao, T. et al. Eur. J. Immunol. 34: 3542-52 (2004)], and the functional relationship between these two cell types is unclear. To this end, the combined use of TCR Jα18-deficient mice and CD1d-deficient mice is useful to distinguish between type I and type II NKT cells at the functional level in vivo. Although iNKT (invariant NKT) cells have been shown to be involved in autoimmune diseases, infectious diseases, and asthma as well as in the antitumor immune responses, not much is known about type II NKT cells.

NKT lymphocytes are influenced by a variety of self ligands and environmental stimuli, including disease target antigens, antigen presenting cells, co-stimulatory signals, soluble factors, and effector cells [Godfrey, D. I. and Kronenberg, M., J. Clin. Invest. 114: 1379-88 (2004); Smyth, M. J. et al. Curr. Opin. Immunol. 14:165-71 (2002)]. NKT cell functions are controlled by affinity thresholds for glycosphingolipid antigens that play an important role in cell activation[16]. Activation and development of NKTs are guided by information provided by glycosphingolipid metabolic pathways [Hammond, K. J. and Godfrey, D. I. Tissue Antigens, 59: 353-63 (2002); Kronenberg, M. Annu. Rev. Immunol. 23: 877-900 (2005)].

Currently, the only efficient method to selectively stimulate NKT cells in vivo is the sea sponge-derived agent αGalCer [Van Kaer, L. Nat. Rev. Immunol. 5: 31-42 (2005)]. Tetrameric forms of CD1d molecules bound to αGalCer, which have sufficient affinity for the TCR of iNKT cells, allow for the detection of these cells by flow cytometry [Taniguchi, M. et al. Annu. Rev. Immunol. 21: 483-513 (2003); Bezbradica, J. S. et al. J. Immunol. 174: 4696-705 (2005)]. Administration of αGalCer results in potent activation of NKT cells, rapid and robust cytokine production, and further activation of a variety of cells of the innate and adaptive immune systems

[Van Kaer, L. Nat. Rev. Immunol. 5: 31-42 (2005)]. Transient administration of αGalCer induces both IL-4 and IFN-γ secretion, while repeated administration favors production of Th2 cytokines [Miyake, S and Yamamura, T. Curr. Drug Targets Immune Endocr. Metabol. Disord. 5: 315-22 (2005); Yamamura, T. et al. Curr. Top Med. Chem. 4: 561-7 (2004)]. OCH, a sphingosine-truncated analog of αGalCer, was shown to be a potential therapeutic reagent for a variety of Th1-mediated autoimmune diseases through its selective induction of Th2 cytokines from iNKT cells [Oki, S. et al. J. Clin. Invest. 113: 1631-40 (2004)].

Both rodent and human iNKT cells have been reported to recognize αGalCer in the context of CD1d. Therefore, activated iNKT cells play a pivotal role in modulating many aspects of the innate immune response within the liver during a diverse array of pathological processes [Ajuebor, M. N. and Swain, M. G. Immunology, 105: 137-43 (2002)]. However, αGalCer has been shown to be hepatotoxic in mice, which has limited its use in human testing [Osman, Y. et al. Eur. J. Immunol. 30: 1919-28 (2000); Biburger, M. and Tiegs, G. J. Immunol. 175: 1540-50 (2005)].

While the responses to antigen presentation can be complex, the process of antigen binding, presentation, and recognition by T cell receptors is fundamentally a series of molecular recognition events. In recent years, glycolipid presentation by CD1 proteins has emerged as an important aspect of antigen recognition [Brigl, M. and Brenner M. B. Annu. Rev. Immunol. 22: 817-90 (2004)].

Several glycosphingolipids and phospholipids derived from mammalian, bacterial, protozoan, and plant species have been identified as possible natural ligands for NKT cells [Zajonc, D. M. et al. Nat. Immunol. 6: 810-8 (2005); Tsuji, M. Cell Mol. Life Sci. 63: 1889-98 (2006)]. A semi-invariant αβTCR can recognize iGb3, a mammalian glycosphingolipid, as well as a microbial alpha-glycuronylceramide found in the cell wall of Gram-negative, lipopolysaccharide-negative bacteria [Zhou, D. Curr. Protein Pept. Sci. 7: 325-33 (2006)]. iGb3 has been suggested as a candidate recognized by NKT cells under pathophysiological conditions, such as cancer and autoimmune disease [Zhou, D. Curr. Protein Pept. Sci. 7: 325-33 (2006); Hansen, D. S. and Schofield, L. Int. J. Parasitol. 34: 15-25 (2004)]. However, the normal development and function of invariant NKT cells in mice with iGb3 deficiency has been described [Porubsky, S. et al. Proc. Natl. Acad. Sci. U.S.A. 104: 5977-82 (2007); Skold, M. and Behar, S. M. Infect. Immun. 71: 5447-55 (2003); Tupin, E. et al. Nat. Rev. Microbiol. 5: 405-17 (2007); Stanic, A. K. et al. Immunology, 109: 171-84 (2003)].

Alpha-anomeric D-glycosylceramides are unknown in mammals. In contrast to current thinking, β-anomeric GalCer can induce CD1d-dependent biological activities in mice, albeit at lower potency than α-anomeric GalCer. β-anomeric glycolipids may provide a source of weakly reactive self antigens. Binding studies using CD1d tetramers loaded with α-GalCer (C12) demonstrated significant but lower intensity binding to NKT cells when compared with α-GalCer. Glucosylceramide (β-GC), a naturally occurring glycosphingolipid, is a metabolic intermediate in the anabolic and catabolic pathways of glycosphingolipids [Yang, Y. G. et al. Cell Mol. Immunol. 2: 323-9 (2005)]. Its synthesis from ceramide is catalyzed by glucosylceramide synthase [Lalazar, G. et al. Mini Rev. Med. Chem. 6: 1249-53 (2006)]. Inherited deficiency of glucosylceramidase (a lysosomal hydrolase) results in high serum levels of β-GC and Gaucher's disease. These patients have altered humoral and cellular immune profiles, and distorted NKT lymphocyte numbers and functions [Lalazar, G. et al. Mini Rev. Med. Chem. 6: 1249-53 (2006)]. In vitro, CD1d-bound β-GC inhibits NKT cell activation by αGalCer [Ortaldo, J. R. et al. J. Immunol. 172: 943-53 (2004)]. Administration of β-D-GlcCer in vivo attenuated the NKT-mediated damage in concanavalin A (Con A) hepatitis, immune-mediated colitis, and animal models of diabetes [Yang, Y. G. et al. Cell Mol. Immunol. 2: 323-9 (2005); Margalit, M. et. al. Am. J. Physiol. Gastrointest. Liver Physiol. 289: G917-25 (2005); Zigmond, E. et al. Gut 56: 82-9 (2007); Margalit, M. et al. J. Pharmacol. Exp. Ther. 319: 105-10 (2006)].

iNKT cells are influenced by a variety of self ligands and environmental stimuli, including disease target antigens, antigen presenting cells, co-stimulatory signals, soluble factors, and effector cells [Godfrey, D. I. and Kronenberg, M., J. Clin. Invest. 114: 1379-88 (2004); Smith, P. A. et al. AIHA J. (Fairfax, Va.) 63: 284-92 (2002)]. iNKT cell functions are controlled by affinity thresholds for glycosphingolipid antigens that play an important role in cell activation [Stanic, A. K. et al. J. Immunol. 171: 4539-51 (2003)]. However, cellular interactions among NKT cell subsets and their potential role in the regulation of an iNKT cell mediated disease have not been previously investigated.

Abnormalities in the number and function of NKT cells have been observed in patients with autoimmune diseases and in a variety of mouse strains genetically predisposed to the development of autoimmune diseases [Miyake, S. and Yamamura, Curr. Top Microbiol. Immunol. 314: 251-67 (2007)]. Targeting CD1d-mediated antigen presentation can thus serve as a novel approach for intervening in autoimmune diseases [Brutkiewicz, R. R. J. Immunol. 177: 769-75 (2006); Sandberg, J. K. and Ljunggren, H. G. Trends Immunol. 26: 347-9 (2005)].

The Con A model is a widely utilized mouse model that mimics many aspects of human autoimmune hepatitis. It induces massive liver necrosis in mice simultaneously with lymphocyte infiltration in the liver, high levels of apoptotic hepatocytes, and elevated serum alanine aminotransferase (ALT) and aspartate aminotransferase (AST). The liver injury was confirmed to be NKT cell-mediated [Tiegs, G. Z. Gastroenterol. 45: 63-70 (2007)]. iNKT cells have recently been shown to play a key role in the development of Con A-induced hepatitis: both Jα18−/− and CD1d−/− mice that lack iNKT cells are relatively resistant to Con A-induced hepatic injury [Kaneko, Y. et al. J. Exp. Med. 191: 105-14 (2000); Takeda, K. and Okumura, K. Hum. Cell, 14: 159-63 (2001)]. Signaling through the Janus kinase/signal transducers and activators of transcription (JAK/STAT) pathway is an important signal pathway that is activated immediately after cytokine stimulation [Darnell, J. E. Jr. et al. Science, 264: 1415-21 (1994)]. Con A-induced hepatitis is largely dependent on interferon IFN-γ/STAT1, as IFN-γ and STAT1-deficient mice are resistant to Con A-induced hepatitis. On the other hand, IL-6 and cytokines that activate STAT3 protect mice against liver damage.

There is therefore a need to provide safe and effective glycolipid analogs for use as immunomodulators. Such novel analogs may preferably modulate activity of iNKT cells and different signal transductions pathways and thereby alleviate immune-related disorders.

The present invention thus describes the synthesis non-natural different analogs of β-GC. One of these analogs, ALIB-97 is characterized by a bulky acyl-residue and by a thiourea bond. Because ConA-induced liver damage is mediated by iNKT cells, the inventors used this model of liver disease to examine the newly synthesized β-glycosphingolipid analogs of the invention. The invention demonstrates that orally administered ALIB-97 is a potent ligand that is effective in alleviating NKT cell-mediated liver damage in ConA-induced hepatitis. This effect was mediated by altered STAT protein expression and suppression of the production of pro-inflammatory cytokines. The effect noted for ALIB-97 was superior to that of the natural glycosphingolipids and comparable to that of dexamethasone.

The inventors have further investigated the potential effect of the novel analogs of the invention on other immune-related disorders using the ob/ob mice that serve as a model for metabolic syndrome and NASH.

Non-alcoholic fatty liver disease (NAFLD) has emerged as a substantial public health concern as it may progresses to non-alcoholic steatohepatitis (NASH) and end stage liver disease [Matteoni, C. A. et al. Gastroenterology, 116: 1413-9 (1999)]. It is commonly associated with clinical features of the metabolic syndrome including type 2 diabetes, obesity and dyslipidemia. Insulin resistance plays an important role in the pathogenesis of NASH. The two-hit model, suggesting an initial lipid accumulation in the hepatocytes, followed by a second hit, was suggested for the development of liver injury.

c-Jun N-terminal kinase (JNK) is a member of the subfamily of mitogen-activated protein kinases (MAPKs), and regulates several cellular responses including differentiation, proliferation, migration, immune reaction, and cell death in response to a diverse range of stimuli [Kodama, Y. and Brenner, D. A. Hepatology, 49: 6-8 (2009)]. Three different genes for JNKs, JNK1, JNK2 and JNK3, are known. JNK3 expression is largely restricted to brain, heart and testis whereas JNK1 and 2 are expressed ubiquitously [Davis, 2000]. Recent studies have suggested that activation of JNK plays a central role in the development of obesity, insulin resistance and steatohepatitis [Hirosumi, 2002; Tuncman, 2006; Schattenberg, 2006]. Recent studies have demonstrated that JNK1 and JNK2 differ in function [Singh, R. et al. Hepatology, 49: 87-96 (2009)] [Schattenberg, 2006]. Both isoforms were found to mediate insulin resistance in high-fat diet (HFD)-fed mice, but distinct effects were found for steatohepatitis. Activation of JNK1 was shown to promote the development of steatohepatitis in the murine methionine- and choline-deficient (MCD) diet [Schattenberg, 2006]. Knockdown of JNK2 improved insulin sensitivity but had no effect on hepatic steatosis and markedly increased liver injury [Singh, R. et al. Hepatology, 49: 87-96 (2009)]. The differential effect of JNK2 knockdown, which is effective on insulin resistance but not on hepatic steatosis, highlights that hepatic steatosis, is more than a mere consequence of insulin resistance. JNK1 might have a direct effect on hepatic lipogenesis that is independent of insulin resistance. The distinct roles for JNK1 and JNK2 in hepatocyte death are still controversial. JNK1 phosphorylates and activates Itch, which induces ubiquitination/degradation of c-FLIP (cellular FLICE-inhibitory protein) and subsequent caspase-8-dependent apoptosis, whereas JNK2 may activate caspase-8 more directly [Chang, 2006; Wang, 2006]. Activation of JNK1/2 seems to be involved in TNF-α-induced insulin resistance, causing phosphorylation of IRS1 at the Ser312 residue. JNK2 (−/−) mice fed a HFD are obese and insulin-resistant, similar to wild-type mice, and have increased liver injury [Singh, R. et al. Hepatology, 49: 87-96 (2009)]. This suggests that JNK1 promotes steatosis and hepatitis, whereas JNK2 inhibits hepatocytes' death by blocking the mitochondrial death pathway.

One of the major pathways that are activated by insulin is the Akt (or PKB) pathway which mediates the effects of insulin on glucose transport, glycogen synthesis, protein synthesis, lipogenesis and suppression of hepatic gluconeogenesis. Akt is activated by phospholipid binding and activation loop phosphorylation at Thr308 by PDK1 [Lawlor, 2001]. Akt-2 (PKBβ) is highly expressed in insulin-responsive tissues such as adipose tissue [Walker, 1998]. Exciting new data establishes Akt-2 as an essential gene for the maintenance of normal glucose homeostasis [Cho, 2001]. Mice deficient in Akt-2 display many of the typical features of Type II diabetes mellitus in humans, namely hyperglycemia, elevated blood insulin levels, and insulin resistance in the liver and to a minor extent muscle.

Insulin resistance is characterized by a complex interaction of genetic determinants, lifestyle, ageing and nutritional factors. Visceral obesity is regarded as the major cause of insulin resistance. Visceral obesity has also been defined as an important component of the metabolic syndrome, and increased visceral fat mass contributes to the development of obesity-related disorders such as insulin resistance, non-alcoholic fatty liver disease, hypertension, diabetes and CVD [de Luca, 2008]. Chronic systemic inflammation has been proposed to have an important role in the pathogenesis of obesity-related insulin resistance [Bastard, 2006]. There is strong evidence that adipose tissue not only releases FFA that contributes to insulin resistance in liver and muscle, but also produces a wide range of inflammatory molecules including TNF-α and IL-6 which may have local effects on adipose physiology and also systemic effects on other tissues. Some factors such as leptin, TNF-α, IL-6 and resistin are overproduced during obesity, and conversely the plasma levels of adiponectin are reduced during obesity. Both adipose tissue and the liver have an architectural organization in which metabolic cells (adipocytes or hepatocytes) are in close proximity to immune cells (Kupffer cells or macrophages), forming a suitable environment for continuous and dynamic interactions between immune and metabolic responses in both tissues [Hotamisligil, G. S. Nature, 444: 860-7 (2006)]. TNF-α is overexpressed in the adipose tissue of obese mice supporting a link between obesity, diabetes and chronic inflammation [Hotamisligil, G. S. et al. Science, 259: 87-91 (1993)]. White adipose tissue (WAT) is the site of energy storage and is composed of many cell types, adipocytes being the most abundant. Other cell types present in WAT are included in the stromal-vascular fraction, of which approximately 10% are CD14+CD31+ macrophages [Curat, C. A. et al. Diabetes, 53: 1285-92 (2004)]. The number of macrophages present in WAT is directly correlated with adiposity and with adipocyte size in both human subjects and mice [Curat, C. A. et al. Diabetes, 53: 1285-92 (2004); Weisberg, S. P. et al. J. Clin. Invest. 112: 1796-808 (2003); Xu, H. et al. J. Clin. Invest. 112: 1821-30 (2003)]. Adipocytes secrete a variety of protein signals as well as cytokines and chemokines, such as TNF-α, IL-6 and IL-10. About one third of the IL-6 level in the peripheral circulation originates from adipose tissue [Fernandez-Real, J. M. and Ricart, W. Endocr. Rev. 24: 278-301 (2003)]. With increasing obesity, the contribution of IL-6 from the adipose tissue increases [Trayhurn, P. et al. C. J. Nutr. 136: 1935S-1939S (2006); Kershaw, E. E. and Flier, J. S. J. Clin. Endocrinol. Metab. 89: 2548-56 (2004)]. Additionally, anatomically, visceral abdominal fat is venouslt drained in a portal system to the liver, thus further consolidating the effect of WAT inflammatory processes on hepatic function.

Regulatory T cells (Tregs) are fundamental in controlling various immune responses. The CD4+ regulatory T cells have been categorized into two major subgroups based on their ontogeny: The naturally occurring forkhead box P3 (FOXP3)+CD4+CD25+ regulatory T cells referred as Treg cells and the inducible regulatory T cells, which are generated in the periphery under various tolerogenic conditions [Shevach, E. M. Immunity, 25: 195-201 (2006)].

Both α and β glycosphingolipids have an immune modulatory role and can alter the induction and distribution of Tregs, affecting immune-system dependent disorders [Araki, M. et al. Curr. Med. Chem. 15: 2337-45 (2008); Lalazar, G. et al. Mini Rev. Med. Chem. 6: 1249-53 (2006); Van Kaer, L. Nat. Rev. Immunol. 5: 31-42 (2005)]. This effect is dependent on dendritic cells (DCs) and/or alteration of NKT cells palstiticity [Ilan, Y. et al. Transplantation, 83: 458-67 (2007); Margalit, M. et al. Am. J. Physiol. Gastrointest. Liver Physiol. 289: G917-25 (2005); Zigmond, E. et al. Gut, 56: 82-9 (2007); Onoe, K. et al. Immunol. Res. 38: 319-32 (2007)]. Beta-glycolipids were shown to alleviate the metabolic syndrome in animal models and humans [Margalit, M. et al. J. Pharmacol. Exp. Ther. 319: 105-10 (2006); Zigmond, E. et al. Am. J. Physiol. Endocrinol. Metab. 296: E72-8 (2009); Zigmond, E. et al. Hepatology, 44: 180A (2006)].

The present invention demonstrates the beneficial effect of the novel analogs using this model and thereby the applicability of these novel compounds as immuno-modulating agents. More specifically, the results presented by the invention shed light on a cross talk between the immune system, especially in the adipose tissue and JNK signaling pathway. The data suggest new potential therapeutic targets for insulin resistance and NASH. Adipose tissue-specific CD4+ T regulatory cells are suggested as central players in the interplay between the immune system and the pancreas. They may exert their effect by secreting cytokines or by enhancing chemokines, including adipokine secretion from cells in the relevant microenvironment. Ligands such as the novel analogs of the invention and specifically, ALIB-97, via their oral effect on the induction of CD4+ T regulatory cells may serve as novel approach for the alleviation of insulin resistance and for the treatment of type 2 diabetes and NASH.

Thus, the present invention now provides novel synthetic derivatives of β-glycolipids, and particularly of the compounds of Formulas I, II, III and IV, and demonstrates uses thereof in the treatment of pathologic disorders.

It is therefore an object of the invention to provide novel synthetic derivatives of β-glycolipids, as well as compositions thereof and methods for treating pathologic disorders such as immune-related disorders and neurodegenerative disorders.

These and other objects of the invention will become clearer as the description proceeds.

SUMMARY OF THE INVENTION

In a first aspect, the invention relates to synthetic derivatives of β-glycolipids, more particularly, the invention relates to a compound of Formula I, or isomer thereof or a pharmaceutically acceptable salt thereof, Formula I being:

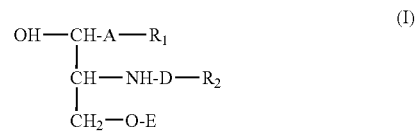

wherein

A represents alkenylene or alkylene bivalent radical selected from —CH═CH— and —CH(OH)—CH$_2$—;

D represents a bivalent radical selected from —CSNH—, —CONH—, —CS—, and —SO$_2$—;

E represents a glycosyl radical selected from glucosyl, galactosyl, sulfated galactosyl, manosyl, and lactosyl;

R$_1$ is a linear C$_{8-21}$alkyl; and

R$_2$ is a univalent radical selected from linear or branched alkyl or alkenyl chains optionally substituted with hydroxyl, adamantanyl, and norbornenyl. In one embodiment, A in said Formula I is —CH═CH—. In other embodiment, E in said formula I is glucosyl. R$_1$ in said Formula I may be C$_{10-16}$ alkyl, for example C$_{13}$alkyl. In other embodiment of the invention, said R$_2$ in said formula I is selected from linear C$_{6-18}$alkyl and adamantanyl. Said glycosyl in Formula I is preferably β-glycosyl.

According to one embodiment, the compound of the invention may be the compound of Formula II, also designated in certain embodiments, as AD2897 or as ALIB-97, or any isomer thereof or a pharmaceutically acceptable salt thereof. Formula II being:

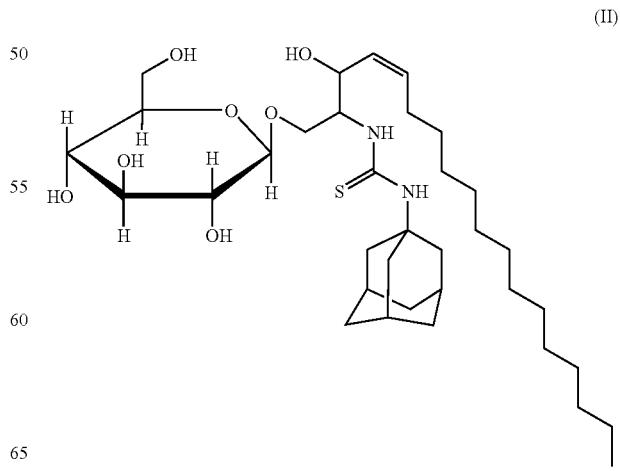

According to another embodiment, the compound of the invention may be the compound of Formula III, also designated as AD2898, or a pharmaceutically acceptable salt thereof. Formula III being:

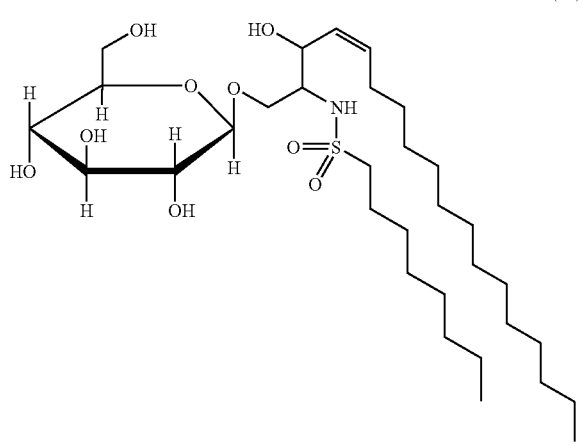

(III)

In a further preferred embodiment, the compound of the invention may be the compound of Formula IV, also designated as AD2899, or a pharmaceutically acceptable salt thereof.

Formula IV being:

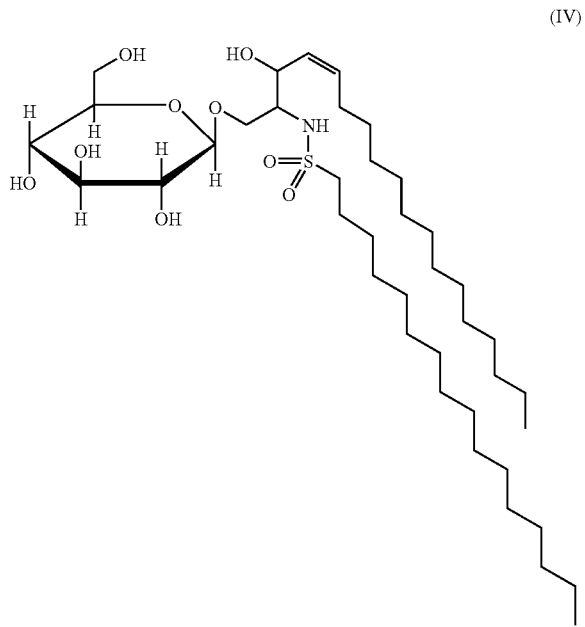

(IV)

In a second aspect, the invention relates to a composition comprising at least one of the compounds of any one of Formula I, II, III and IV or any mixtures or combinations thereof. The composition of the invention may further comprise at least one of a pharmaceutically acceptable carrier, diluent, excipient and/or additive.

As a third aspect, the invention provides a therapeutic composition for treating, preventing, ameliorating or delaying the onset of a pathologic disorder in a mammalian subject.

More particularly, the therapeutic composition of the invention may comprise as an active ingredient any one of: (a) at least one of the compounds of Formula I, II, III and IV; (b) a mixture of at least two compounds of Formula I, II, III and IV; (c) at least one component of said subject's immune-system which was pre-exposed to an effective amount of any one of the compounds of said Formula I, II, III or IV, or to any mixture or any combination thereof; and (d) any combinations of (a), (b) and (c). It should be noted that the therapeutic composition of the invention may optionally further comprises at least one of a pharmaceutically acceptable carrier, diluent, excipient and/or additive.

In a particular embodiment, the invention provides a therapeutic composition comprising a therapeutically effective amount of the compound of Formula II (ALIB-97), for treating, preventing, ameliorating or delaying the onset of a pathologic disorder in a mammalian subject.

According to one embodiment, the therapeutic composition of the invention may be an immunomodulatory composition particularly applicable in modulating the Th1/Th2, Th3 cell balance in a subject suffering from an immune-related disorder. Such immuno-modulation may activate or inhibit an immune response specifically directed toward said disorder in the treated subject.

According to a further aspect, the invention relates to a method for treating, preventing, ameliorating or delaying the onset of a pathologic disorder in a mammalian subject in need thereof. The method of the invention comprises the step of administering to the treated subject a therapeutically effective amount of any one of: (a) at least one compound of Formula I, II, III and IV; (b) a mixture of at least two compounds of Formula I, II, III and IV; (c) at least one component of the treated subject's immune-system which was pre-exposed to an effective amount of at least one of the compounds of any one of Formula I, II, III and IV, or to any mixture or any combination thereof; (d) a composition comprising any one of (a), (b) and (c) or (e) any combination of (a), (b), (c) and (d).

According to certain embodiments, the methods of the invention may lead to modulation of the Th1/Th2, Th3 cell balance in a subject suffering from an immune-related disorder. Such modulation may activate or inhibit an immune response specifically directed toward said disorder in the treated subject.

According to certain embodiments, such method may be particularly applicable in the treatment of immune related disorders such as Metabolic Syndrome or any of the conditions comprising the same, non-alcoholic fatty liver disease (NAFLD), non-alcoholic steatohepatitis (NASH), immune mediated hepatitis, an autoimmune disease, graft rejection pathology, inflammatory disease, hyperlipidemia, atherosclerosis and a neurodegenerative disorder.

Still further, another aspect of the invention relates to a method for the preparation of a medicament for the treatment of a pathologic disorder or condition in a subject in need thereof comprising the steps of: (A) providing an immunomodulatory compound comprising any one of: (a) at least one of the compounds of Formula I, II, III and IV; (b) a mixture of at least two compounds of Formula I, II, III and IV; (c) at least one component of said subject's immune-system which was pre-exposed to an effective amount of any one of the compounds of said Formula I, II, III or IV, or to any mixture or any combination thereof; and (B) admixing the immunomodulatory compound provided in step (A) with a pharmaceutically acceptable carrier.

These and other aspects of the invention will become apparent by the hand of the following figures and examples.

Effect of administration of the three synthetic analogs of the invention AD2897 (ALIB-97), AD2898, and AD2899 (1 µg or 10 µg/mice) upon liver function in a ConA induced hepatitis model, as reflected by AST (aspartate aminotransferase), black bars, and ALT (alanine aminotransferase), open bars.

Figure 2:
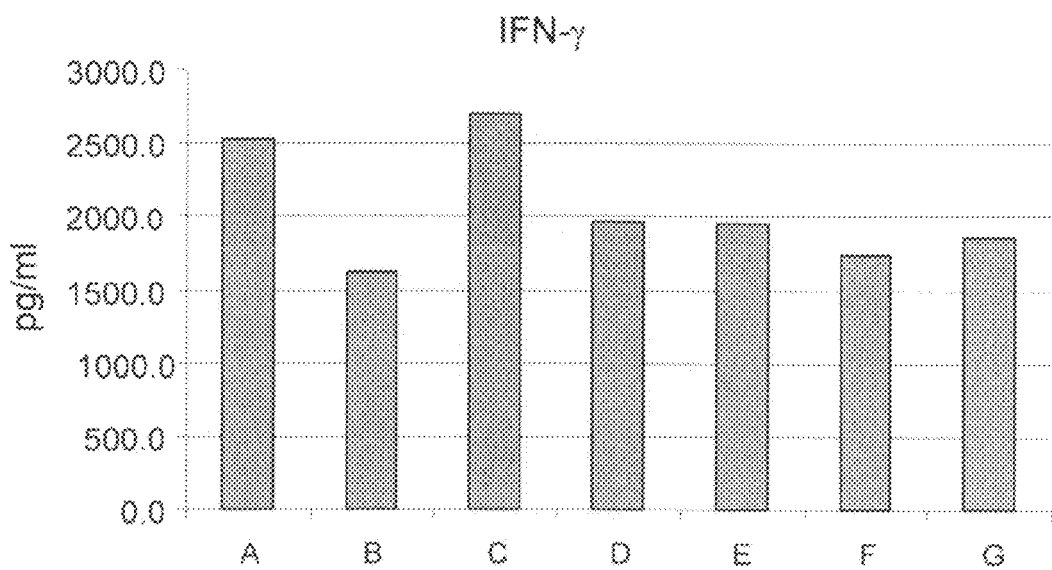

FIG. 2 An anti-inflammatory effect of the novel GC analogs

Figure demonstrates the effect of administration of β glycolipids synthetic analogs of the invention upon serum IFNγ levels using a ConA induced hepatitis model. Mice experimental groups are indicated in Table 1. A-control, B+C (AD2897 (ALIB-97) 1 µg and 10 µg/mice), D+E (AD2898 1 µg and 10 µg/mice), F+G (AD2899 1 µg and 10 µg/mice).

Figure 3:
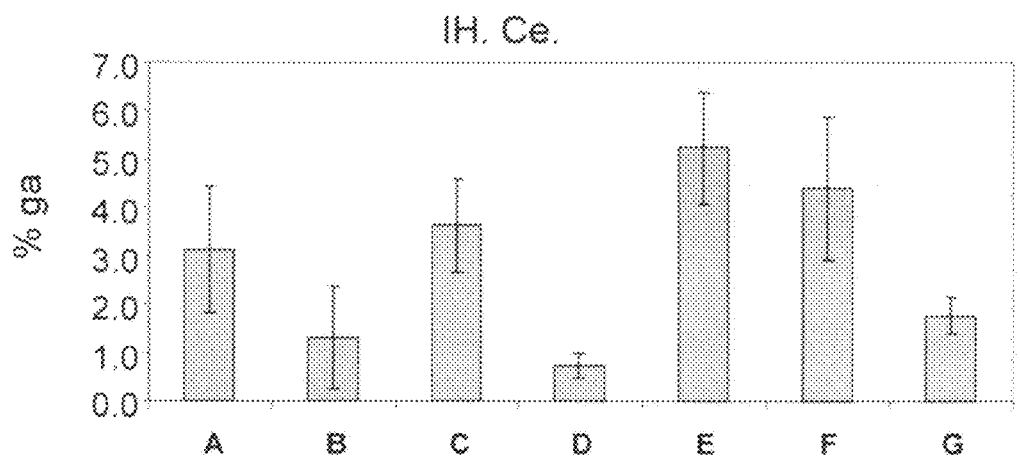

FIG. 3 The novel GC analogs reduce the level of intrahepatic NKT cell

The effect of administration of 1 µg or 10 µg/mice dosage regimes of β glycolipids synthetic analogs of the invention (AD2897 (ALIB-97), AD2898, and AD2899) upon intrahepatic NKT cell levels in a ConA induced hepatitis model. Abbreviations: IH (Intrahepatic); ce (cells); ga. (gated).

Figure 4:
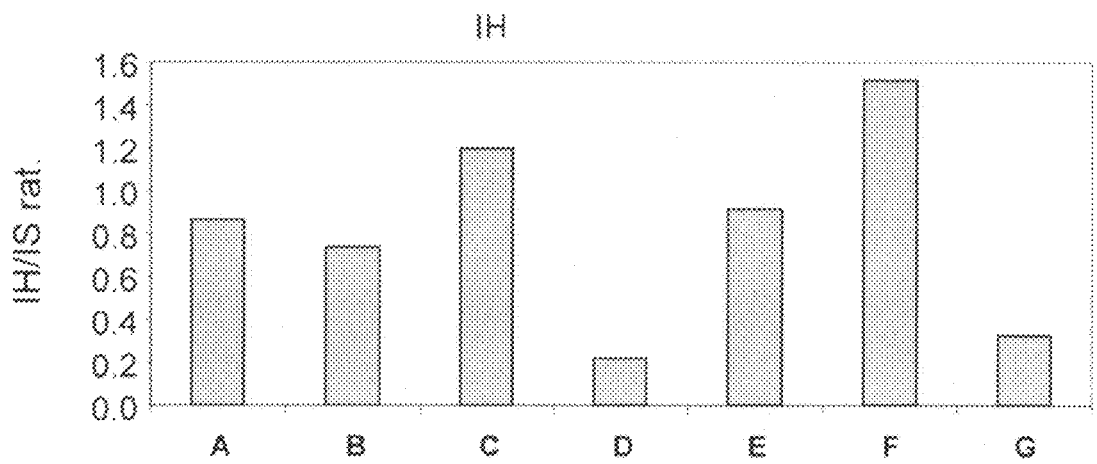

FIG. 4 The novel GC analogs reduce the ratio of intrahepatic/peripheral NKT cells Histogram depicting the effect of administration of 1 µg or 10 µg/mice dosage regimes of the β glycolipids synthetic analogs of the invention (AD2897 (ALIB-97), AD2898, and AD2899) upon the ratio of intrahepatic/peripheral NKT cells in ConA induced hepatitis mice. Abbreviations: IH (Intrahepatic); IS (intraspleenic); rat. (ratio).

Figure 5:
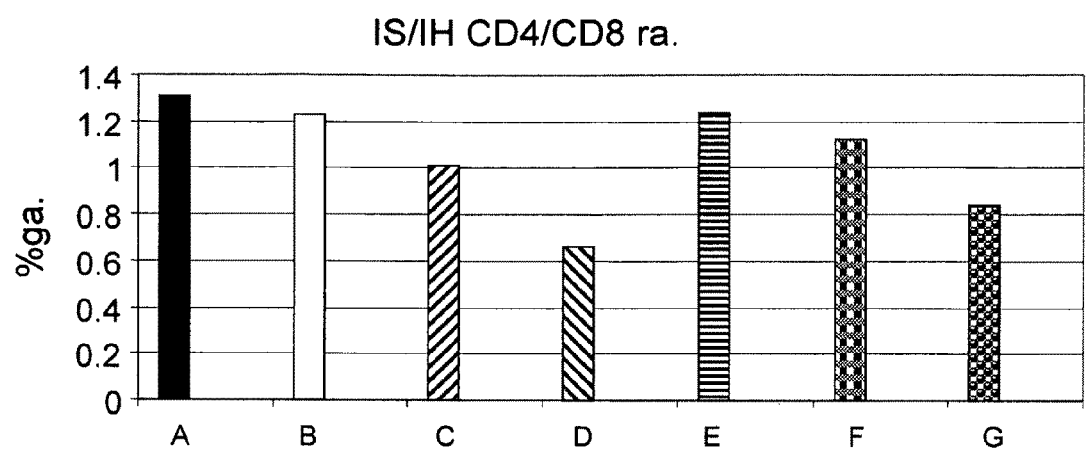

FIG. 5 The novel GC analogs increase the ratio of peripheral/intrahepatic NKT cells Histogram comparing the effect of 1 µg or 10 µg/mice regimes of the β glycolipids synthetic analogs of the invention (AD2897 (ALIB-97), AD2898, and AD2899) upon the ratio of peripheral/intrahepatic CD4:CD8 ratio. Abbreviations: IH (Intrahepatic); IS (intraspleenic); rat. (ratio), ga. (gated).

Figure 6:
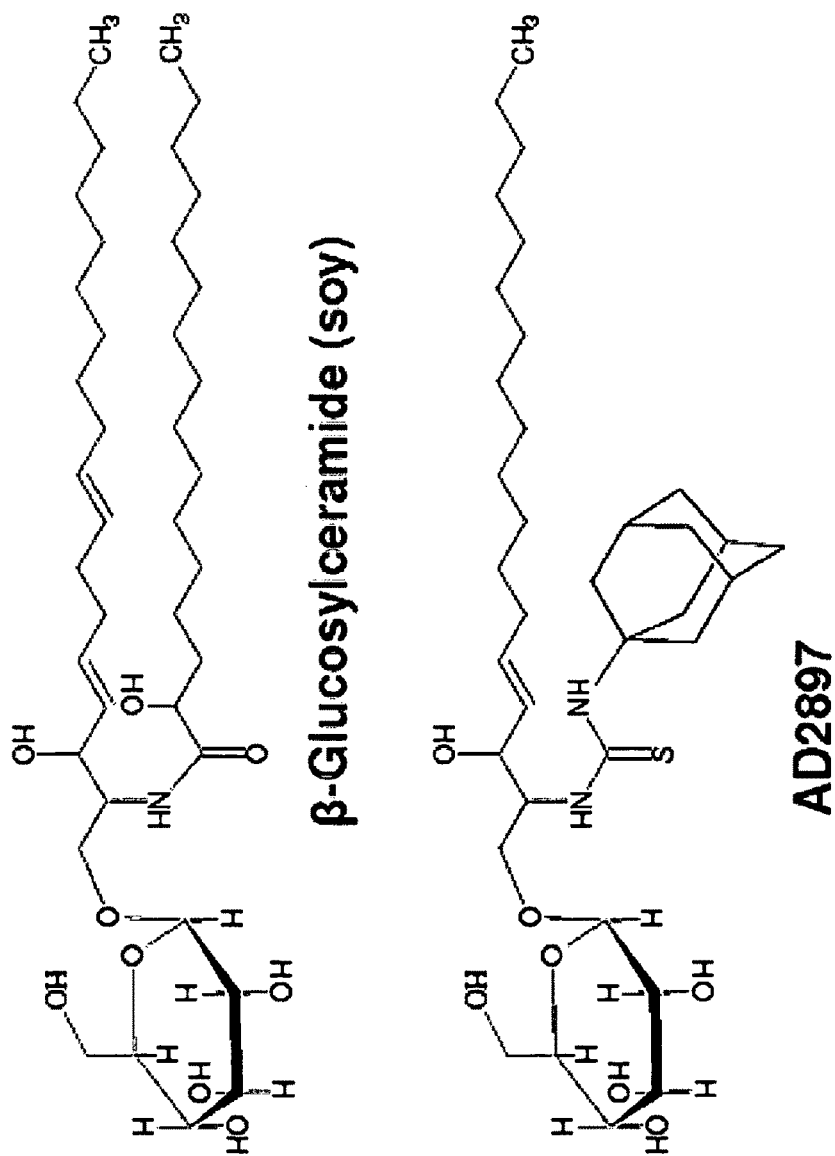

FIG. 6 Structure of the natural β-glycosylceramide and the ALIB-97 (Formula II) analog Structure of the natural β-glycosylceramide and the ALIB-97, newly synthesized analog characterized by a bulky adamantanyl residue and a thiourea bond.

FIG. 7A-7C.

Figure 7A:
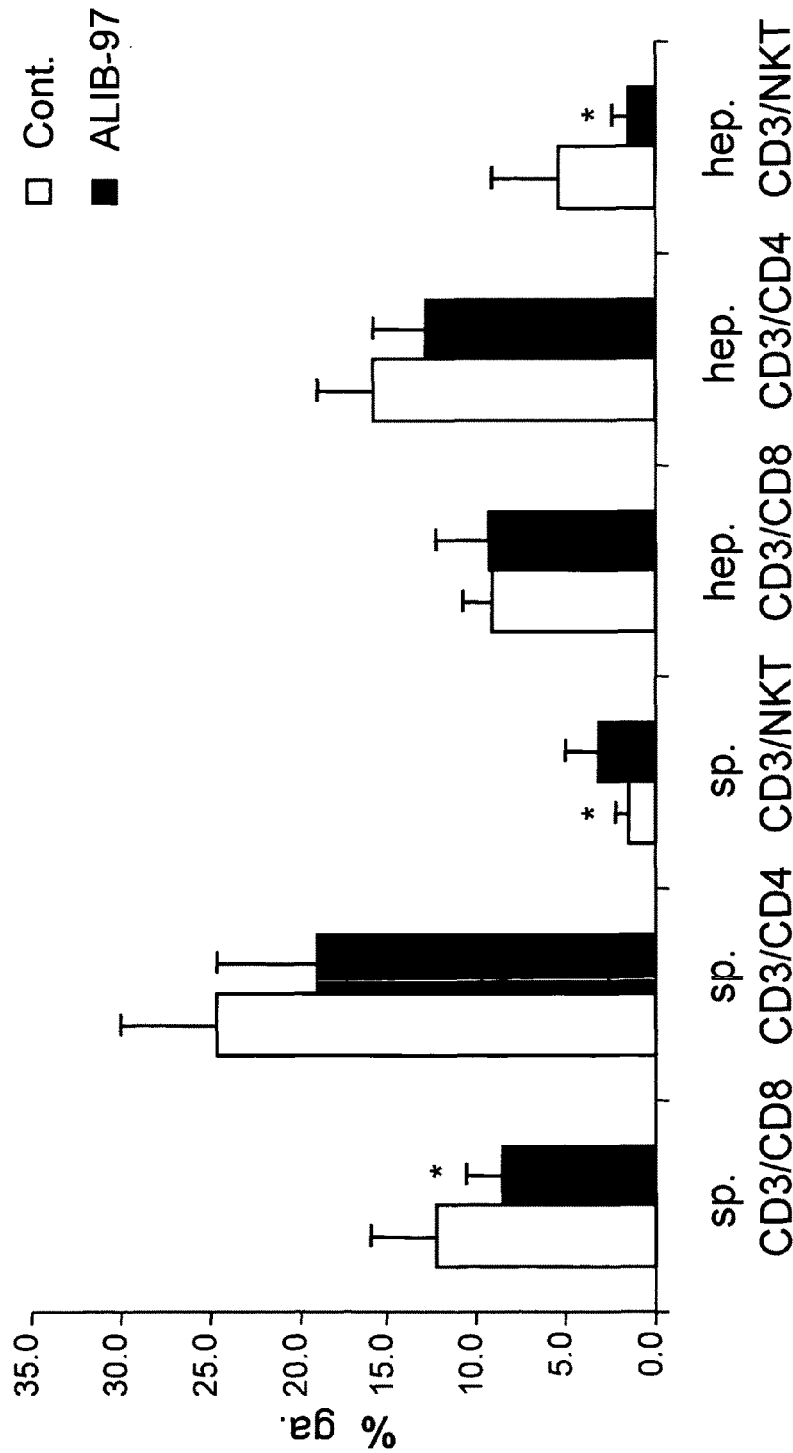

FIG. 7A. Analysis of T cell populations and T cell activation following administration of ALIB-97 and Con A injection Analysis of splenic and hepatic CD4+, CD8+, and CD3+ T cell expression following PO administration of ALIB-97, 20 hours after Con A injection.

Figure 7B:
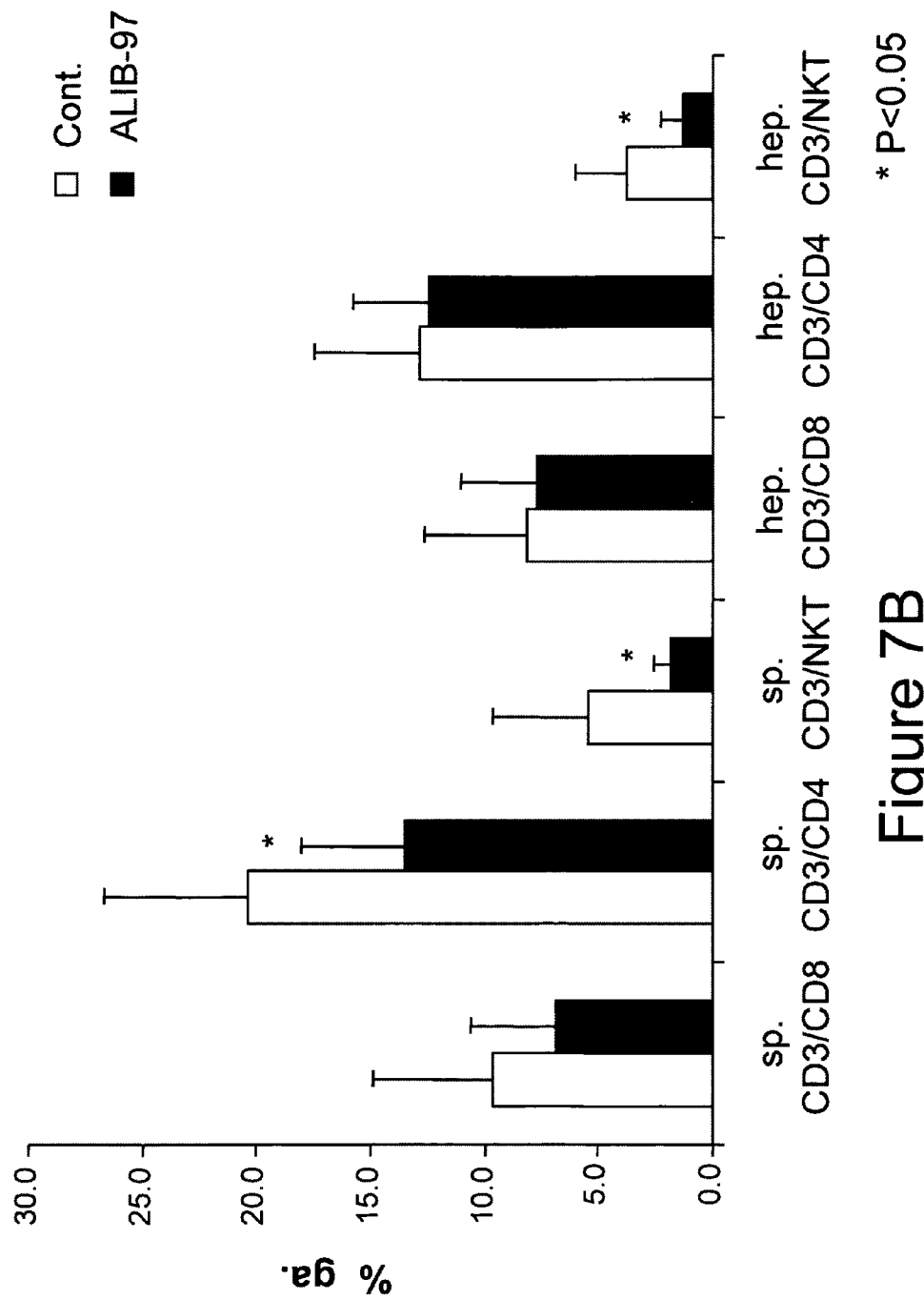

FIG. 7B. Analysis of splenic and hepatic CD4+, CD8+, and CD3+ T cell expression following IP administration of ALIB-97, 8 hours after Con A injection. Values represent the percentages of CD4+, CD8+, and NK1.1 cells expressing CD3.

Figure 7C:
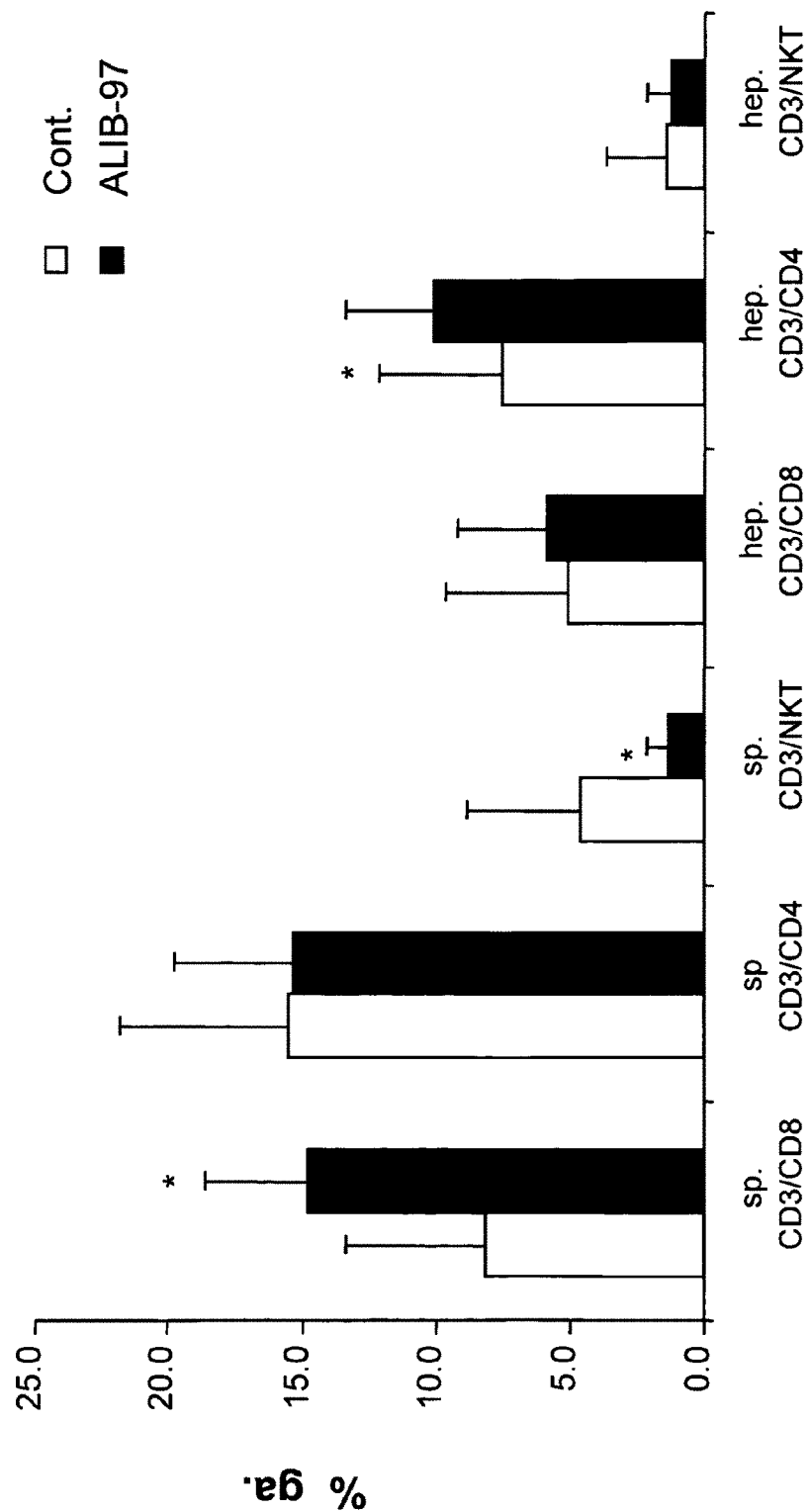

FIG. 7C. Analysis of splenic and hepatic CD4+ and CD8+ T cells.

Abbreviation: ga. (gate), sp. (splenic), hep. (hepatic), cont. (control, vehicle).

Figure 8A:
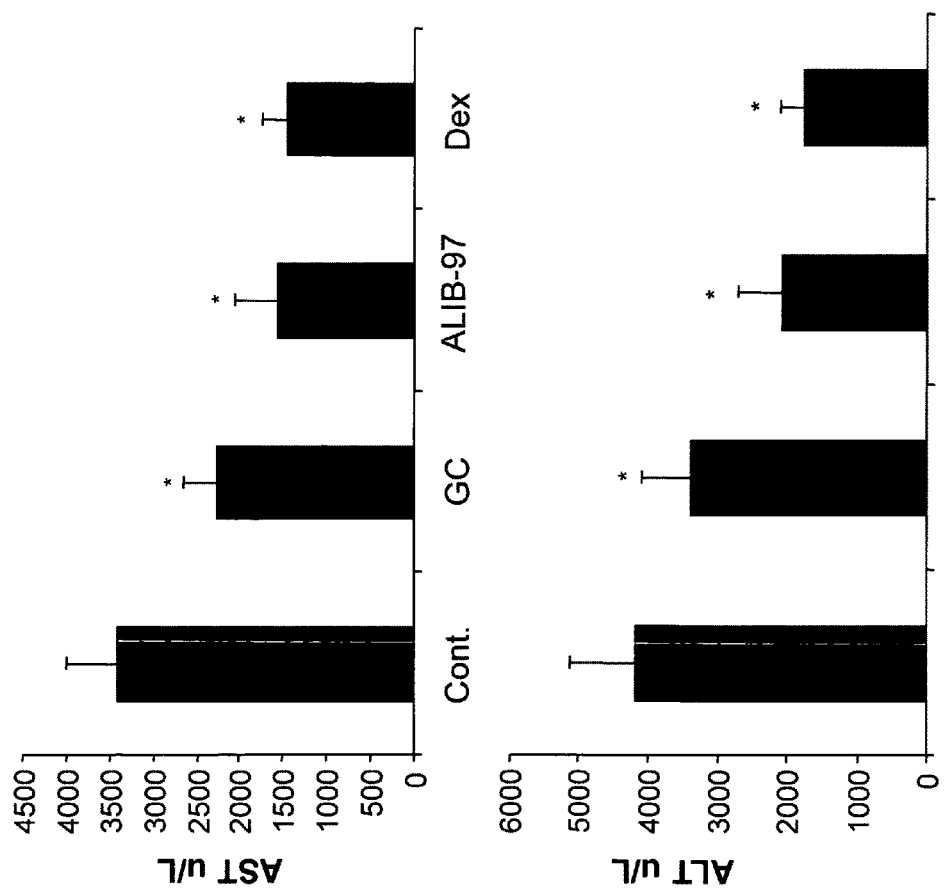
Figure 8B:
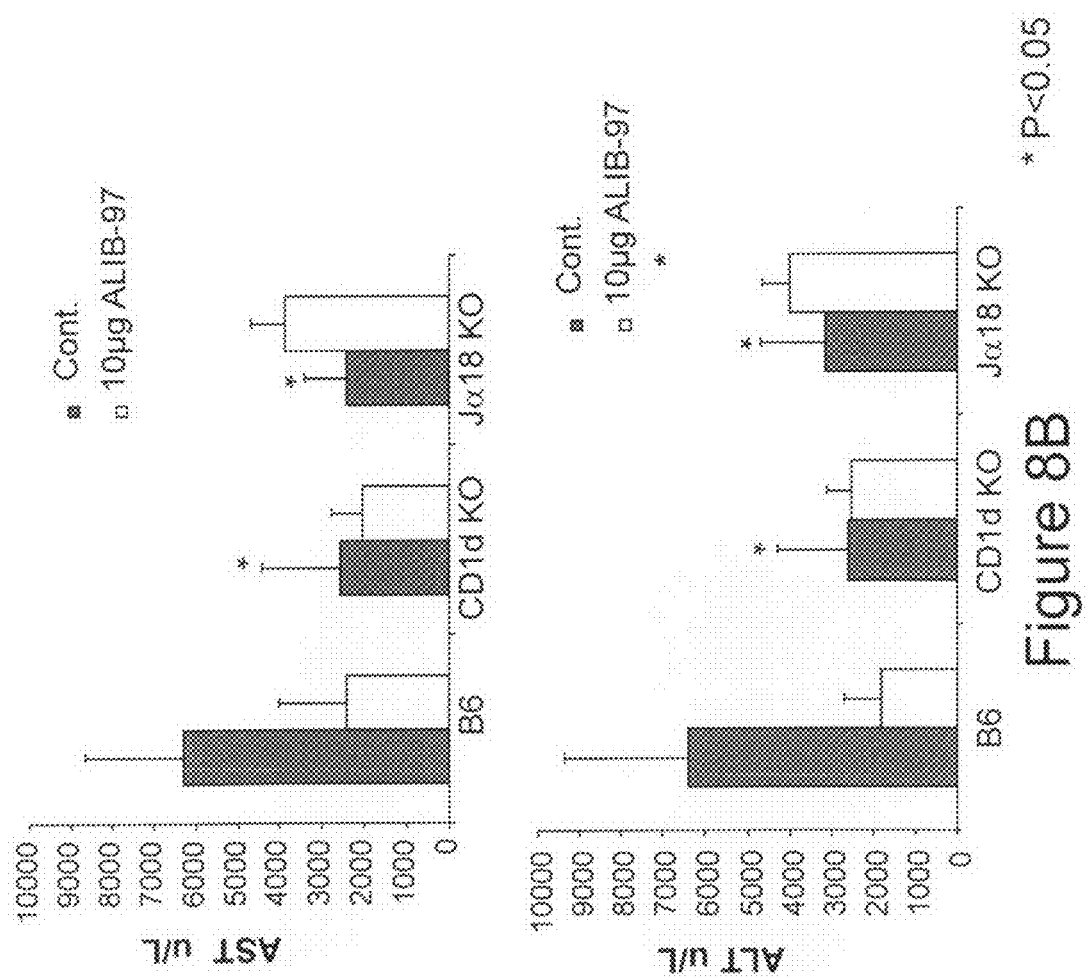
Figure 8C:
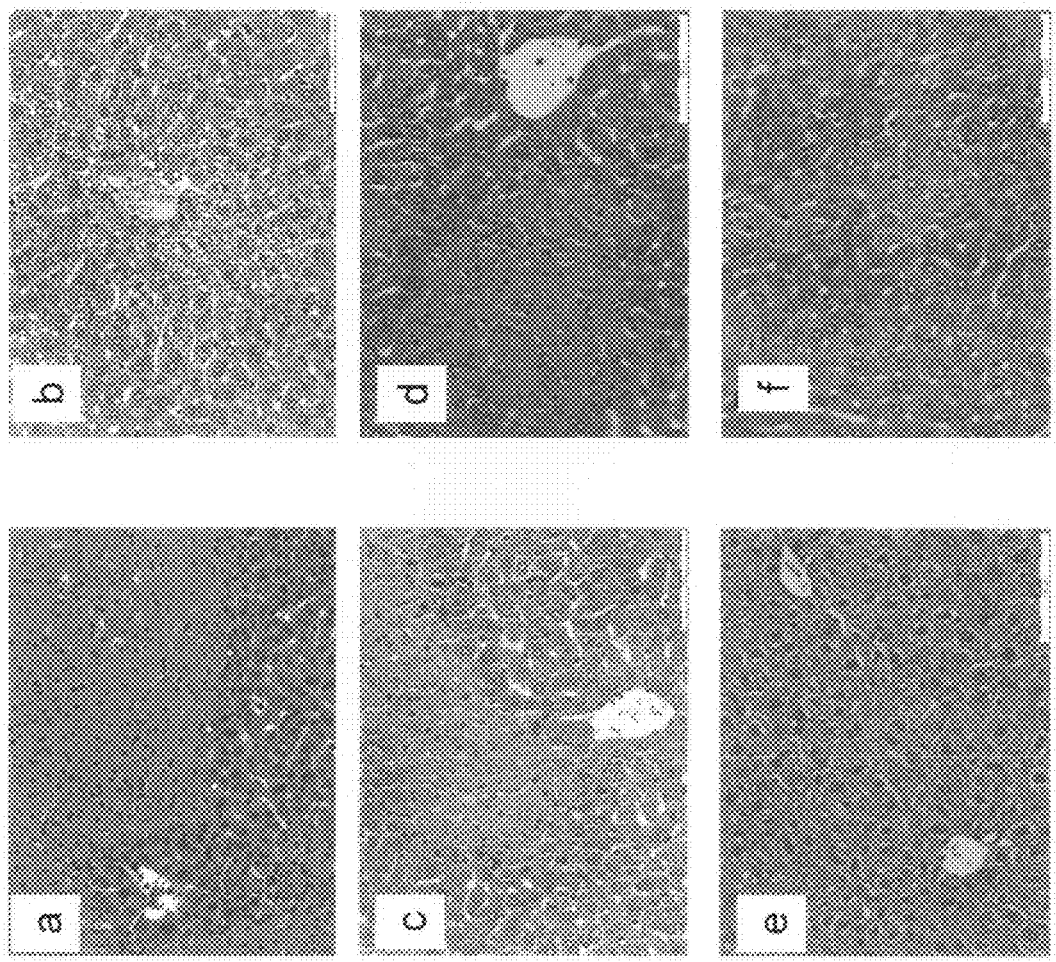

FIG. 8A-8C. Impact of β-glycolipids on induced Con A-mediated liver injury

FIG. 8A. Serum ALT and AST levels in B6 mice treated orally either with vehicle (control), GC, dexamethasone, or ALIB-97.

FIG. 8B. Serum ALT and AST levels in CD1d−/− and Jα18−/− mice treated IP either with vehicle or ALIB-97. N=5 or more animals per group. *$p<0.01$ or 0.05.

FIG. 8C. Representative H&E-stained liver sections of B6, CD1d−/−, and Jα18−/− mice treated IP either with vehicle or ALIB-97. Original magnification, ×200

Abbreviations: cont. (control, vehicle), Dex (dexamethasone).

Figure 9A:
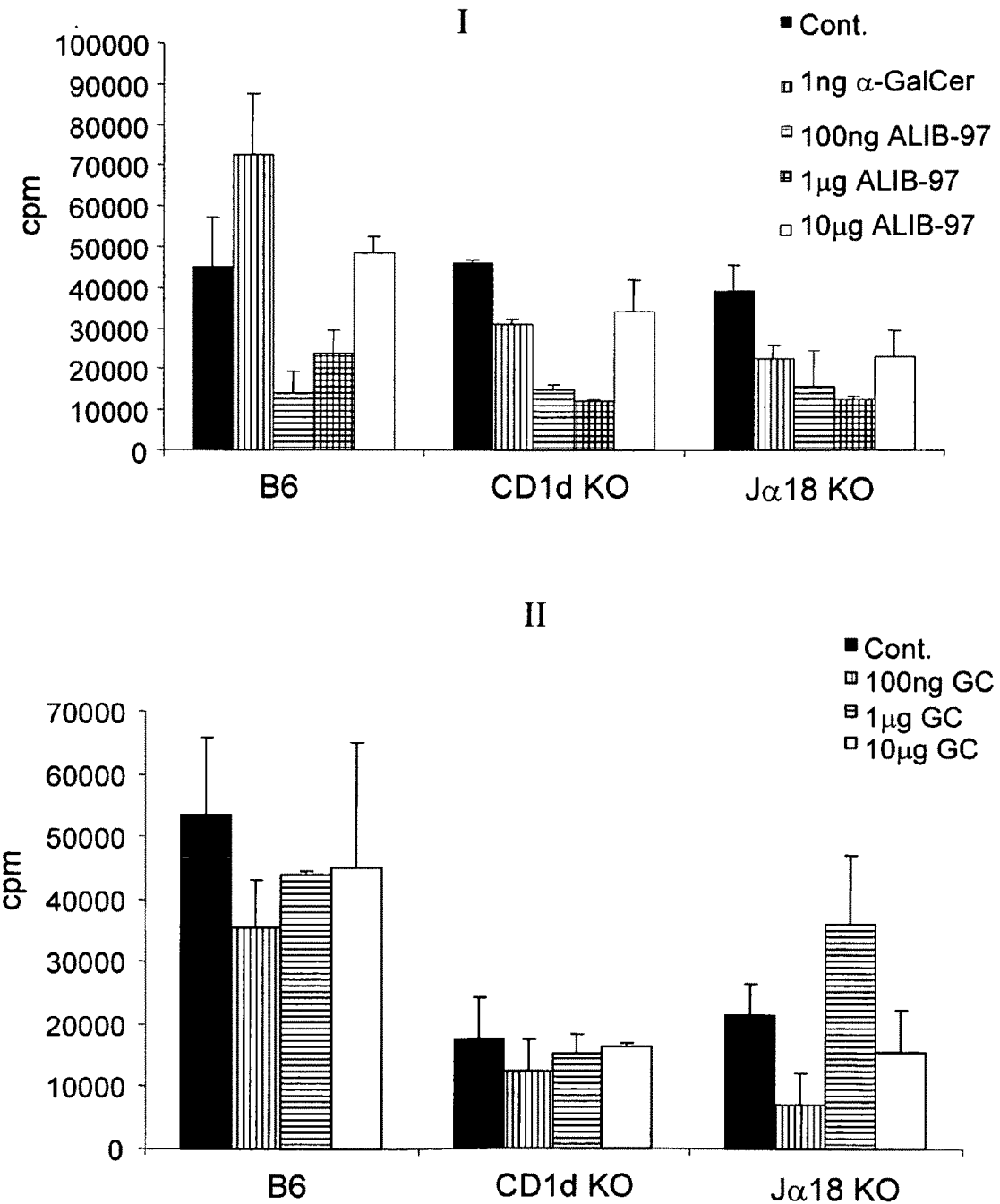
Figure 9B:
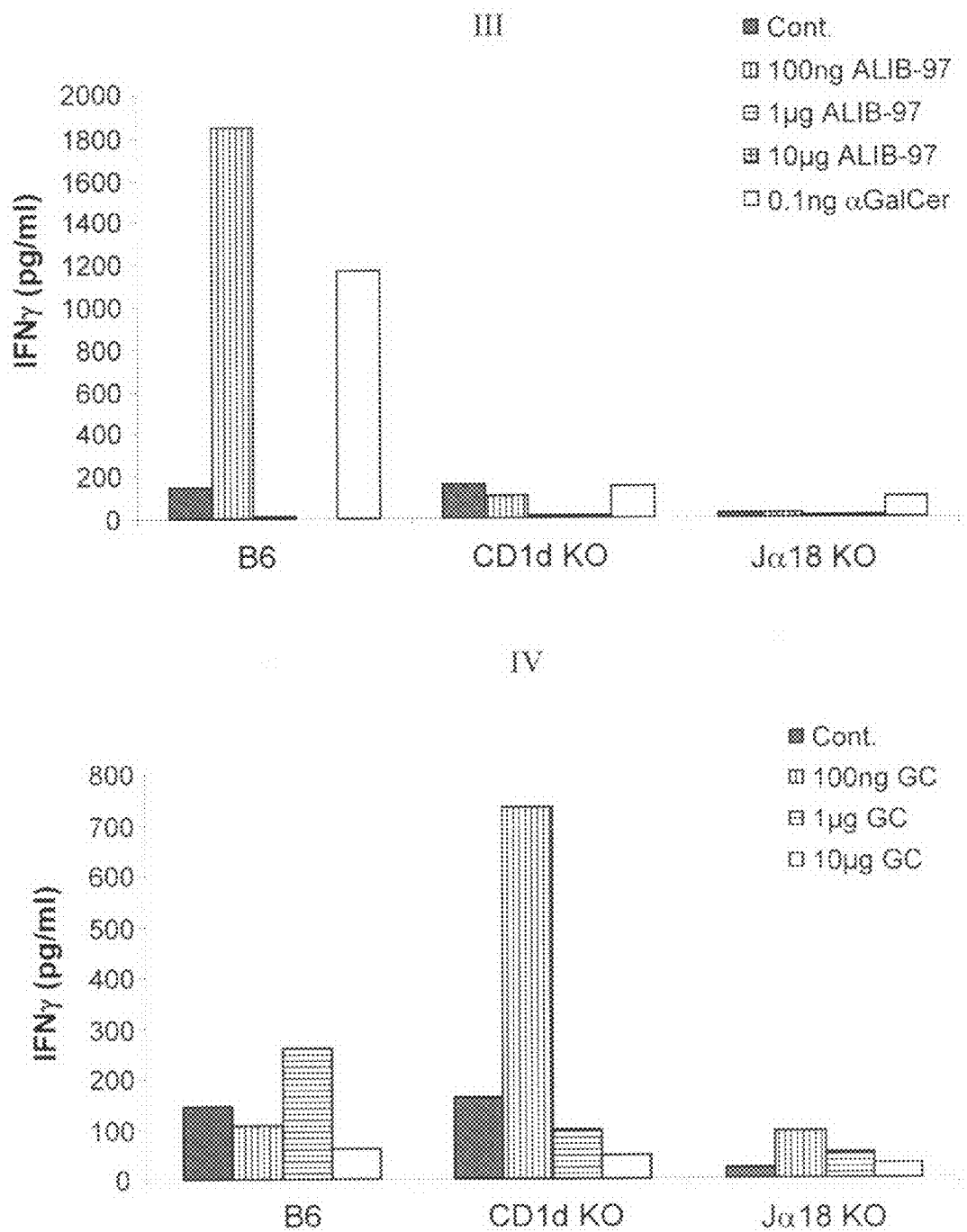

FIG. 9A-9B. Induction of proliferation and IFN-γ response by glycolipids

FIG. 9A. [$^3$H] thymidine incorporation in 72-h splenocyte cultures exposed to graded amounts of β-glycolipid.

FIG. 9B. supernatant IFN-γ levels in 72-h splenocyte cultures exposed to graded amounts of β-glycolipid. α-GalCer served as a control. Means from triplicate cultures are shown.

Abbreviations: cont. (control, vehicle).

Figure 10A:
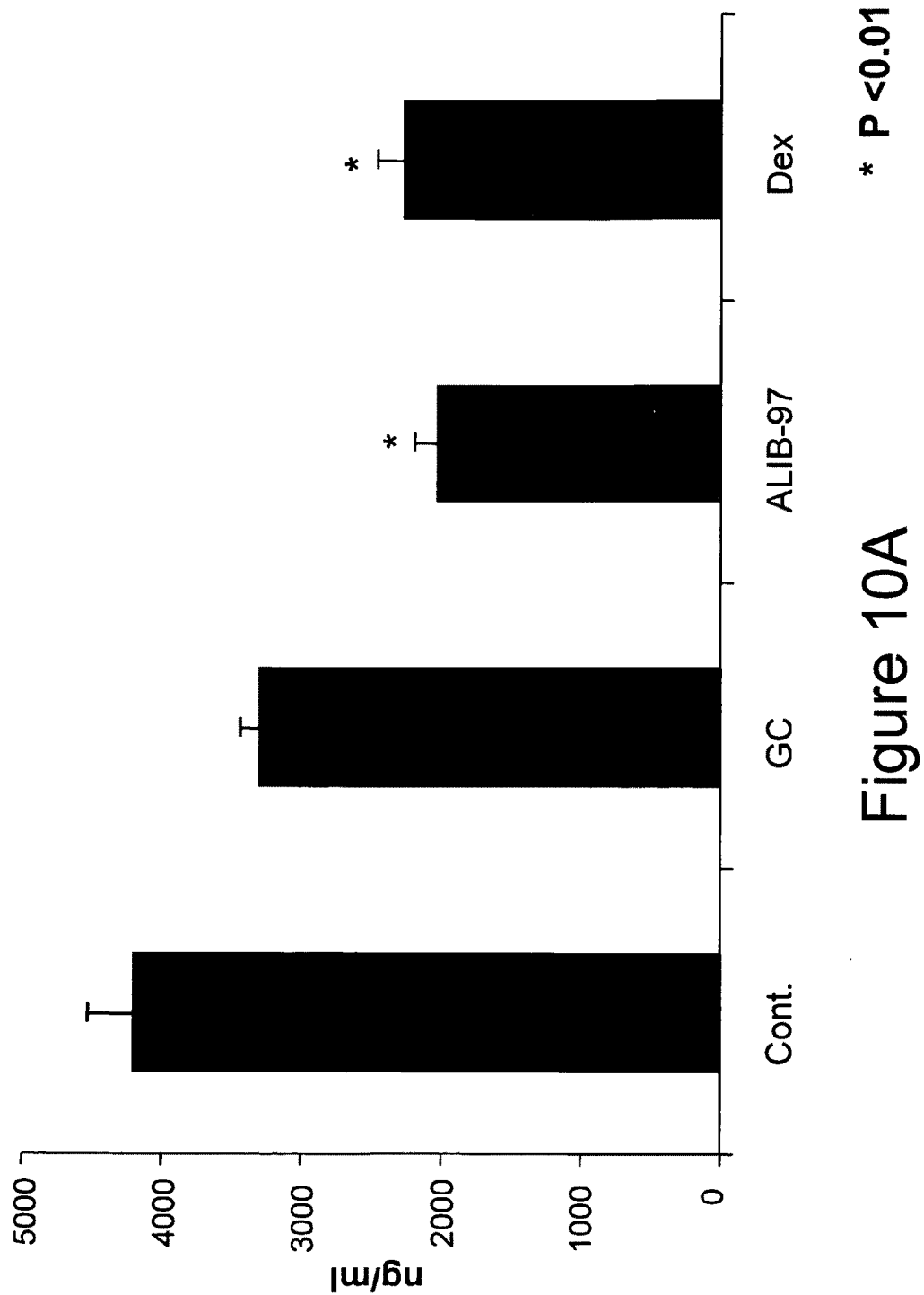
Figure 10B:
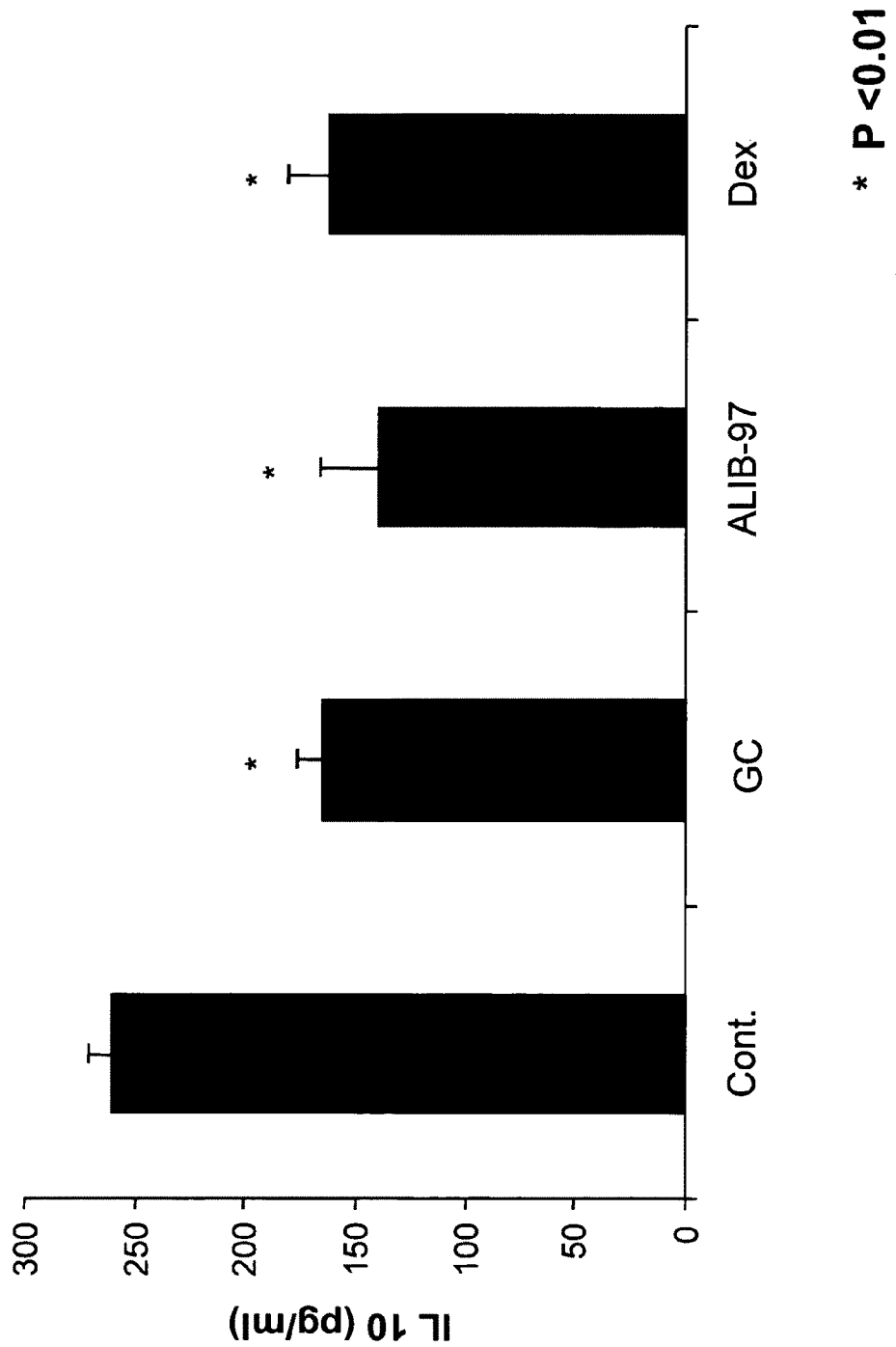
Figure 10C:
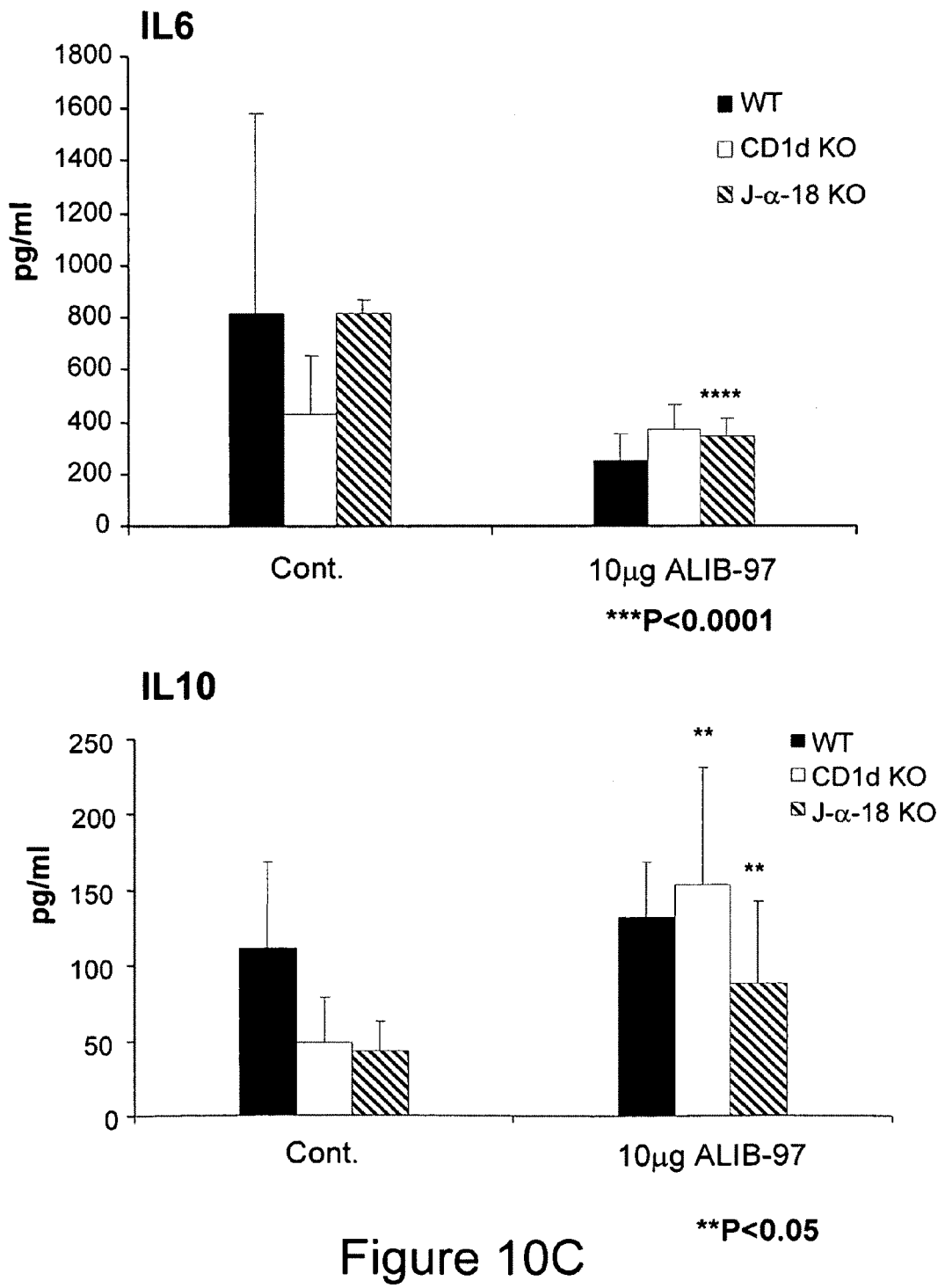
Figure 10C:
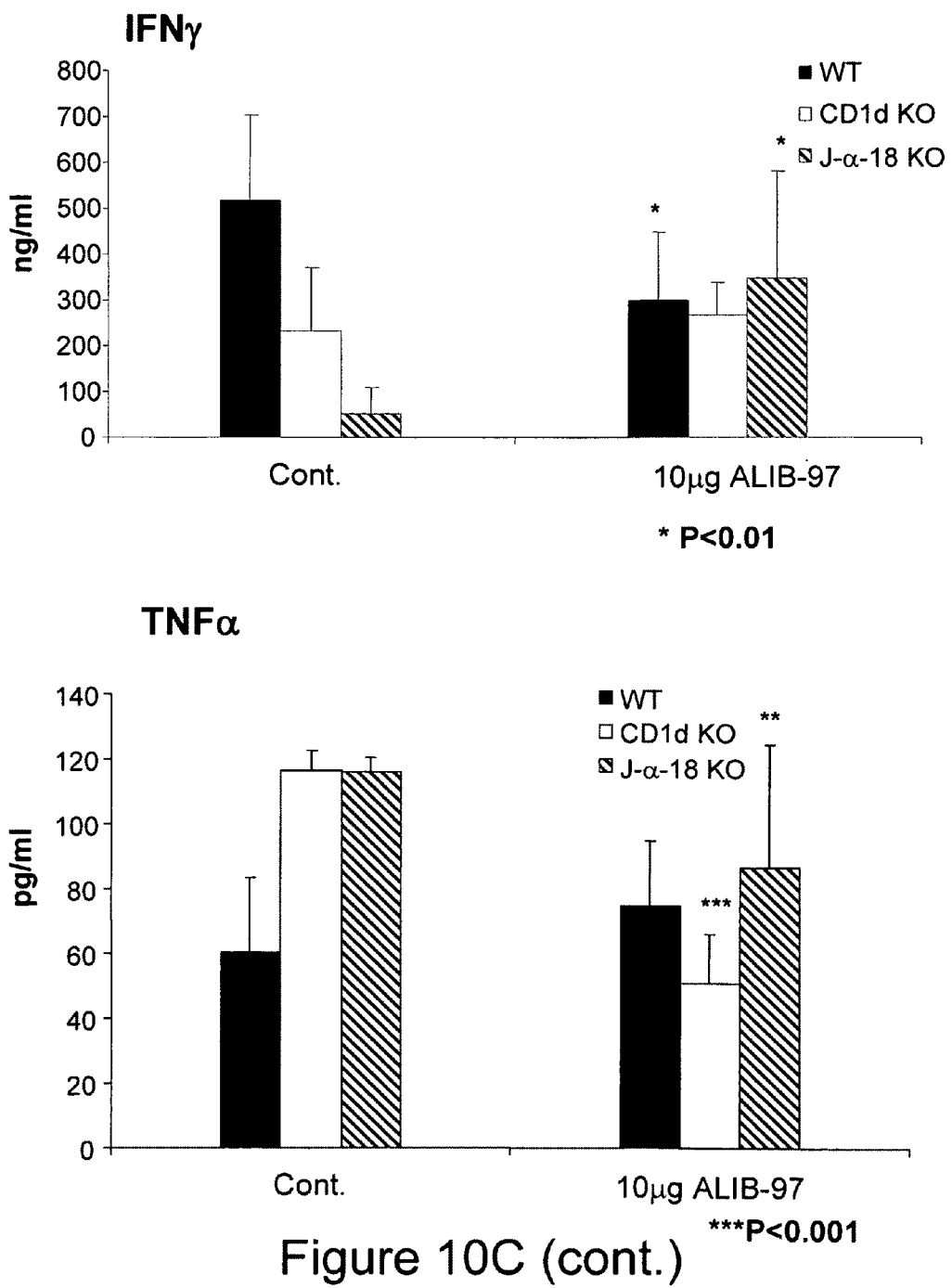

FIG. 10A-10C. Effect of oral ALIB-97 on serum cytokine levels in B6 mice

FIG. 10A. Serum IFN-γ was measured by ELISA. β-glucosylceramide and dexamethasone in comparison to the controls are shown. Means±SD are of five mice per group.

FIG. 10B. Serum IL-10 was measured by ELISA. β-glucosylceramide and dexamethasone in comparison to the controls are shown. Means±SD are of five mice per group.

FIG. 10C. Effect of IP administration of ALIB-97 on serum cytokine levels in WT (B6), CD1d, and Jα18 KO mice. IL-6, IL-10, IFN-γ, and TNF-α in vehicle (control) or ALIB-97-treated mice. Cytokines were measured by ELISA. Means±SD of five mice or more per group are shown.

Abbreviations: cont. (control, vehicle), Dex (dexamethasone), WT (Wild type).

Figure 11A:
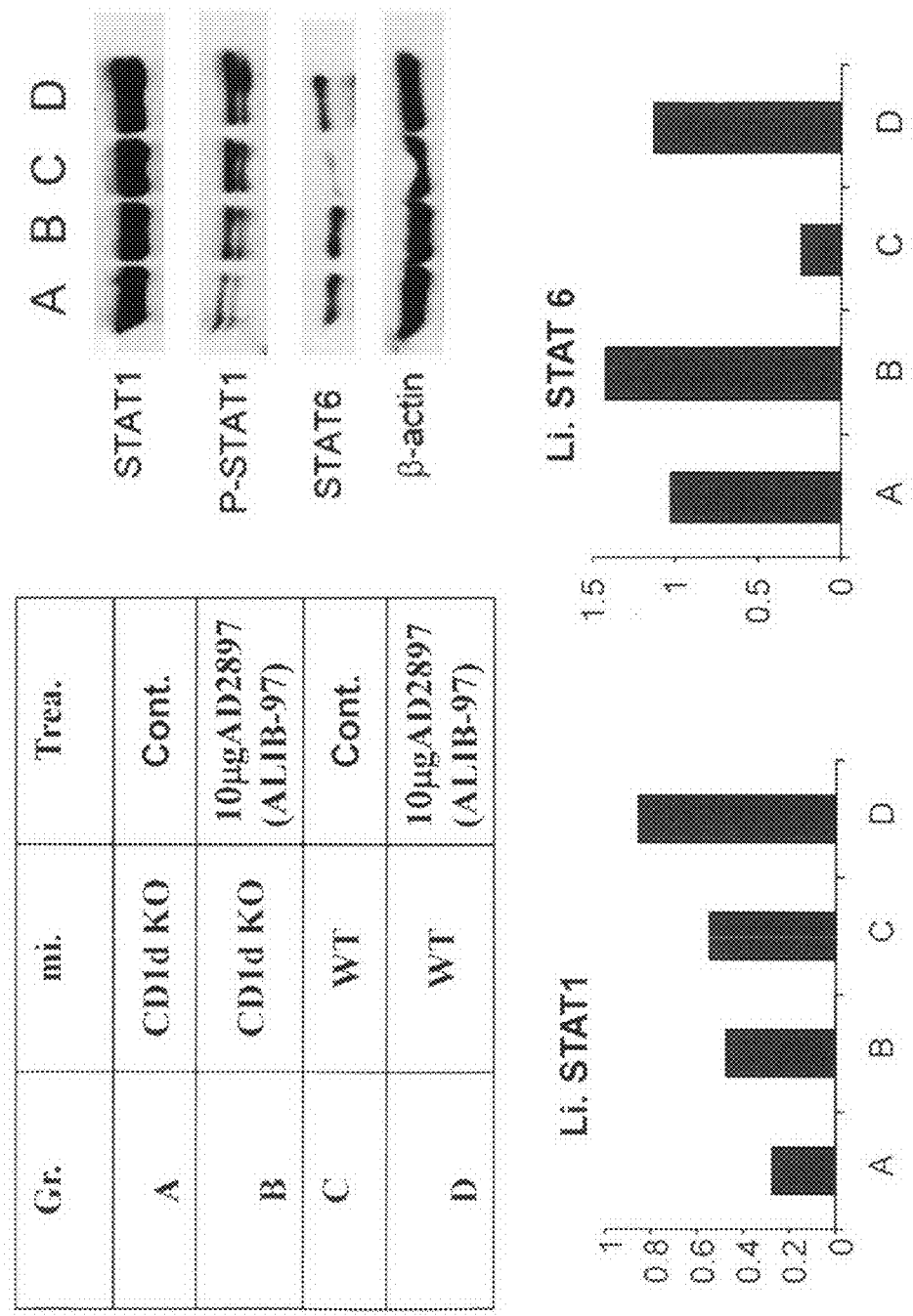
Figure 11B:
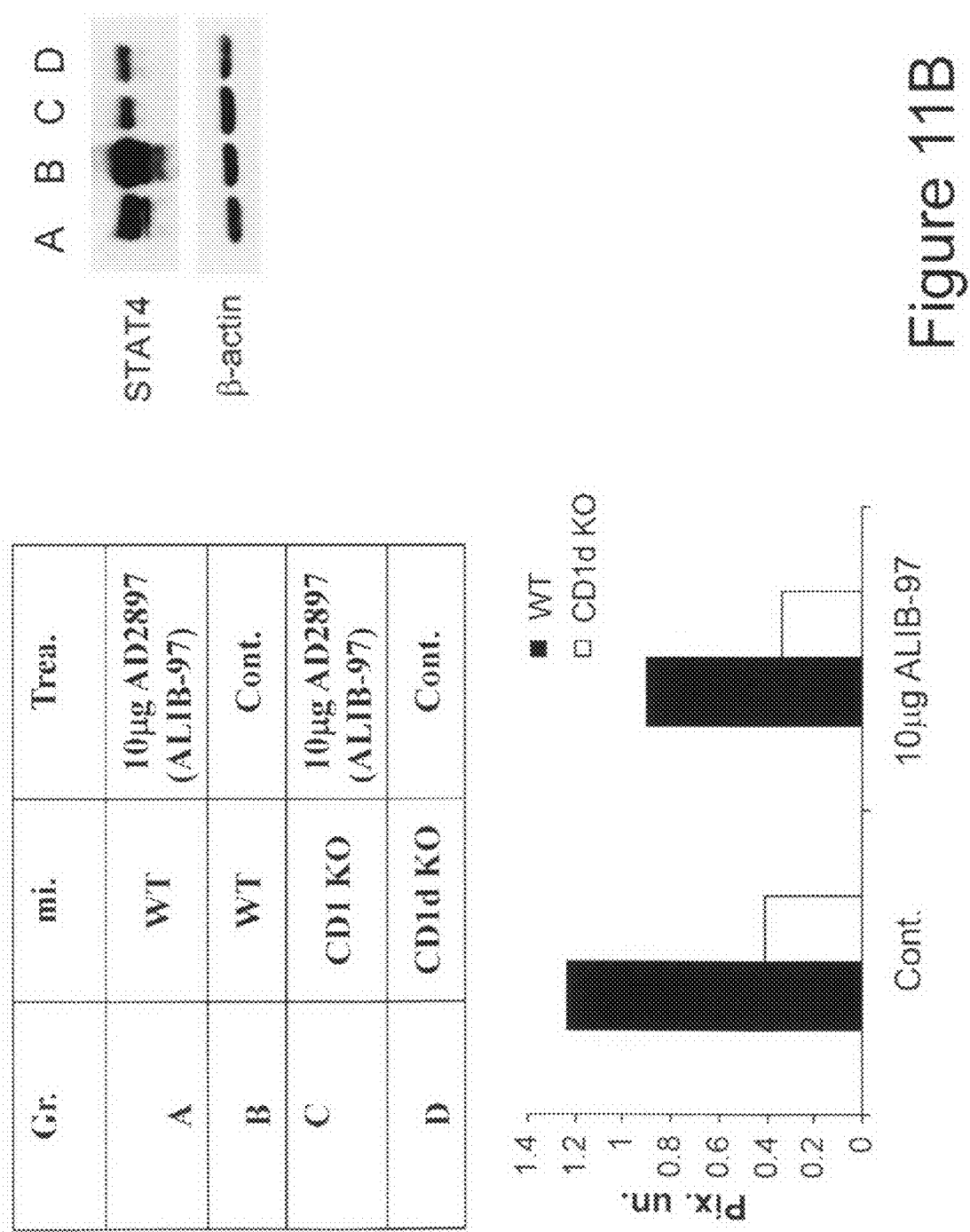

FIG. 11A-11B. Effect of ALIB-97 on STAT proteins activation

FIG. 11A. Immunoblot and densitometry analysis are shown for the effect of ALIB-97 on the phosphorylation of STAT1 and STAT6 in the liver of B6 and CD1d KO mice.

FIG. 11B. Immunoblot and densitometry analysis are shown for the effect of ALIB-97 on the phosphorylation of STAT 4 in the liver of B6 and CD1d KO mice.

Abbreviations: cont. (control, vehicle), Li liver), trea. (treatment), gr. (group).

Figure 12A:
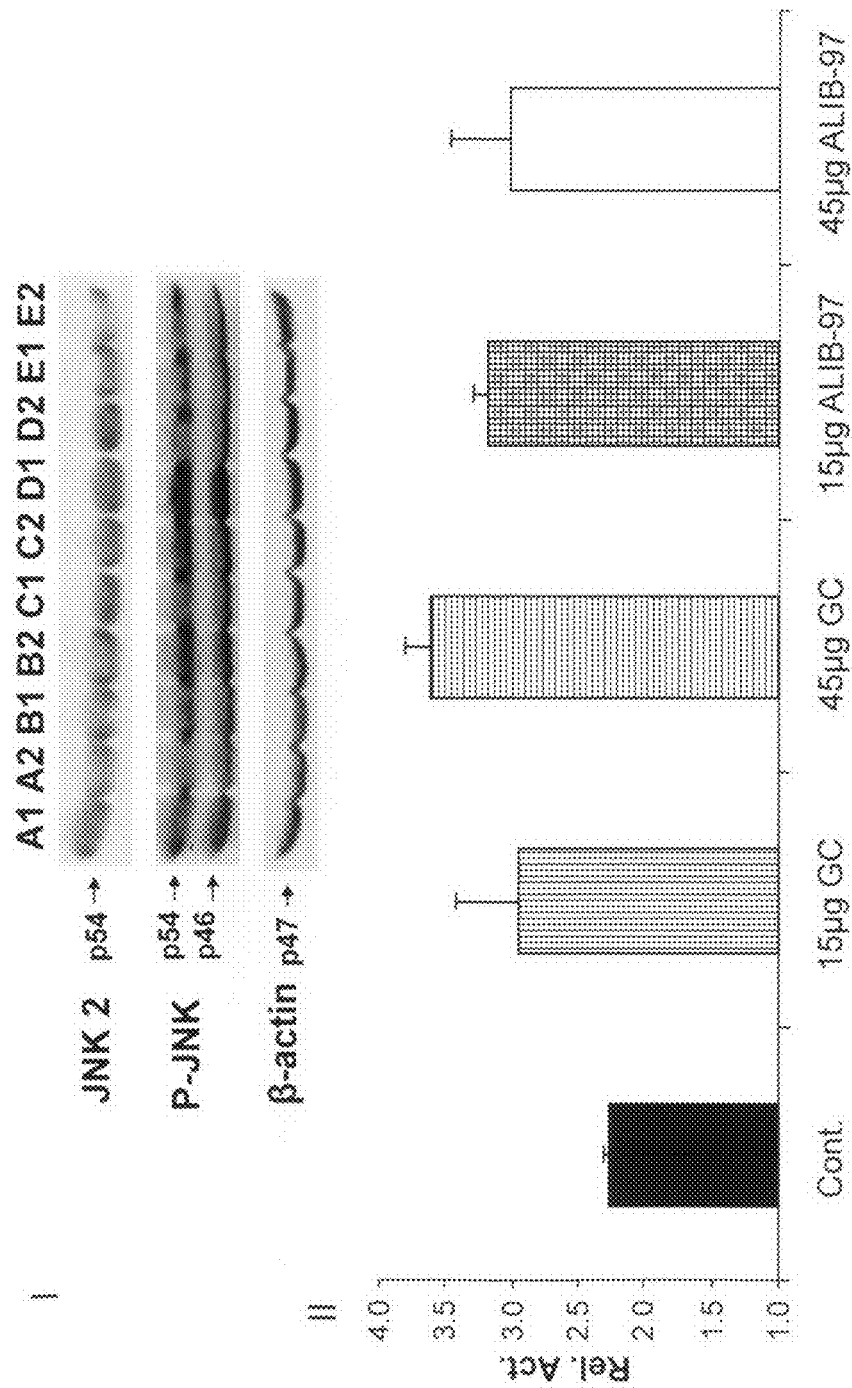
Figure 12B:
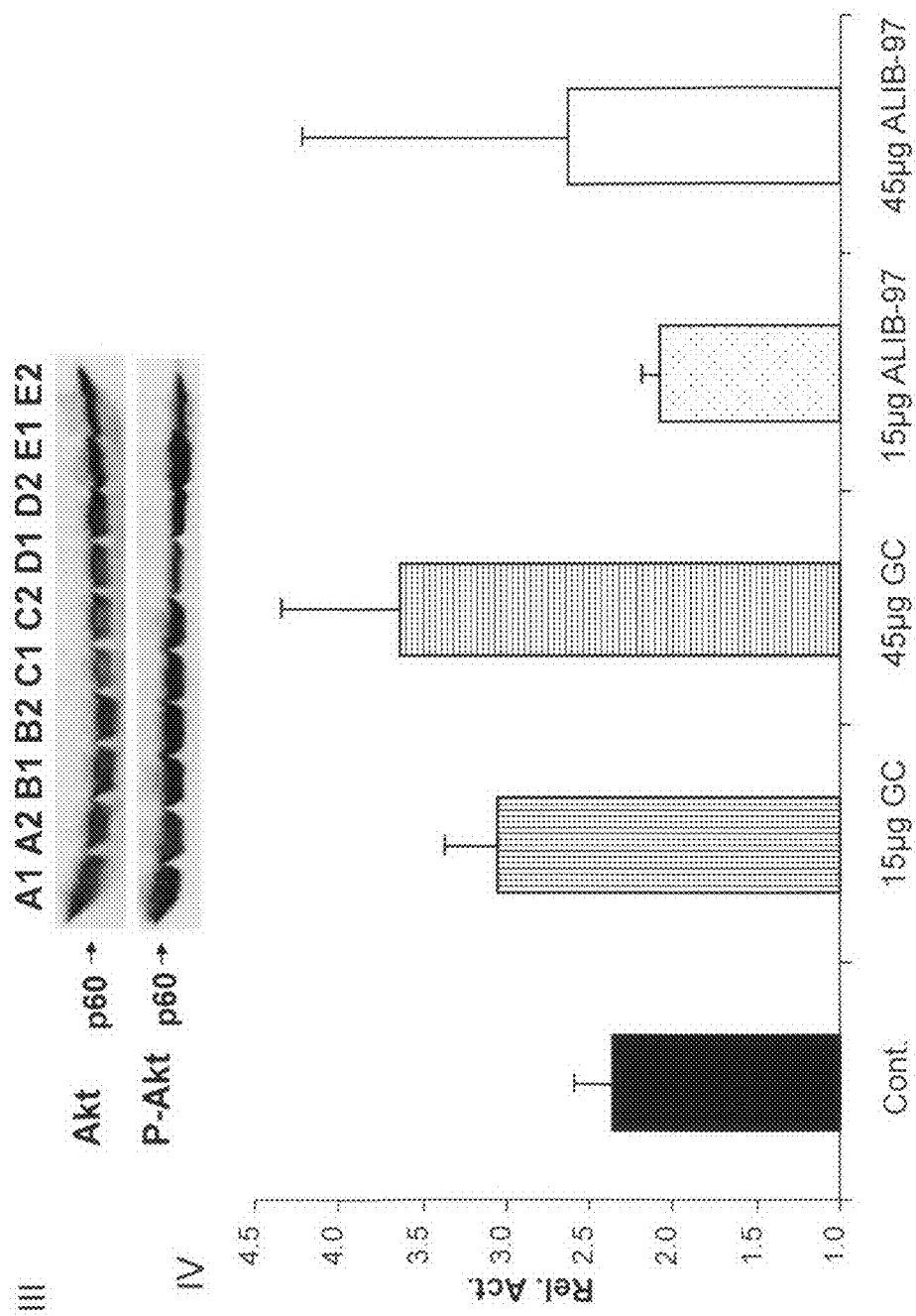

FIG. 12A-12B β-glycolipids increase the phosphorylation of JNK in the liver

FIG. 12A. (I) Western blot of JNK-2 and phospho-JNK (Thr183/Tyr185). About 50 µg of liver extracts from vehicle (A1, A2) or 15 and 45 µg GC-treated mice (B1, B2 and C1, C2, respectively) or 15 and 45 µg ALIB-97-treated mice (D1, D2 and E1, E2, respectively) were electrophoresed on a 12% SDS/PAGE gel, blotted, and probed with antisera specific to JNK, phspho JNK (Thr183/Tyr185) and β-actin. Arrows indicate molecular weights. (II) Quantification of Western blot. The mean results of two extracts are shown.

FIG. 12B. GC but not ALIB-97 increases the phosphorylation of Akt in the liver. (III) Western blot of Akt and phospho-Akt (Ser 473). About 50 μg of liver extracts from vehicle (A1, A2) or 15 and 45 μg GC-treated mice (B1, B2 and C1, C2, respectively) or 15 and 45 μg ALIB-97-treated mice (D1, D2 and E1, E2, respectively) were electrophoresed on a 12% SDS/PAGE gel, blotted, and probed with antisera specific to Akt, phspho Akt (Ser 473). Arrows indicate molecular weights. (IV) Quantification of Western blot. The mean results of two extracts are shown.

Abbreviations: cont. (control, vehicle), rel. act. (relative activity).

Figure 13A:
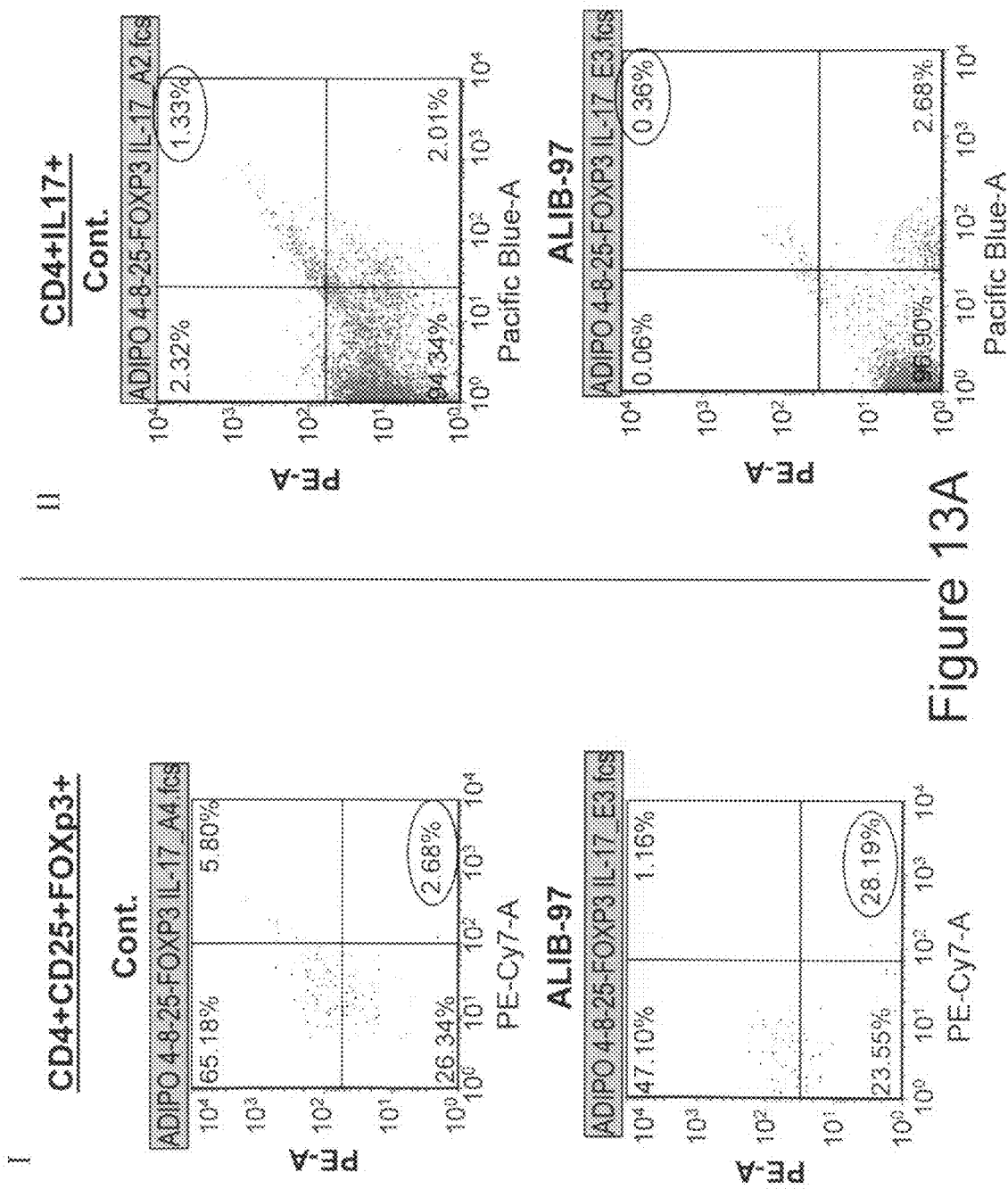
Figure 13B:
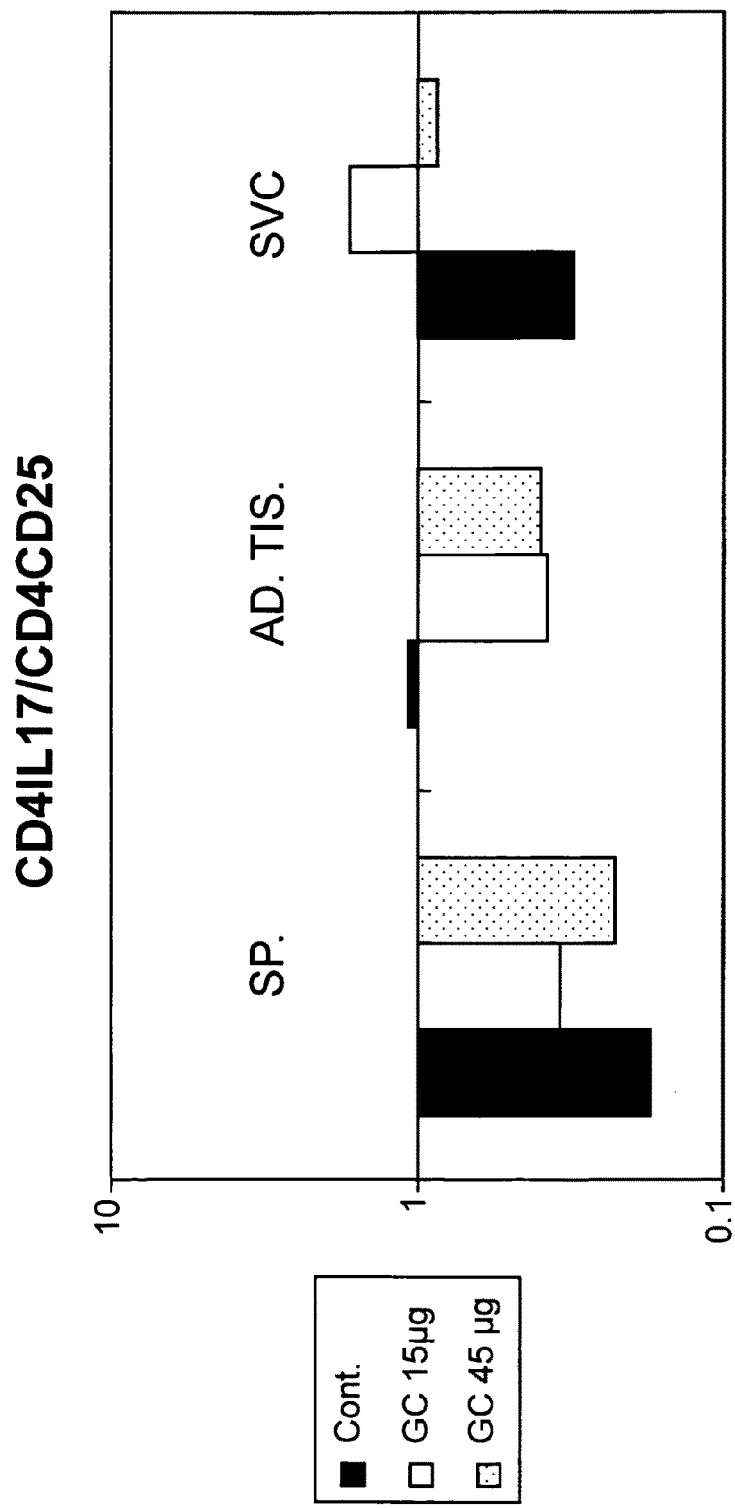
Figure 13C:
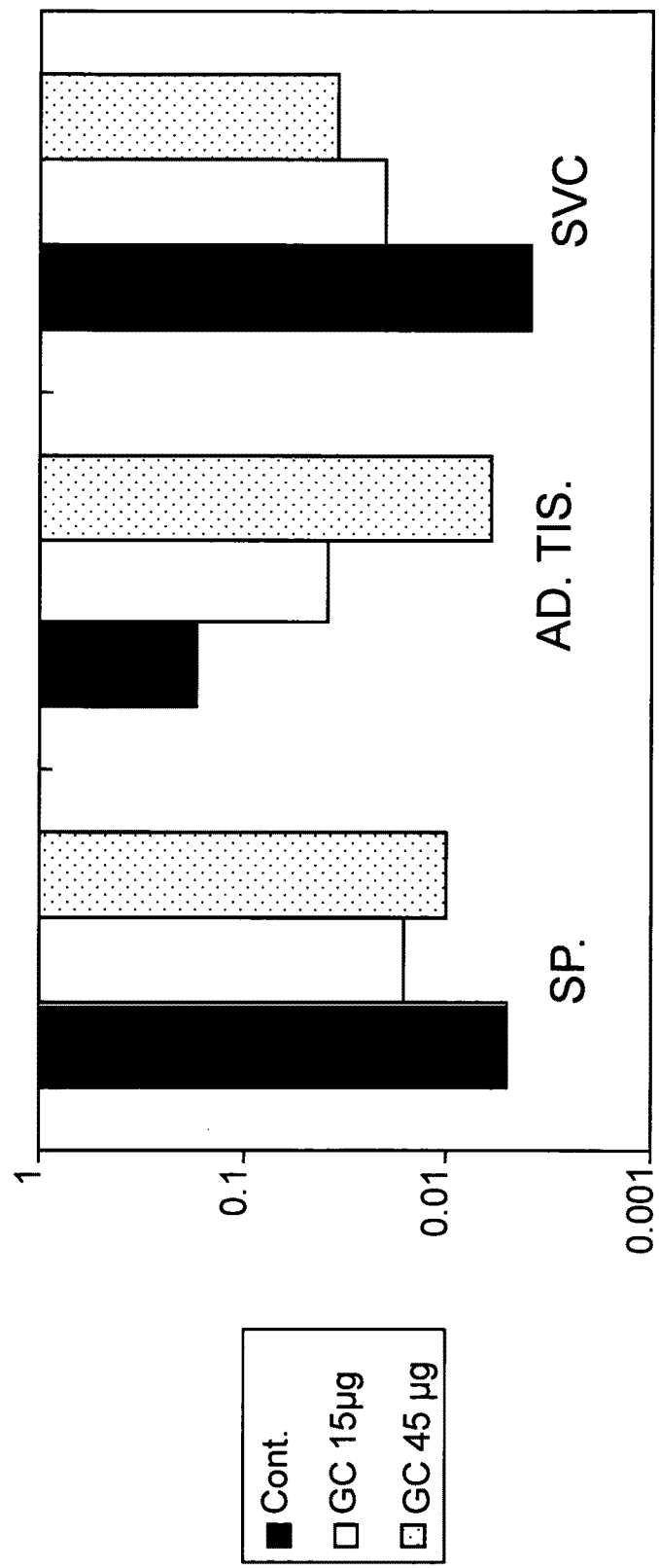

FIG. 13A-13C. ALIB-97 alters subsets of fat-associated T cells from adipose tissue FIG. 13A. Lymphocytes from adipose tissue isolated at day 30 in the control (vehicle) and 45 μg ALIB-97-treated mice. $1 \times 10^6$ cells were analyzed for CD4, CD25 and intracellular FoxP3 (I) or CD4 and IL-17 (II) expression by flow cytometry. Double staining for CD25/FoxP3 or staining for IL-17 expression was performed in gated CD4 T cells. Numbers represent the percentage of cells in each quadrant. N=6 mice/group. Representative dot blots are shown.

FIG. 13B. GC decreases the CD4IL17/CD4CD25 ratio. 15 and 45 μg of GC-treated mice caused a reduction of the CD4IL17/CD4CD25 ratio in adipose tissue and in the spleen.

FIG. 13C. GC decreases the CD4IL17/CD4CD25POXP3 ratio in the spleen and SVC but not in adipose tissue. 15 and 45 μg of GC-treated mice caused a reduction of the CD4IL17/CD4CD25 ratio in the spleen and in the SVC but not in adipose tissue.

Abbreviations: cont. (control, vehicle), sp. (spleen), AD Tis. (adipose tissue).

Figure 14A:
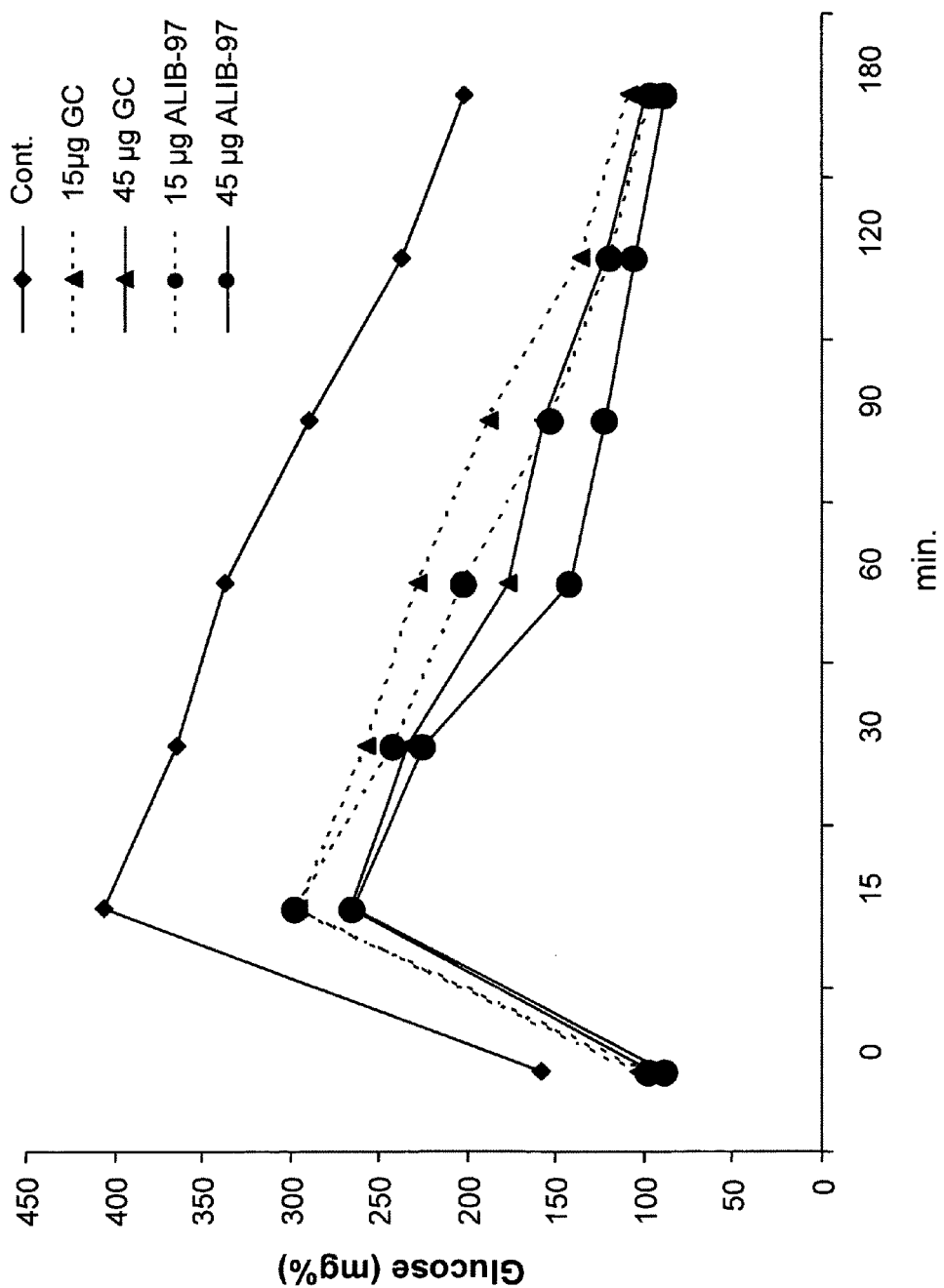
Figure 14B:
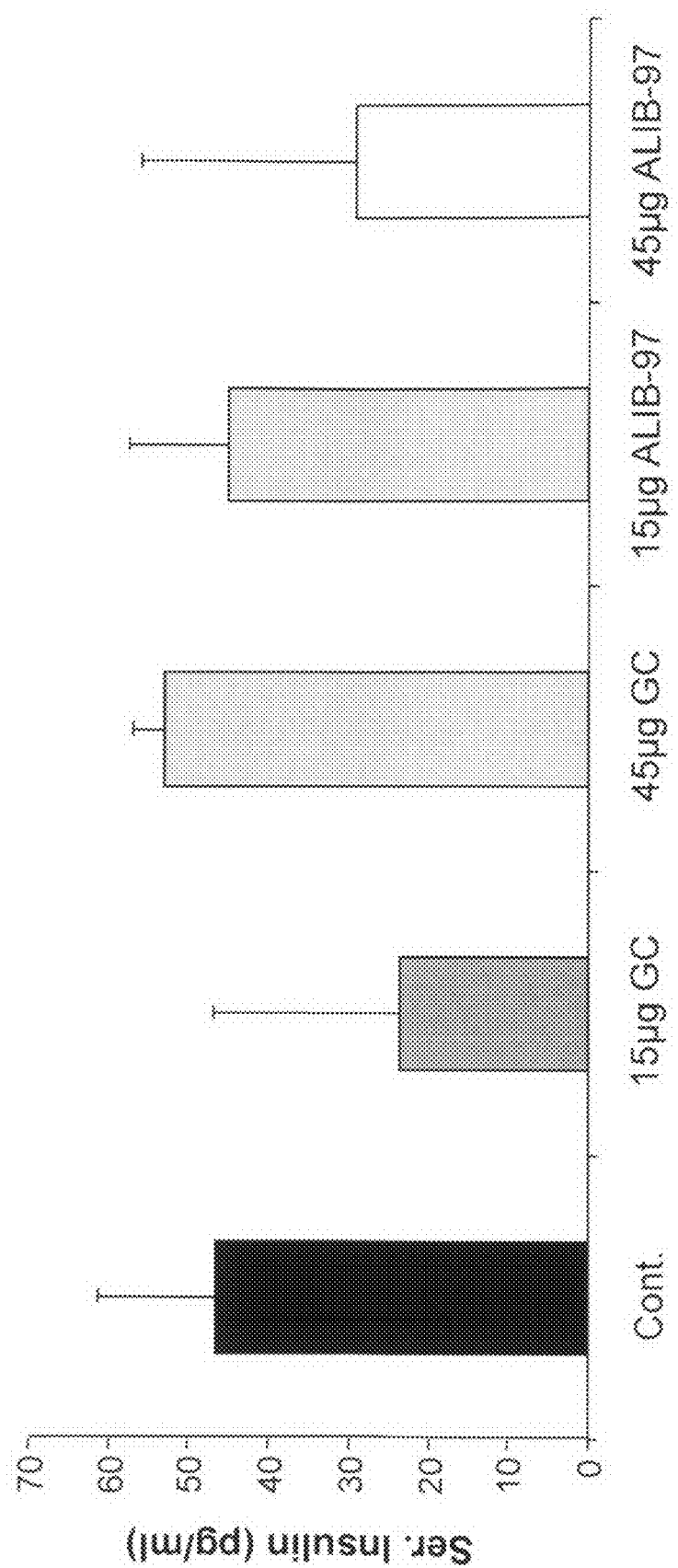

FIG. 14A-14B. β-glycolipids ameliorate the glucose intolerance in ob/ob mice

FIG. 14A. Glucose tolerance test (GTT) was performed on day 30 after overnight fasting. Glucose was administered orally (1.25 g per kg). Serum glucose measurements were performed on tail-vein blood every 15 min for 3 h. Glucose levels were measured by a standard glucometer.

FIG. 14B. The effect of β-glycolipids on serum insulin levels. ELISA was performed on sera derived from ob/ob mice in day 30.

Abbreviations: cont (control, vehicle), min. (minute).

Figure 15:
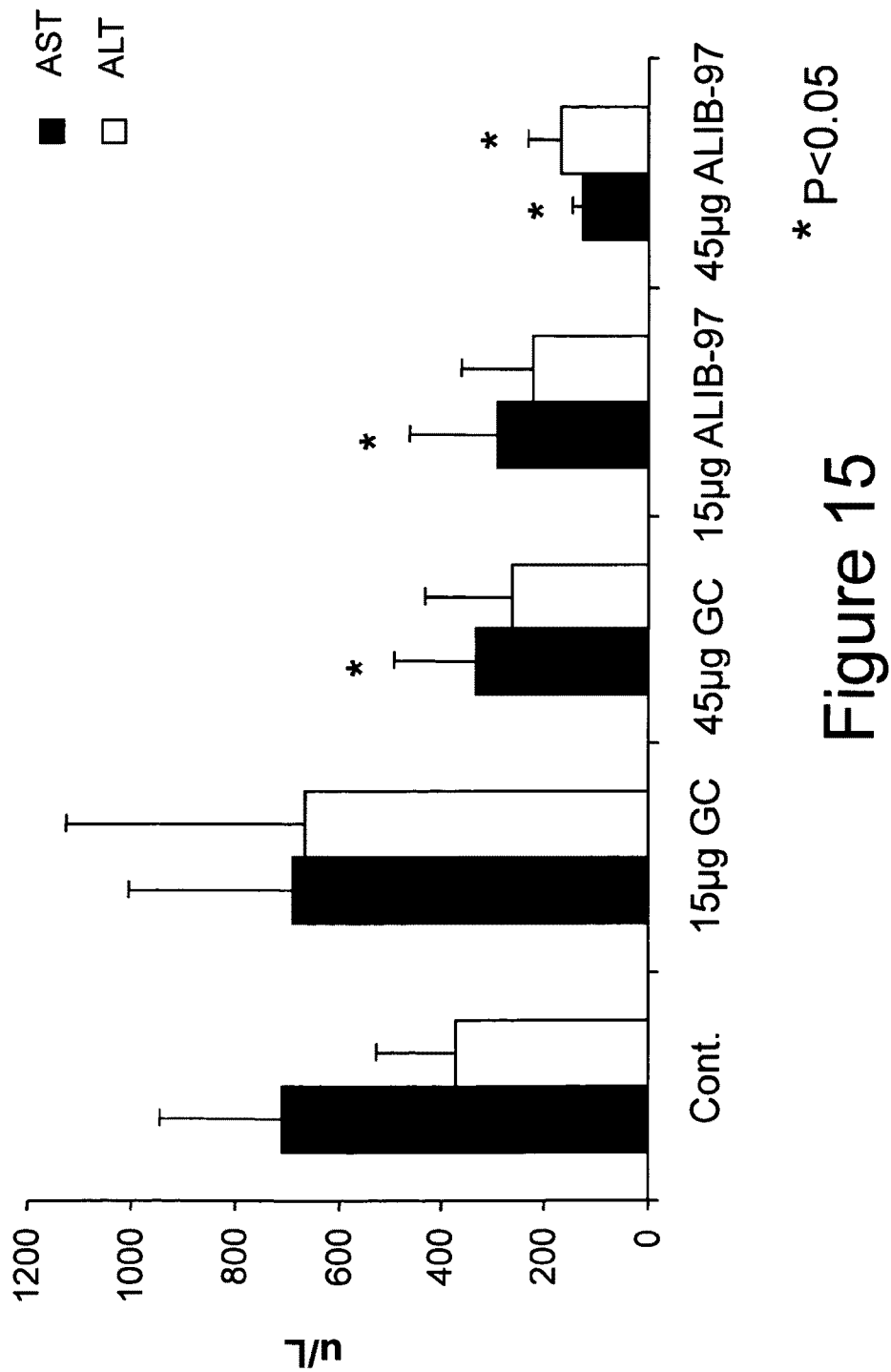

FIG. 15. ALIB-97 decreases hepatic injury

The levels of liver enzymes were determined by ALT and AST serum levels in day 30. *P<0.05

Abbreviations: cont (control, vehicle).

Figure 16:
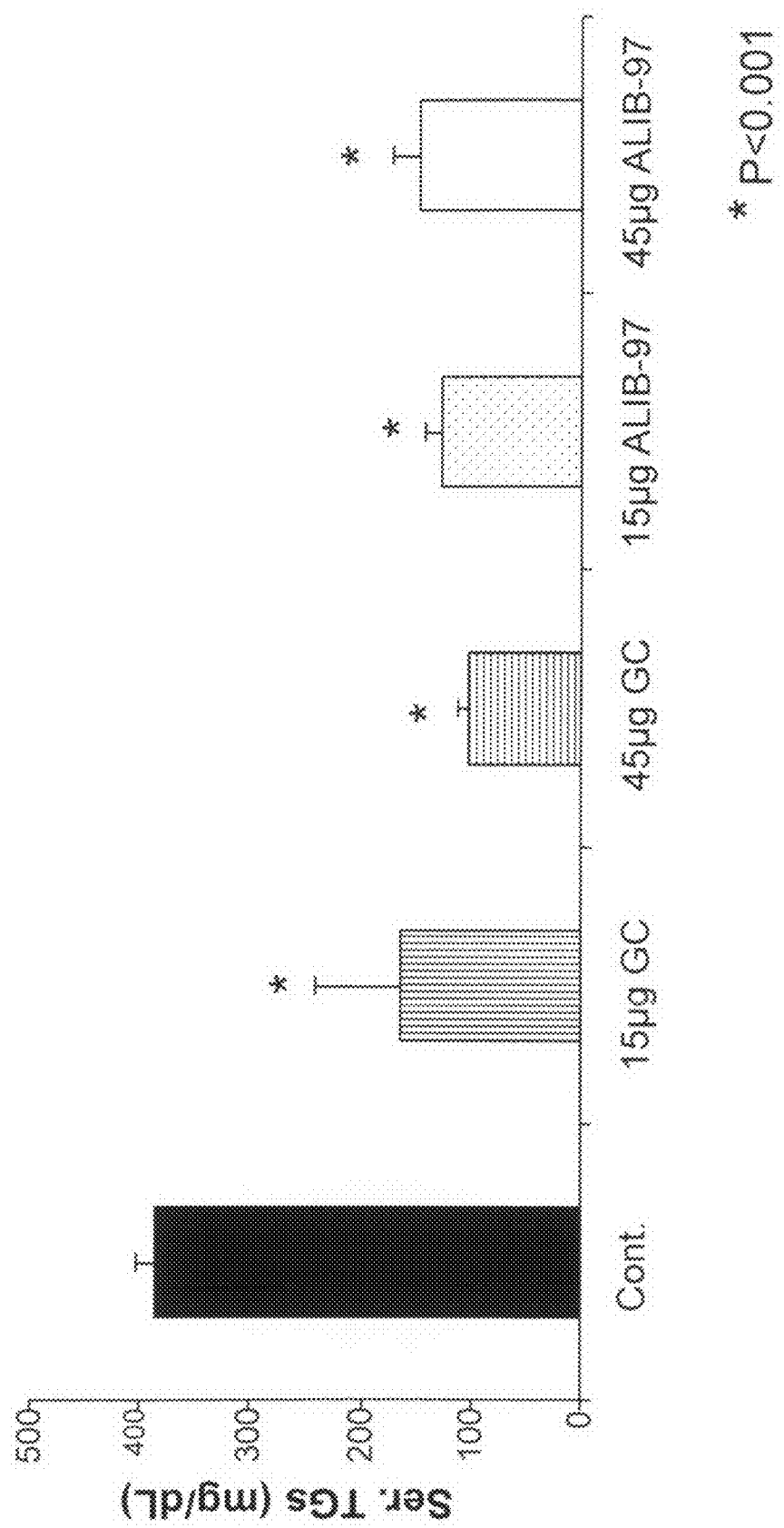

FIG. 16. β-glycolipids ameliorate the serum triglyceride levels

Serum TGs levels were determined on day 30/*P<0.01

Abbreviations: cont (control, vehicle), ser. (serum), TG (triglycerides)

DETAILED DESCRIPTION OF THE INVENTION

The present invention provide novel analogs of β-glycolipids and demonstrate their use as immuno-modulating agents, particularly in immune mediated hepatitis and metabolic syndrome associated disorders.

Thus, in a first aspect, the invention relates to synthetic derivatives or analog of β-glycolipids, more particularly, the invention relates to a compound of Formula I, or isomer thereof or a pharmaceutically acceptable salt thereof:

$$\begin{array}{c} \text{OH—CH-A—R}_1 \\ | \\ \text{CH—NH-D—R}_2 \\ | \\ \text{CH}_2\text{—O-E} \end{array} \quad \text{(I)}$$

wherein

A represents alkenylene or alkylene bivalent radical selected from —CH=CH— and —CH(OH)—CH$_2$—;

D represents a bivalent radical selected from —CSNH—, —CONH—, —CS—, and —SO$_2$—;

E represents a glycosyl radical selected from glucosyl, galactosyl, sulfated galactosyl, manosyl, and lactosyl;

R$_1$ is a linear C$_{8-21}$alkyl; and

R$_2$ is a univalent radical selected from linear or branched alkyl or alkenyl chains optionally substituted with hydroxyl, adamantanyl, and norbornenyl.

According to one embodiment, the compound of the invention may be the compound of Formula II, also designated as AD2897 and as ALIB-97, or isomer thereof or a pharmaceutically acceptable salt thereof.

(II)

According to another embodiment, the compound of the invention may be the compound of Formula III, also designated as AD2898, or a pharmaceutically acceptable salt thereof.

(III)

In a further preferred embodiment, the compound of the invention may be the compound of Formula IV, also designated as AD2899, or a pharmaceutically acceptable salt thereof.

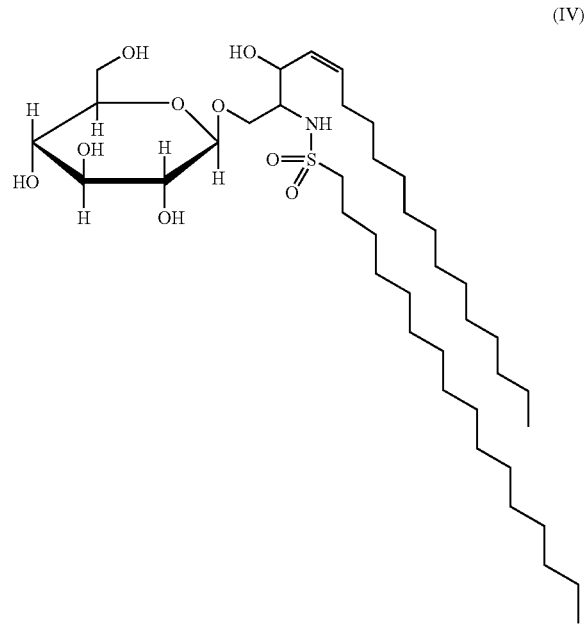

(IV)

As indicated above, the invention relates to the compounds of Formulas I, II, III and IV, which are provided by the specific synthetic derivatives of β-glycolipids. As indicated throughout the application, β-glycolipid or a natural β-glycolipid is meant any compound selected from the group consisting of a monosaccharide ceramide, a glucosylceramide, a galatosylceremide, a lactosyl-ceramide, a gal-gal-glucosyl-ceramide, GM2 ganglioside, GM3 ganglioside, globoside or any other β-glycolipid.

According to another aspect, the invention provides a composition comprising the compound of at least one of the compounds of Formula I, Formula II, Formula III, Formula IV, or any mixtures or combinations thereof. The composition of the invention may further comprise at least one of a pharmaceutically acceptable carrier, diluent, excipient and/or additive.

In one embodiment, the invention relates to a composition comprising the compound of Formula I. The composition of the invention may further comprise at least one of a pharmaceutically acceptable carrier, diluent, excipient and/or additive.

In one particular embodiment, the composition of the invention comprises as an active ingredient the compound of Formula II, also referred to as AD2897 and as ALIB-97. The composition of the invention may optionally further comprises at least one of a pharmaceutically acceptable carrier, diluent, excipient and/or additive.

According to another embodiment, the composition of the invention comprises as an active ingredient the compound of Formula III, also referred to as AD2898. It should be noted that the composition of the invention may further comprises at least one of a pharmaceutically acceptable carrier, diluent, excipient and/or additive.

In yet another embodiment, the composition of the invention comprises as an active ingredient the compound of Formula IV, also referred to as AD2899. The composition of the invention may further comprise at least one of a pharmaceutically acceptable carrier, diluent, excipient and/or additive.

Thus, the invention provides a composition comprising as an active ingredient at least one of the compounds as defined by the invention or a mixture of at least two compounds being selected from the compounds of Formula I, II, III, IV, and other synthetic or natural β-glycolipid derivatives. The composition of the invention may optionally further comprises at least one of a pharmaceutically acceptable carrier, diluent, excipient and/or additive.

According to a third aspect, the invention relates to a therapeutic composition for treating, preventing, ameliorating or delaying the onset of a pathologic disorder in a mammalian subject. More particularly, the therapeutic composition of the invention may comprise as an active ingredient any one of: (a) at least one of the compounds of Formula I, II, III or IV; (b) a mixture of at least two compounds of Formula I, II, III or IV; (c) at least one component of said subject's immune-system which was pre-exposed to an effective amount of any one of the compounds of said Formula I, II, III or IV, or to any mixture or any combination thereof; and (d) any combinations of (a), (b) and (c). It should be noted that the therapeutic composition of the invention may optionally further comprises at least one of a pharmaceutically acceptable carrier, diluent, excipient and/or additive.

According to a specific embodiment, any of the compounds of Formula I, II, III or IV, comprised as an active ingredient in the therapeutic and immunomodulatory compositions of the invention are as defined by the invention.

According to one particular embodiment, the invention provides an immuno-modulatory therapeutic composition comprising as an active ingredient the compound of Formula II (ALIB-97), for the treatment of immune-related disorders.

According to certain embodiments, the therapeutic and immunomodulatory compositions of the invention may comprises a mixture of at least two of the compounds of Formula I, II, III or IV, or at least one of the compounds of Formula I, II, III or IV and any other synthetic or natural β-glycolipid derivatives at a quantitative ratio between 1:1 to 1:1000.

It should be appreciated that any quantitative ratio may be used. As a non-limiting example, a quantitative ratio used may be: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1500, 1:750, 1:1000. It should be further noted that where the mixture of the invention comprises more than two synthetic derivatives of β-glycolipids, the quantitative ratio used may be for example, 1:1:1, 1:2:3, 1:10:100, 1:10:100:1000 etc.

In another specific embodiment, the mixture of said compounds may comprise the compound of Formula I and at least one of the compounds of any one of Formula II, III, IV, or any other synthetic or natural derivative of β-glycolipid, at a quantitative ratio between 1:1 to 1:1000.

Another specific embodiment relates to a mixture of said compounds which specifically comprises the compound of Formula II (ALIB-97) and at least one of the compounds of any one of Formula I, III, IV, or any other synthetic or natural derivative of β-glycolipid, at a quantitative ratio between about 1:1 to 1:1000.

In yet another specific embodiment, the mixture of said compounds comprises the compound of Formula III and at least one of the compounds of any one of Formula I, II, IV or any other synthetic or natural derivative of β-glycolipid, at a quantitative ratio between about 1:1 to 1:1000.

Another specific embodiment relates to a mixture of said compounds which specifically comprises the compound of Formula IV and at least one of the compounds of any one of Formula I, II, III, or any other synthetic or natural derivative of β-glycolipid, at a quantitative ratio between about 1:1 to 1:1000.

According to certain embodiments, the therapeutic and the immunomodulatory compositions of the invention are particularly intended for the treatment of a pathologic disorder such as an immune-related disorder and a neurodegenerative disorder.

Thus, according to one embodiment, the therapeutic composition of the invention may be an immunomodulatory composition particularly applicable in modulating the Th1/Th2, Th3 cell balance in a subject suffering from an immune-related disorder. Such immuno-modulation may activate or inhibit an immune response specifically directed toward said disorder in the treated subject.

According to one specific embodiment, the therapeutic composition of the invention may modulate the Th1/Th2, Th3 cell balance toward an anti-inflammatory Th2, Tr1/Th3 immune response in a subject suffering from an immune-related disorder. Modulation of the Th1/Th2, Th3 balance towards an anti-inflammatory Th2, Tr1/Th3 response may be particularly applicable in immune related disorders having an undesired unbalanced pro-inflammatory Th1 reaction.

According to certain embodiments, such therapeutic composition may be used in treating immune related disorder such as any one of Metabolic Syndrome or any of the conditions comprising the same, Non-alcoholic fatty liver disease (NAFLD), non-alcoholic steatohepatitis (NASH), immune mediated hepatitis, an autoimmune disease, graft rejection pathology, inflammatory disease, hyperlipidemia, atherosclerosis and a neurodegenerative disorder.

The invention describes the use of the ALIB-97 derivative in treating certain immune-related disorders. Thus, according to one specific embodiment, the invention provides a therapeutic composition comprising the compound of Formula II (ALIB-97) and any mixtures and combinations thereof.

Obesity and its associated metabolic syndromes represent a growing global challenge, yet mechanistic understanding of this pathology and current therapeutics are unsatisfactory. The present invention show that induction of CD4+ T regulatory cells resident in visceral adipose tissue (VAT), can control insulin resistance in leptin deficient mice and lead to decrease in activation of JNK2. Analyses of human tissue suggest that a similar process may also occur in humans. Recently, it has been reported that in obese WT and ob/ob (leptin deficient) mice, brief treatment with CD3-specific antibody or its F(ab)2 fragment, reduces the predominance of Th1 cells over Foxp3+ cells, reversing insulin resistance for months, despite continuation of a high-fat diet [Winer, 2009].

In that study Winer and colleagues suggest that the progression of obesity-associated metabolic abnormalities is under the pathophysiological control of CD4+ T cells.

Example 4 shows that induction of CD4+ T regulatory cells in adipose tissue and in the adipose tissue-associated stromal vasculature by the novel β-glycolipid analog of the invention is associated with the activation of JNK2 and alleviation of insulin resistance and hepatic injury. The data of the present invention supports an active role for the adipose tissue and inflammatory processes in the pathogenesis of insulin resistance. In general, expansion of CD4+ T regulatory cells (CD4+CD25+FOXP3+) was associated with alleviation of the metabolic syndrome in terms of gluconeogenesis (reduced fasting glucose), insulin resistance (reduced postprandial glucose levels), reduced hepatic injury (AST and ALT serum levels), Tregs levels and increased JNK2 and AKT activation.

Thus, according to one embodiment, the therapeutic composition of the invention may lead to at least one of a decrease in the serum levels of triglycerides, ALT, AST and Glucose and to reduction or alleviation of insulin resistance or increase in insulin sensitivity in a subject suffering of an immune-related disorder. Wherein indicated decease, reduction, inhibition, it is meant that the composition of the invention leads to a reduction of about 5% to 99% of the serum level of any one of triglycerides, ALT, AST and Glucose, of a subject suffering of an-immune-related disorder. More specifically, such reduction may be a reduction of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control. Wherein indicated increase, elevation, alleviation, enhancement, induction, it is meant that the composition of the invention leads to induction, or increase of about 5% to 99% of the sensitivity to insulin in a subject suffering of an-immune-related disorder. More specifically, such increase may be an increase of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control.

Moreover, obesity is also associated with numerous inflammatory conditions. Although the precise mechanisms are unknown, obesity-associated rises in TNF-α, IL-6 and TGF-β are believed to contribute to occurrence of sad disorder. The present invention demonstrates that obesity selectively promotes an expansion of the Th17 T-cell sublineage, a subset with prominent pro-inflammatory roles. T-cells from β-glycolipid fed obese mice decrease Th17 cell pools. An increased Th17 bias was suggested to be associated with more pronounced autoimmune disease as confirmed in EAE and trinitrobenzene sulfonic acid colitis. In both, diet-induced obese mice developed more severe early disease and histopathology with increased IL-17+ T-cell pools in target tissues. The well-described association of obesity with inflammatory and autoimmune disease is mechanistically linked to a Th17 bias.

As shown by Example 4, β-glycolipid administration resulted in ratio reversal and a shift towards immune tolerance in an organ specific, dose dependent manner. This underscores the adipose tissue as a dynamic organ, and proposes a new possible mechanism for the second hit in the pathogenesis of the metabolic syndrome and associated insulin resistance and liver injury. Furthermore, it offers a new treatment modality for these conditions, which has been demonstrated effective in oral administration. The role of CD8+ regulatory T cells which has also been affected by glycolipid administration is still unclear and requires further investigation. The fact that TGF-β levels were unaffected by β-glycolipid administration suggest that the effect was mediated by naturally occurring Tregs, and not the inducible type.

JNK play a role in both systemic and hepatic insulin resistance by serine phosphorylation of the insulin receptor substrate (IRS) 1 and IRS2. This leads to down modulation of the tyrosine phosphorylation of these molecules that is required for normal insulin signaling. Both isoforms of JNK play a role in the pathogenesis of NASH [Kaneto, H. et al. Curr. Diabetes Rev. 1: 65-72 (2005); Liu, G. and Rondinone, C. M. Curr. Opin. Investig. Drugs, 6: 979-87 (2005); Malhi, H and Gores, G. J. Semin. Liver Dis. 28: 360-9 (2008)]. Ablation of JNK1 but not JNK2 improves hepatic steatosis. However, JNK2 ablation exacerbate liver injury [Singh, R. et al. Hepatology, 49: 87-96 (2009)]. It was suggested that JNK1 might have a direct effect on hepatic lipogenesis that is independent of insulin resistance. The data presented by the invention supports the protective role of JNK2 in the setting of insulin resistance. JNK2 plays a cytoprotective role by inhibiting Bim-dependent apoptosis via phosphorylation and degradation of Bim [Singh, R. et al. Hepatology, 49: 87-96 (2009)]. The inventors have explored the possibility that the induction of CD4+ T regulatory cells in the adipose tissue is associated with the JNK pathway. As shown by Example 4, the novel analog of the invention, ALIB-97, enhanced JNK2 expression. It has been previously shown that systemic insulin resistance at the level of the adipocytes enhances the flux of free fatty acids to the liver. Hyperinsulinemia was also shown as causing de novo lipogenesis [Kodama, Y. and Brenner, D. A. Hepatology, 49: 6-8 (2009)]. Moreover, obesity, FFA, oxidative stress and ER stress were shown as mediating insulin resistance by modulating different JNK pathways [Kodama, Y. and Brenner, D. A. Hepatology, 49: 6-8 (2009); Kaneto, H. et al. Curr. Diabetes Rev. 1: 65-72 (2005); Liu, G. and Rondinone, C. M. Curr. Opin. Investig. Drugs, 6: 979-87 (2005); Malhi, H and Gores, G. J. Semin. Liver Dis. 28: 360-9 (2008)]. Therefore, the observed enhancement of the JNK2 pathways by the novel analog of the invention ALIB-97 may be applicable in ameliorating insulin resistance.

Thus, according to another embodiment, the composition of the invention may lead to activation of JNK2 pathway and thereby modulation of at least one of adipose and stromal tissue derived Tregs (T regulatory cells) and alleviation of insulin resistance.

As shown by Example 4, such therapeutic composition may be particularly useful in treating an immune-related disorder such as Metabolic Syndrome or any of the conditions comprising the same, non-alcoholic fatty liver disease (NAFLD) or non-alcoholic steatohepatitis (NASH).

More specifically, according to one embodiment, the composition of the invention may be applicable for treating a subject suffering of a metabolic syndrome or any of the conditions comprising the same.

The Metabolic Syndrome is characterized by a group of metabolic risk factors in one person including:

*Abdominal obesity (excessive fat tissue in and around the abdomen); *Atherogenic dyslipidemia (blood fat disorders—high triglycerides, low HDL cholesterol and high LDL cholesterol—that foster plaque buildups in artery walls); *Elevated blood pressure; *Insulin resistance or glucose intolerance; *Prothrombotic state (e.g., high fibrinogen or plasminogen activator inhibitor-1 in the blood); and *Proinflammatory state (e.g., elevated C-reactive protein in the blood). People with the metabolic syndrome are at increased risk of coronary heart disease and other diseases related to plaque buildups in artery walls (e.g., stroke and peripheral vascular disease) and type 2 diabetes.

More particularly, the therapeutic composition of the invention is intended for the treatment of dyslipoproteinemia, which may include hypertriglyceridemia, hypercholesterolemia and low HDL-cholesterol, obesity, NIDDM (non-insulin dependent diabetes mellitus), IGT (impaired glucose tolerance), blood coagulability, blood fibronolysis defects and hypertension.

According to another embodiment, the immunomodulatory composition of the invention may be used for treating diabetes, particularly, type 2 diabetes. Diabetes mellitus, often simply diabetes, is a syndrome characterized by disordered metabolism and inappropriately high blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision. These symptoms are likely absent if the blood sugar is only mildly elevated.

The World Health Organization recognizes three main forms of diabetes mellitus: Type 1, Type 2, and gestational diabetes (occurring during pregnancy), which have different causes and population distributions. While, ultimately, all forms are due to the beta cells of the pancreas being unable to produce sufficient insulin to prevent hyperglycemia, the causes are different. Type 1 diabetes is usually due to autoimmune destruction of the pancreatic beta cells. Type 2 diabetes is characterized by insulin resistance in target tissues, this causes a need for abnormally high amounts of insulin and diabetes develops when the beta cells cannot meet this demand. Gestational diabetes is similar to type 2 diabetes in that it involves insulin resistance, hormones in pregnancy may cause insulin resistance in women genetically predisposed to developing this condition.

Acute complication of diabetes (hypoglycemia, ketoacidosis or nonketotic hyperosmolar coma) may occur if the disease is not adequately controlled. Serious long-term complications include cardiovascular disease (doubled risk), chronic renal failure, retinal damage (which can lead to blindness), nerve damage (of several kinds), and microvascular damage, which may cause impotence and poor healing. Poor healing of wounds, particularly of the feet, can lead to gangrene, which may require amputation.

According to another embodiment, the immunomodulatory composition of the invention may be used for the treatment of type 1 diabetes. Type 1 diabetes mellitus is characterized by loss of the insulin-producing beta cells of the islets of Langerhans in the pancreas, leading to a deficiency of insulin. The main cause of this beta cell loss is a T-cell mediated autoimmune attack.

According to another embodiment, the immunomodulatory composition of the invention may be used for treating non-alcoholic steatohepatitis. Non-alcoholic steatohepatitis (NASH) is a clinico-pathological entity consisting of hepatic fat accumulation, inflammation and fibrosis in patients who have no history of alcohol consumption. It may progress to cirrhosis in 20% of cases and is considered the most common cause of cryptogenic cirrhosis in the Western world. NASH is common in patients who suffer of other metabolic disturbances, which are suggested to play a contributing role in the pathogenesis of the disorder. These include insulin resistance, obesity-related ATP depletion, increased free-fatty-acid beta peroxidation, iron accumulation, antioxidant depletion, and leptin deficiency.

NKT cells are known mediators of the immune-mediated liver injury in the ConA induced hepatitis model [Margalit, M. et. al. Am. J. Physiol. Gastrointest. Liver Physiol. 289: G917-25 (2005)]. Con A, when directly injected into mice, induces T cell-mediated liver injury by activating innate immune cells, including NKT cells [Miyagi, T. et al. Hepatology, 40: 1190-6 (2004)]. Con A injection stimulated IFN-γ production by liver NKT cells [Miyagi, T. et al. Hepatology, 40: 1190-6 (2004)]. Administration of the natural beta glycosphingolipids, GC, ameliorates Con A hepatitis by exerting an inhibitory effect on NKT lymphocytes [Margalit, M. et. al. Am. J. Physiol. Gastrointest. Liver Physiol. 289: G917-25 (2005)]. Beta-glycosphingolipids can overcome the unfavorable host milieu in the setting of Con A hepatitis by suppressing NKT-mediated liver injury [Zigmond, E. et al. Gut 56: 82-9 (2007)]. The data obtained in the present invention show that oral administration of ALIB-97, while decreasing NKT cells in the liver, increases the number of NKT cells in the spleen. In contrast, intraperitoneal administration of ALIB-97 reduced NKT cell number in both organs, suggesting the importance of the first pass effect of ALIB-97 for its immunomodulatory effect in this setting.

As shown by Example 3, the effect of ALIB-97 was mediated by reduced STAT1 and STAT4 phosphorylation. Activation of STAT1 proteins is known to be associated with enhanced liver damage in the Con A model [Torisu, T. et al. Hepatology, 47: 1644-54 (2008)]. Suppressor of cytokine signaling-1 (SOCS1), which is a negative-feedback molecule in cytokine signaling, has been shown to be rapidly induced during liver injury. STAT1 activation is enhanced in SOCS1-deficient livers [Torisu, T. et al. Hepatology, 47: 1644-54 (2008)]. Oral administration of ALIB-97 increased STAT6 expression in the liver. STAT6 is rapidly activated in Con A-induced hepatitis [Jaruga, B. et al. J. Immunol. 171: 3233-44 (2003)]. Although disruption of the IL-4 and STAT6 genes by way of genetic knockout was shown to abolish Con A-mediated liver injury [Margalit, M. et al. J. Pharmacol. Exp. Ther. 319: 105-10 (2006)], the data presented by the invention suggest that the NKT-dependent liver damage is not dependent solely on this pathway.

As shown by the invention, the effect of ALIB-97 on STAT proteins led to suppression of the cytokine efflux, which is one of the hallmarks of Con A hepatitis [Nicoletti, F. et al. Hepatology, 32: 728-33 (2000); Nicoletti, F. et al. Cytokine, 12: 315-23 (2000)]. Serum levels of both IFN-γ and IL-10 were decreased. ALIB-97 had a much stronger effect on IFN-γ suppression as compared with the natural GC, and was similar to that of a high dose of dexamethasone. The effects of ALIB-97 on NKT cells, STAT proteins, and cytokines led to alleviation of immune-mediated hepatitis, as evidenced by a decrease in apoptosis and liver enzymes.

Using the ConA induced hepatitis model, the invention show that the composition of the invention may lead to a decrease in the serum level of at least one of IFN-γ, IL-6 and TNF-α and an increase in the serum level of at least one of IL-10 and IL-4, in a subject suffering from an immune-related disorder. Thus, according to certain embodiments, the immunomodulatory composition of the invention leads to a decrease or reduction in the amount or expression of pro-inflammatory cytokines such as IL-2, IFN-γ, IL-6 and TNF-α. Such decrease or reduction according to the invention may be a reduction of about 5% to 99%, specifically, a reduction of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. In yet another specific embodiment, the composition of the invention elevates and increases the amount or expression of anti-inflammatory cytokines such as IL-10 and IL-4. More specifically, the increase, induction or elevation of the anti-inflammatory cytokines may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

To determine the mechanism of the effects of ALIB-97, the inventors examined its effect in CD1d KO and Jα18 KO mice. Both type I (classical) and type-II (non-classical) NKT cells are CD1d-dependent and are potent producers of IL-4 and IFN-γ [Smith, P. A. et al. AIHA J. (Fairfax, Va.) 63: 284-92 (2002)]. CD1d KO mice lack both type I and type II NKT cells. The combined use of Jα18-deficient and CD1d-deficient mice enabled the inventor to distinguish between type I and type II NKT cells at the functional level in vivo. The data presented in Example 3 show that the protective effect of ALIB-97 in Con A hepatitis is lost in CD1d KO mice, for which administration of ALIB-97 did not significantly alter ALT and AST liver enzymes. Furthermore, ALIB-97 did not alter STAT4 expression in these mice. Finally, ALIB-97 increased IL-10 levels and did not significantly alter the secretion of IL-6 and IFN-γ in CD1d KO mice.

Type I NKT cells possess a TCR with a characteristic a chain, Vα14-Jα18, whereas NKT cells have a diverse TCR. Thus, Jα18 KO mice lack type I NKT cells, but not NKT type II [Oh, S. J. et al. Crit. Rev. Immunol. 28: 249-67 (2008); Tessmer, M. S. et al. Expert Opin. Ther. Targets, 13: 153-62 (2009); Uemura, Y. et al. Int. Immunol. 20: 405-12 (2008)]. Administration of ALIB-97 to Jα18 KO mice exacerbated the liver damage induced by Con A treatment. In Jα18 KO mice, ALIB-97 increased IL-10 and decreased IL-6 and TNFα levels. Taken together the data of the present invention imply that the effect of ALIB-97 depends mostly on type I NKT cells.

Vα14 NKT cells are required and are sufficient for the induction of Con A hepatitis [Kaneko, Y. et al. J. Exp. Med. 191: 105-14 (2000)]. IL-4 produced by Con A-activated Vα14 NKT cells plays a crucial role in disease development by augmenting the cytotoxic activity of Vα14 NKT cells in an autocrine fashion [Kaneko, Y. et al. J. Exp. Med. 191: 105-14 (2000)]. In the Con A model, activation of sulfatide-reactive type II NKT cells is associated with IL-12 and MIP-2 dependent recruitment of type I invariant NKT (iNKT) cells into mouse livers [Halder, R. C. et al. J. Clin. Invest. 117: 2302-12 (2007)]. Recruited iNKT cells are anergic and prevent hepatitis by blocking effector pathways, including the cytokine burst and neutrophil recruitment [Halder, R. C. et al. J. Clin. Invest. 117: 2302-12 (2007)].

Alteration of the NKT ligand structure is an attractive approach for the determination of NKT-dependent immune modulation [Hammond, K. J. and Kronenberg, M. Curr. Opin. Immunol. 15: 683-9 (2003); Wilson, M. T. and Van Kaer, L. Curr. Pharm. Des. 9: 201-20 (2003)]. Both the length of the ligand chain and its saturation determines its function on NKT cells [Tomura, M. et al. J. Immunol. 163: 93-101 (1999); Yu, K. O. et al. J. Immunol. Methods, 323: 11-23 (2007); Yu, K. O. et al. Proc. Natl. Acad. Sci. U.S.A. 102: 3383-8 (2005)].

As demonstrated by Example 3, the ALIB-97 analog of the invention suppresses type I NK T cells and STAT4 expression. Therefore, according to certain embodiments, the therapeutic composition of the invention suppress type I NK T cells and thereby may be used for treating an immune mediated hepatitis.

In yet another embodiment, the immunomodulatory composition of the invention may be used for the treatment of an autoimmune disorder. Examples of autoimmune disorders include, but are not limited to, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

As shown by Example 4, the novel ALIB-97 analog of the invention activates AKT. Recently, there is an increasing interest in generating drugs that can activate Akt (PKB), which could potentially be used to trigger insulin dependent processes for the treatment of diabetes. These compounds could also be used to promote survival and inhibit apoptosis of neuronal cells following a stroke.

Thus, in yet another embodiment, the compositions of the invention may be particularly suitable for the treatment of a neurodegenerative disorder such as a protein misfolding disorder, an amyloid disease, a CNS autoimmune disease, taupathy or a prion disease. More particularly, said neurodegenerative disorder may be any one of Alzheimer's disease, Parkinson's disease, ALS (Amyotrophic Lateral Sclerosis), Huntington's disease, Pick's disease, fronto temporal dementia, cortico-basal degeneration, progressive supranuclear palsy, Spongiform encephalopathies, Scrapie, mad cow disease and Bovine spongiform encephalopathy, Creutzfeldt-Jakob disease, Fatal Familial Insomnia, Gerstmann-Straussler-Scheinker syndrome and Kuru.

According to certain embodiments, the therapeutic and the immunomodulatory compositions of the invention may be capable of modulating the Th1/Th2, Th3 cell balance towards a pro-inflammatory Th1 response in a subject suffering of an immune-related disorder. Such pro-inflammatory compositions may be applicable for immune-related disorder such as malignant and non-malignant proliferative disorder, genetic disease, bacterial infections, viral infections, fungal infections, or parasitic infections.

According to this embodiment, the therapeutic composition and the immunomodulatory compositions of the invention may be used for the treatment of a malignant proliferative disorder such as solid and non-solid tumor. More particularly, such tumors may be carcinoma, sarcoma, melanoma, leukemia and lymphoma. Even more particularly, said solid and non-solid tumors may be any one of hepaotcellular carcinoma, melanoma, colon cancer, myeloma, acute and chronic leukemia.

As shown by Examples, the novel analogs of the invention, specifically, ALIB-97 exhibit a clear immuno-modulatory effect on immune-related cell, specifically, adipose and stromal derived T regulatory cells. More particularly, the novel derivatives of the invention and specifically ALIB-97, demonstrate immuno-modulation, specifically, anti-inflammatory effect on immune-related cells such as specific T regulatory cells for example, CD4+LAP+, adipocytes and Antigen Presenting Cells (APC), such as DC. Therefore, according to one embodiment, the composition of the invention may be used for inducing at least one of T regulatory (Treg) cells, or any cell having regulatory properties, either suppressive or inductive, adipocyte and Antigen Presenting Cells (APC) in a subject suffering from an immune-related disorder. More specifically, immune-related cells induced by the composition of the invention may be any T regulatory cell, for example any one of CD4+LAP+ T-reg cells, CD4+CD25 T-reg cells, CD8+ CD25 T-reg cells and FoxP3+CD4 T-reg cells.

As demonstrated by Example 3, the clear inducing effect of the composition of the invention on a specific population of Treg. cells may enable the isolation and use of these cell for adoptive transfer. Thus, according to another embodiment, the invention further provides a composition comprising immune-cells, specifically, Tregs. It is understood that one of skill in the art will recognize that other immune-related cells may be useful in the invention. An immune-related cell may be an APC (such as DC), Treg cell or any other cell associated directly or indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties.

According to a more specific embodiment, the therapeutic and the immunomodulatory compositions of the invention may further comprises at least one component of said subject's immune-system which was pre-exposed to an effective amount of any one of the compounds of said Formula I, II, III or IV, or to any mixture or any combination thereof. As indicated above, and according to certain embodiments, such immune-system components may be immune cells and more specifically, NK T cells that were exposed to the compounds of the invention or to any combination or mixture thereof. According to this embodiment, such educated NK T cells are capable of modulating the Th1/Th2 cell balance toward an anti-inflammatory or pro-inflammatory response. More particularly, such educated NK T cells may be, prior to their administration to the treated subject, cultured or "educated" in the presence of any one of: (a) at least one of the compounds of Formula I, II, III, IV or a mixture of at least two compounds of Formula I, II, III, IV or any combination thereof; (b) combination of (a) with antigens associated with the treated pathologic disorder; (c) combination of (a) with at least one of liver-associated cells of tolerized or non-tolerized subject suffering from said pathologic disorder or of said subject; (d) combination of (a) with at least one of cytokines, adhesion molecules and any combination thereof; (e) combination of (a) with antigen presenting cells; and (f) a combination of any of (b), (c), (d) and (e).

According to one preferred embodiment, said education of NK T cells may result in the modulation of the Th1/Th2 cell balance toward Th2 anti-inflammatory cytokine producing cells. In certain embodiments, such composition may be applicable in treating immune related disorder such as Metabolic Syndrome or any of the conditions comprising the same, Non-alcoholic fatty liver disease (NAFLD), non-alcoholic steatohepatitis (NASH), immune mediated hepatitis, an autoimmune disease, graft rejection pathology, inflammatory disease, hyperlipidemia, atherosclerosis and a neurodegenerative disorder.

The NK T cell that has been ex vivo educated may also be comprised within the compositions of the invention and therefore may be re-introduced to the treated subject. This can be carried out by a process that has been termed adoptive transfer. The particular educated NK T cells used for the transfer may preferably originate from the subject (autologous transfer). A syngeneic or non-syngeneic donor (non-autologous transfer) is not excluded. The storage, growth or expansion of the transferred cells may have taken place in vivo, ex vivo or in vitro.

Cell therapy may be by injection, e.g., intravenously, or by any of the means described herein above. Neither the time nor the mode of administration is a limitation on the present invention. Cell therapy regimens may be readily adjusted taking into account such factors as the possible cytotoxicity of the educated cells, the stage of the disease and the condition of the patient, among other considerations known to those of skill in the art.

It is to be appreciated that the NK T cells used by the compositions of the invention may be educated in vivo as well, via any of the methods described above, they can be modulated prior to or at any point of time following exposure to the synthetic derivatives of β-glycolipids as defined by the invention, antigens or any other component described.

According to another preferred embodiment, said education of NK T cells may result in the modulation of the Th1/Th2 cell balance toward Th1 pro-inflammatory cytokine producing cells. According to this embodiment the educated NK T cells used for the compositions of the invention may be intended for the treatment of malignant and non-malignant proliferative disorder, bacterial infections, viral infections, fungal infections, or parasitic infections.

The therapeutic composition of the invention may optionally further comprises at least one of a pharmaceutically acceptable carrier, diluent, excipient and/or additive.

In certain embodiments, any of the therapeutic and immunomodulatory compositions of the invention may optionally further comprise another active ingredient which may be any one of: (a) antigens associated with the specific pathologic disorder to be treated; (b) at least one of liver-associated cells of tolerized or non-tolerized subjects suffering from the treated pathologic disorder or of the subject to be treated (autologous cells); (c) at least one of cytokines, adhesion molecules or any combination thereof; (d) antigen presenting cells; and (e) a combination of any of (a), (b), (c) and (d).

More specifically, antigens associated with said pathologic disorder to be treated may be for example, any one of allogeneic antigens obtained from a donor subject suffering from said immune-related disorder, xenogenic antigens, syngeneic antigens, autologous antigens, non-autologous antigens and recombinantly prepared antigens and any combinations thereof. These antigens can be native or non-native with regards to the subject. They can be natural or synthetic, modified or unmodified, whole or fragments thereof. Fragments can be derived from synthesis as fragments or by digestion or other means of modification to create fragments from larger entities. Such antigen or antigens comprise but are not limited to proteins, glycoproteins, enzymes, antibodies, histocompatibility determinants, ligands, receptors, hormones, cytokines, cell membranes, cell components, viruses, viral components, viral vectors, non-viral vectors, whole cells, tissues or organs. The antigen can consist of single molecules or mixtures of diverse individual molecules. The antigen can present itself within the context of viral surface, cellular surface, membrane, matrix, or complex or conjugated with a receptor, ligand, antibody or any other binding partner.

Polymerization and degradation, fractionation and chemical modification are all capable of altering the properties of a particular antigen in terms of potential immune responses. These small segments, fragments or epitopes can either be isolated or synthesized.

The compositions of the present invention further encompass the use of recombinantly prepared antigens. Preparation of recombinant antigens involves the use of general molecular biology techniques that are well known in the art. Such techniques include for example, cloning of a desired antigen to a suitable expression vector.

According to another embodiment, liver-associated cells may be for example Kupffer cells, Stellate cells, liver endothelial cells liver associated stem cells or any other liver-related lymphocytes.

The use of peripheral lymphocytes from tolerized or non-tolerized patients suffering from the same immune-related disorder or from the treated subject is also contemplated in the present invention. In order to obtain lymphocytes from a subject, particularly human subject, blood is drawn from the patient by cytopheresis, a procedure by which a large number of white cells are obtained, while other blood components are being simultaneously transferred back to the subject.

In another particular embodiment, cytokines such as IL4, IL10, TGFβ, IFNγ, IL12 and IL15, or adhesion molecules such as Integrins, Selectin and ICAM may also be included in the composition of the invention.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

The pharmaceutical composition of the invention can be administered and dosed in accordance with good medical practice. Administration may be carried out in various ways, including oral, intraperitoneal, intravenous, intramuscular or subcutaneous injection. However, other methods of administration such as nasal or topical administration are also contemplated by the invention.

The composition of the invention may comprise the active substance in free form and be administered directly to the subject to be treated. Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

As indicated above, Formulations include those suitable for oral, intraperitoneal (i.p.), nasal, or parenteral [including subcutaneous (s.c.), intramuscular (i.m.), intravenous (i.v.) and intradermal administration]. The Formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringe ability exists. The compositions must be stable under the conditions of manufacture and storage and must be preserved against the contaminating action of microorganisms, such as bacteria and fungi.

In many cases, it will be preferable to include isotonic agents, for example, sugars or sodium chloride. Prolonged absorption of the injectable compositions can be brought about by the use in the compositions of agents delaying absorption.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Alternatively, the composition of this invention may also be administered in controlled release formulations such as a slow release or a fast release Formulation. Such controlled release formulations of the combination of this invention may be prepared using methods well known to those skilled in the art. The method of administration will be determined by the attendant physician or other person skilled in the art after an evaluation of the subject's conditions and requirements.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art. Methods of preparing various pharmaceutical compositions with a certain amount of active ingredient are known, or will be apparent in light of this disclosure, to those skilled in this art.

According to a further aspect, the invention provides a method for treating, preventing, ameliorating or delaying the onset of a pathologic disorder in a mammalian subject in need thereof. The method of the invention comprises the step of administering to the treated subject a therapeutically effective amount of any one of: (a) at least one of the compounds of Formula I, II, III or IV; (b) a mixture of at least two compounds of Formula I, II, III or IV; (c) at least one component of the treated subject's immune-system which was pre-exposed to an effective amount of any one of the compounds of Formula I, II, III or IV, or to any mixture or any combination thereof; (d) a composition comprising any one of (a), (b) and (c) or (e) any combination of (a), (b), (c) and (d).

It should be noted that compound of Formula I, II, III or IV used by the methods of the invention are as defined by the invention.

According to one embodiment, a mixture of the compounds of Formula I, II, III or IV used by the methods of the invention may comprises at least two of the compounds of Formula I, II, III, IV or any β-glycolipid derivatives at a quantitative ratio between 1:1 to 1:1000.

According to one specific embodiment, the mixture used by the methods of the invention preferably comprises the compound of Formula I and at least one of the compounds of any one of Formula II, III, IV or any other synthetic or natural derivative of β-glycolipid, at a quantitative ratio between 1:1 to 1:1000.

According to another specific embodiment, the mixture used by the methods of the invention preferably comprises the compound of Formula II and at least one of the compounds of any one of Formula I, III, IV or any other synthetic or natural derivative of β-glycolipid, at a quantitative ratio between 1:1 to 1:1000.

According to another specific embodiment, the mixture used by the methods of the invention preferably comprises the compound of Formula III and at least one of the compounds of any one of Formula I, II, IV or any other synthetic or natural derivative of β-glycolipid, at a quantitative ratio between 1:1 to 1:1000.

In another specific embodiment, the mixture used by the methods of the invention preferably comprises the compound of Formula IV and at least one of the compounds of any one of Formula I, II, III or any other synthetic or natural derivative of β-glycolipid, at a quantitative ratio between 1:1 to 1:1000.

According to one particular embodiment, the methods of the invention comprises the step of administering to the treated subject a therapeutically effective amount of at least one component of the treated subject's immune-system which was pre-exposed to an effective amount of any one of the compounds of Formula I, II, III or IV, or to any mixture or any combination thereof. According to this embodiment, a component of the treated subject's immune-system may be selected from the group consisting of cellular immune reaction elements, humoral immune reaction elements and cytokines. Preferably, such cellular immune reaction element may be a population of NKT cells.

More specifically, according to this embodiment, such NK T cells were exposed to an effective amount of any one of a compound of Formula I, II, III or IV, or to any mixture or any combination thereof. The exposure of the NK T cells may be performed by the steps of: (a) obtaining NK T cells from said subject, or from a non autologous subject; (b) ex vivo educating the NK T cells obtained in step (a) such that the resulting educated NK T cells modulate the Th1/Th2 cell balance toward an anti-inflammatory or pro-inflammatory cytokine producing cells; and (c) re-introducing to said subject the educated NK T cells obtained in step (b) which modulate the Th1/Th2 cell balance toward Th2 anti-inflammatory cytokine producing cells.

The ex vivo education of such NK T cells is as described herein before for the therapeutic and the immunomodulatory compositions of the invention.

According to certain embodiments, the method of the invention may lead to modulation of the Th1/Th2, Th3 cell balance in a subject suffering from an immune-related disorder. Such modulation may activate or inhibit an immune response specifically directed toward said disorder in the treated subject.

Thus, according to another embodiment, the methods of the invention are suitable for the treatment of a pathologic disorder such as an immune-related disorder or a neurodegenerative disorder.

As used herein, the term "disorder" or "condition" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

According to certain embodiments, the method of the invention may lead to modulation of the Th1/Th2, Th3 cell balance toward an anti-inflammatory Th2, Tr1/Th3 immune response in a subject suffering from an immune-related disorder.

According to one particular embodiment, the invention provides a method comprising the step of administering to said subject a therapeutically effective amount of the compound of Formula II (ALIB-97) or any mixtures and combinations thereof.

According to another particular embodiment, such method leads to at least one of a decrease in the serum levels of triglycerides, ALT, AST and Glucose and to reduction of insulin resistance in a subject suffering of an immune-related disorder.

Still further, the method of the invention may lead to activation of JNK2 pathway and thereby modulation of at least one of adipose and stromal tissue derived Tregs (T regulatory cells).

According to certain embodiments, such method may be applicable in the treatment of an immune-related disorder such as Metabolic Syndrome or any of the conditions comprising the same, non-alcoholic fatty liver disease (NAFLD) or non-alcoholic steatohepatitis (NASH).

According to another specific embodiment, the method of the invention may lead to a decrease in the serum level of at least one of IFN-γ, IL-6 and TNF-α and an increase in the serum level of at least one of IL-10 and IL-4, in a subject suffering from an immune-related disorder. Furthermore, the method of the invention leads to suppression of type I NK T cells and STAT4 expression. Therefore, according to certain embodiments, the method of the invention may be particularly applicable in treating an immune related disorder such as an immune mediated hepatitis.

According to another embodiment, the methods of the invention are intended for treating an autoimmune disease. Non-limiting examples for an autoimmune disease include rheumatoid arthritis, diabetes, asthma, acute and chronic graft versus host disease, systemic lupus erythmatosus, scleroderma, multiple sclerosis, hyperlipidemia, atherosclerosis, overweight and inflammatory bowel disease.

In another specific embodiment, the methods of the invention are intended for the treatment of a neurodegenerative disorder such as a protein misfolding disorder, an amyloid disease, a CNS autoimmune disease, taupathy or a prion disease.

A "neurological disorder" is a disease or disorder characterized by an abnormality or malfunction of neuronal cells or neuronal support cells. The disorder can affect the central and/or peripheral nervous system. Exemplary neurological diseases include neuropathies, skeletal muscle atrophy and neurodegenerative diseases.

"Neurodegenerative disorders" are complex and pernicious diseases, their onset is insidious, followed by progressive deterioration. Clinical manifestations are determined by the location and seriousness of the disorder. Although the causes may differ, patients with neurodegenerative disorders are likely to show localized to generalized atrophy of brain cells, leading to compromises in both mental and physical function. Exemplary neurodegenerative diseases include: Alzheimer's disease, Parkinson's disease, ALS (Amyotrophic Lateral Sclerosis), Huntington's disease, taupathies such as Pick's disease, fronto temporal dementia, cortico-basal degeneration and progressive supranuclear palsy and Spongiform encephalopathies such as Scrapie, mad cow disease and Bovine spongiform encephalopathy, Creutzfeldt-Jakob disease, Fatal Familial Insomnia, Gerstmann-Straussler-Scheinker syndrome and Kuru.

Mentally, patients will exhibit forgetfulness, poor memory, decrease in mental capacities, emotional disturbances, and/or poor speech. Physically, patients will exhibit partial to complete incontinence, aspiration of food particles, tremor, poor balance, muscle rigidity, and/or muscle paralysis.

"Prion diseases" often called "spongiform encephalopathies", are a group of progressive conditions that affect the brain and nervous system of humans and animals. The disorders cause degenerative diseases of the nervous system reflected by impairment of brain function, including memory changes, personality changes, and problems with movement that worsen over time. Probably most mammalian species develop these diseases. The infectious agent causing the diseases has been called a prion. A "prion" has been defined as a small proteinaceous infectious particle which resists inactivation by procedures that modify nucleic acids. Prions are microscopic protein particles similar to a virus but lacking nucleic acid, capable of self-reproducing. Though their exact mechanisms of action and reproduction are still unknown, it is accepted that they are responsible for a number conditions in humans, Creutzfeld-Jacob Disease (CJD), Gerstmann-Straussler-Scheinker syndrome (GSS), Fatal Familial Insomnia (FFI), Kuru, Alpers Syndrome; and in cattle (livestock), Scrapie in sheep, transmissible mink encephalopathy (TME) in mink, chronic wasting disease (CWD) in mule deer or elk, and bovine spongiform encephalopathy (BSE) in cows.

Abundant cytoplasmic inclusions consisting of aggregated hyperphosphorylated protein tau, called neurofibrillary tangles (NFT), are a characteristic pathological observation in several neurodegenerative disorders, known as taupathies. These disorders include Alzheimer's disease, Pick's disease, frontotemporal dementia, cortico-basal degeneration and progressive supranuclear palsy.

According to certain embodiments, the methods of the invention are capable of modulating the Th1/Th2 cell balance towards Th1 pro-inflammatory cytokine producing cells, and may be applicable for the treatment of any one of malignant and non-malignant proliferative disorder, genetic disease, bacterial infections, viral infections, fungal infections, or parasitic infections.

As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors.

Malignancy, as contemplated in the present invention may be for example, carcinoma, melanoma, lymphoma, leukemia and sarcoma. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi). More particularly, the malignant disorder may be hepaotcellular carcinoma, colon cancer, melanoma, myeloma, acute or chronic leukemia.

According to a particular embodiment, the viral infection treated by the methods and compositions of the invention, may be caused by any one of HBV, HCV or HIV.

According to a specifically preferred embodiment, the methods of the invention are specifically suitable for the treatment of a mammalian subject. "Mammal" or "mammalian" for purposes of treatment refers to any animal classified as a mammal including, human, research animals, domestic and farm animals, and zoo, sports, or pet animals, such as dogs, horses, cats, cows, etc. In a particular embodiment said mammalian subject is a human subject.

The terms "treat, treating, treatment" as used herein and in the claims mean ameliorating one or more clinical indicia of disease activity in a patient having a pathologic disorder.

"Treatment" refers to therapeutic treatment. Those in need of treatment are mammalian subjects suffering from any pathologic disorder by "patient" or "subject in need" is meant any mammal for which administration of the synthetic β-glycolipid derivatives and analogs of the invention which are preferably any one of the compounds of Formula I, II, III or IV, any combination thereof or any pharmaceutical composition comprising this compound, is desired in order to prevent, overcome or slow down such infliction.

To provide a "preventive treatment" or "prophylactic treatment" is acting in a protective manner, to defend against or prevent something, especially a condition or disease.

It should be noted that for the method of treatment and prevention provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the composition of the invention in bodily fluids or tissues. Following successful treatment, it may be desirable to have the patient undergo maintenance therapy to prevent the recurrence of the disease state, wherein the composition of the invention is administered in maintenance doses, once or more daily.

According to another embodiment, the synthetic β-glycolipid derivatives of the invention, particularly, the compounds of Formula I, II, III, or IV, used by the methods of the invention or any mixture or combination thereof may administered alone, or in combination with other active ingredient/s that improve the therapeutic effect, whether administered in combination, serially or simultaneously.

The methods of the invention involve administration of effective amount of the active ingredient to a subject in need thereof. The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

As shown by Examples 2, 3, and 4, oral or intraperitoneal administration of the composition of the invention that comprises any of the novel derivatives of the invention, and specifically an amount of 1, 10, 15, 45 μg ALIB-97, showed significant anti-inflammatory effects, using the ob/ob model and the ConA induced hepatitis model. Based on these results, an effective amount of such particular analog may range between about 0.01 to 100, specifically, 0.05 to 50, and more specifically, 0.5, 5, 7.5 or 20 mg per kg of body weight of ALIB-97.

It should be appreciated that these preferred amounts of active ingredients are specific for a certain immune-related disorders, the Metabolic Syndrome and the immune-related hepatitis. Appropriate concentrations for any other immune-related disorders should be determined by the treating physician.

Therapeutic and immunomodulatory Formulations may be administered in any conventional dosage Formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The Formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

In yet another embodiment, the administration step according to the methods of the invention includes intraperitoneal, oral, intravenous, intramuscular, subcutaneous, perenteral, transdermal, intravaginal, intranasal, mucosal, sublingual, topical, rectal or subcutaneous administration, or any combination thereof.

The invention further provides a method for protection of neuronal cells from a neurodegenerative process comprising the step of contacting said cells with a neuroprotective effective amount of any one of a compound of Formula I, II, III, IV, or any mixture or any combination thereof, a composition comprising the same or any combinations thereof.

A "neuroprotective effect" is aimed to prevent and treat complications that might result in central nervous system (CNS) damage. Neuroprotection can be estimated by parameters of cell survival or cell death delay, arrest or slowing of the disease progression, disease onset and disease mortality delay.

Neuroprotective agents usually interact with the cell survival/apoptotic machinery. Products with neuroprotective effects include those from the categories of free radical scavengers, anti-excitotoxic agents, apoptosis (programmed cell death) inhibitors, anti-inflammatory agents, neurotrophic factors, metal ion chelators, ion channel modulators and gene therapy.

Neuroprotective therapies are usually directed to cerebrovascular disorders, traumatic brain injury, spinal cord injury, Alzheimer's disease, Parkinson's disease, amyotrophic lateral sclerosis, Huntington's disease, taupathies, multiple sclerosis, epilepsy and ischemic optic neuropathy.

Still further, the invention provides a method for the preparation of a medicament for the treatment of a pathologic disorder in a subject in need thereof comprising the steps of: (A) providing an immunomodulatory compound comprising any one of: (a) at least one of the compounds of Formula I, II, III or IV, a mixture of at least two compounds of Formula I, II, III or IV, at least one component of said subject's immune-system which was pre-exposed to an effective amount of any one of the compounds of said Formula I, II, III or IV, or to any mixture or any combination thereof; and (B) admixing the immunomodulatory compound provided in step (A) with a pharmaceutically acceptable carrier.

According to a further aspect, the invention relates to the use of a therapeutically effective amount of any one of a compounds of Formula I, II, III, IV, or any combinations and mixtures thereof, in the preparation of a pharmaceutical composition for the treatment or prevention of a pathologic disorder in a subject in need thereof. More preferably, the use according to the invention is of a compound of Formula I, II, III or IV, as defined by the invention.

In another embodiment, the use according to the invention may be wherein the pathologic disorder is any one of an immune-related disorder and a neurodegenerative disorder.

The invention further provides the use of the immunomodulatory composition according to the invention as a supporting medicament for the treatment of immune-related disorders and neurodegenerative disorder.

Beta-glyocosphingolipids are natural molecules that exert an NKT-dependent immune-mediated effect [Margalit, M. et. al. Am. J. Physiol. Gastrointest. Liver Physiol. 289: G917-25 (2005); Zigmond, E. et al. Gut 56: 82-9 (2007); Ilan, Y. et al. Transplantation, 83: 458-67 (2007); Lalazar, G. et al. J. Lipid Res. 49: 1884-93 (2008); Lalazar, G. et al. Mol. Immunol. 45: 3517-25 (2008); Livovsky, D. M. et al. Int. Immunopharmacol. 8: 1298-305 (2008); Mizrahi, M. et al. Vaccine, 26: 2589-95 (2008)]. GC was previously shown to alleviate the NKT-mediated damage in Con A hepatitis [Margalit, M. et. al. Am. J. Physiol. Gastrointest. Liver Physiol. 289: G917-25 (2005)]. In contrast to αGalCer, oral administration of β-glucosylceramide is not associated with liver injury in mice [Margalit, M. et. al. Am. J. Physiol. Gastrointest. Liver Physiol. 289: G917-25 (2005); Zigmond, E. et al. Hepatology, 44: 180A (2006)]. Preliminary data suggest that GC is safe and biologically active in humans [Zigmond, E. et al. Hepatology, 44: 180A (2006)]. The present invention shows that ALIB-97 was more potent in alleviating the liver damage in comparison to the natural glycolipid GC. The effect of oral administration of ALIB-97 was comparable to that of dexamethasone, further supporting its efficacy as an anti-inflammatory ligand.

ALIB-97 is characterized by a bulky acyl chain that may affect the cross talk between dendritic cells, NKT cells, and regulatory T cells; this crosstalk may explain its enhanced immune modulatory effect. The bulky residue may be associated with more potent receptor binding, thereby increasing its biological activity. Beta-glycosphingolipids have been shown to alter the lipid rafts in lymphocyte membranes, and thus the intracellular signaling machinery of NKT cells [Lalazar, G. et al. J. Lipid Res. 49: 1884-93 (2008); Lalazar, G. et al. Mol. Immunol. 45: 3517-25 (2008)]. The alteration in the expression levels of flotillin-2, Lck, and STAT1 that occurs concomitantly with changes in lipid raft composition and structure following administration of beta-glycolipids in Con A-induced hepatitis is microenvironment-dependent and is associated with decreased intrahepatic CD8+ lymphocyte liver trapping [Lalazar, G. et al. Mol. Immunol. 45: 3517-25 (2008)]. The demonstration of altered red blood cell (RBC) aggregation in patients with Gaucher's disease, wherein GC is accumulated, lends further support to the concept of cell membrane alteration by glycosphingolipids [Adar, T. et al. Br. J. Haematol. 134: 432-7 (2006); Adar, T. et al. Clin. Hemorheol. Microcirc. 40: 113-8 (2008)]. ALIB-97 may exert its effects by alteration of cell membrane associated proteins, which may also be responsible for its more potent effect.

The invention therefore further provides a diagnostic method for predicting responsiveness of a subject suffering from a pathologic disorder to treatment with synthetic or natural derivatives of β-glycolipids. The diagnostic method of the invention is based on monitoring the direct or indirect modulations in structure and composition of a cell membrane obtained from the tested subject in response to treatment with the synthetic or natural derivatives of β-glycolipids. This diagnostic method comprises the steps of: (a) obtaining cells from the tested subject; (b) exposing these cells to an effective amount of a compounds of Formula I, II, III, IV, or any combinations and mixtures thereof under suitable conditions; and (c) identifying an alteration in the membrane composition and structure of said cells, as compared to a control, by a suitable means.

Wherein an alteration in the membrane composition and structure of the cells as compared to a control is indicative of responsiveness of said subject to treatment with said synthetic or natural derivative of glycolipids.

By predicting the responsiveness of the particular tested subject to a certain synthetic derivatives of β-glycolipids, in a certain concentration or mixture thereof, the diagnostic method of the invention provides a "tailor-made" treatment, personally adjusted and adapted for each specific patient.

It should be further appreciated that the diagnostic method of the invention may also be used for follow-up of treated patients.

According to one embodiment, the cells obtained from the tested subject may be any one of microglial cells, NKT lymphocyte, and dendritic cell, any regulatory lymphocyte, and type of lymphocyte.

Unless otherwise defined, all technical and scientific terms used herein have the same meaning as commonly understood by one of ordinary skill in the art to which this invention belongs. Although methods and materials similar or equivalent to those described herein can no be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

DESCRIPTION OF THE PREFERRED EMBODIMENTS

Material and Methods

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Md. (1988) and in Vanderkerken K The 5T2MM murine model of multiple myeloma: maintenance and analysis. [Methods Mol. Med. 113:191-205 (2005); Epstein J. The SCID-hu myeloma model. Methods Mol. Med. 113:183-90 (2005)].

Standard organic synthesis protocols known in the art not specifically described herein are generally followed essentially as in Organic syntheses: Vol. 1-79, editors vary, J. Wiley, New York, (1941-2003); Gewert et al., Organic synthesis workbook, Wiley-VCH, Weinheim (2000); Smith & March, Advanced Organic Chemistry, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

Animals

For the ConA Induced Hepatitis Experiments:

*male C57BL/6 (B6) mice (11-12 weeks old) were purchased from Harlan Laboratories (Jerusalem, Israel).

*CD1d−/− mice were originally generated and kindly provided by Luc Van Kaer (Department of Microbiology and Immunology, Medical Center North, Vanderbilt University School of Medicine, Nashville, Tenn.).

*Jα18−/− mice were originally generated and kindly provided by Masaru Taniguchi (Laboratory for Immune Regulation, Kanagawa, Japan). Both knockout mice were on the B6 background.

For the Metabolic Syndrome Experiments:

*Young (age 6-7 weeks) male C57BL/6J Ob/Ob mice were purchased from Harlan Laboratories (USA).

*Eight week old male C57/bl mice are obtained from Jackson Laboratories (Bar Harbor, Me., USA).

*The sand rat (*Psammomys obesus*), are purchased from the Jerusalem colony were purchased from Harlan laboratories (Jerusalem, Israel).

*Diabetic Cohen rats are purchased from the Jerusalem colony were purchased from Harlan laboratories (Jerusalem, Israel).

For Neuro-Degenerative Disorders Experiments:

*Male Sprague-Dawley rats (weighing 250-270 g), purchased from Harlan Laboratories Israel, are used as a PD model.

*14-15 weeks old transgenic mice expressing the human G93A SOD1 (B6SJL-TgN[SOD1-G93A]1Gur, purchased from Jackson Laboratory), are used as a model showing ALS related clinical symptoms.

*Transgenic mice model expressing a mutation in the amyloid precursor protein (APP) and in the presenilin1 gene is used as AD model. These tg mice present amyloid plaques starting at 9 months of age (purchased from Jackson Laboratory).

*C57Bl mice, purchased from Harlan Laboratories Israel, immunized with MOG.

*SJL/j mice immunized with PLP are purchased from Harlan Laboratories Israel.

All animals were bred and maintained in specific pathogen-free conditions. Mice were maintained in the Animal Core of the Hadassah-Hebrew University Medical School. All mice were administered standard laboratory chow and water ad libitum and kept in a 12-hour light/dark cycle. The animal experiments were carried out according to the guidelines of the Hebrew University-Hadassah Institutional Committee for the Care and Use of Laboratory Animals and with the committee's approval.

Preparation of Glycosphingolipids

β-glucosylceramide was purchased from Avanti Polar Lipids (Alabaster, Ala., USA). The analog of β-glucosylceramide, ALIB-97 was prepared in the inventor's lab form D-galactosyl-β1-1′ Sphingosine (Psychosine) purchased from Avanti Polar Lipids (FIG. 6). Preparation of all analogs is described by Example 1. All glycolipids were dissolved in a mixture of 30% Cremophor EL (Sigma, Rehovot, Israel) and ethanol (1:1) in PBS.

Neurotoxins

*A β (25-35) peptide purchased from Sigma.

*Cholesterol purchased from Sigma.

*3-NP purchased from Sigma.

*MPTP purchased from Sigma.

*6OHDA purchased from Sigma.

*Glutamate purchased from Sigma.

Hepatocellular Damage

The effect of β-glycolipids on liver injury was evaluated by serum aspartyl transaminase (AST) and alanine aminotransferase (ALT) activities, which were determined by a clinical chemistry analyzer, Reflovet Plus (Roche Diagnostics, GmbH, Mannheim, Germany).

Assessment of Lipid Accumulation in the Liver

Triglycerides (TGs) were extracted from aliquots of snap-frozen livers using a modification of the Folch method. Hepatic TGs content was assayed spectrophotometrically using the GPO-Trinder kit (Sigma, Rehovot, Israel) and was normalized to the protein content in the homogenate.

Measurement of Plasma Lipids

Plasma triglyceride and total cholesterol were measured by a clinical chemistry analyzer Reflovet Plus machine (Roche Diagnostics, GmbH, Mannheim, Germany).

Glucose Tolerance Test

Mice underwent a glucose tolerance test (GTT) on day 30 after overnight fasting. Glucose was administered orally (1.25 g per kg). Serum glucose measurements were performed on tail-vein blood every 15 min for 3 h. Glucose levels were measured by a standard glucometer.

Cytokine Determination

Serum levels of IFN-γ, TGF-β, TNF-α IL-2, IL-4, IL-6, IL-10 and IL-12 were determined by "sandwich" ELISA, using commercial kits (Quantikine, R&D Systems, Minneapolis, Minn., USA). Serum insulin was also determined by "sandwich" ELISA too, using the commercial kit of Mercodia AB (Uppsala, Sweden) according to the manufacturer's instructions.

Immunoblot Analysis

For analysis of whole tissue lysates, snap-frozen liver pieces were homogenized in 0.75 ml of ice-cold PBS and centrifuged at 4° C. for 5 min in 2000 rpm. Pellets were lysed with 50 mM beta glycerophosphate, 1.5 mM EGTA, PH 7.3, 1 mM EDTA, PH 7.3, 1 mM DTT, 0.1 mM Sodium vanadate, 1% NP-40, and cocktails of protease and phosphatase (Sigma, Rehovot, Israel).

For ConA induced hepatitis experiments spleen and liver lysates were lysed in RIPA buffer containing 50 mM Tris, pH 7.4, 1% NP-40, 150 mM NaCl, 0.1% SDS, 0.5% sodium deoxycholate and protease inhibitors (5 μg/ml, Sigma), with protease and phosphatase (Sigma, Rehovot, Israel).

Lysates were centrifuged twice at 4° C. for 10 minutes in 14000 rpm. Equivalent amounts of lysates (15 μg/lane), determined by Bradford assay (Bio-Rad, Rehovot, Israel), were separated by sodium dodecyl sulfate polyacrylamide gel electrophoresis (SDS-PAGE) and transferred to nitrocellulose membranes.

For metabolic syndrome experiments, proteins were detected with JNK-2, Phospho JNK (Thr183/Tyr185), Akt and phospho Akt (Ser 473) antibodies (Cell Signaling Technologies, MA). β-actin (abcam, UK) was used as the loading control.

For ConA induced hepatitis experiments proteins were detected with phospho-specific STAT1-Tyr701, STAT6-Tyr641, STAT1, and STAT6 antibodies from Cell Signaling. β-actin (abcam, UK) was used as a loading control.

Blots were developed with horseradish peroxidase-conjugated secondary antibodies (Jackson Laboratories Bar Harbor, Me.) and Western Blot-Luminol Reagent (Santa Cruz Biotechnology, CA, USA). Cell counting and western Blot quantification was performed using total Lab (Phoretix, USA) software.

Isolation of Splenocytes and Intrahepatic Lymphocytes

Splenocytes and intrahepatic lymphocytes were isolated as follows: livers and spleens were kept in RPMI-1640+FCS. Then spleens were crushed through a 70 μm nylon cell strainer (Falcon) and centrifuged (1250 rpm for 7 min) for the removal of cell debris. Red blood cells were lysed with 1 ml of cold 155 mM ammonium chloride lysis buffer and centrifuged (1250 rpm for 3 min). Splenocytes were resuspended with 1 ml RPMI+FCS. Cell viability by trypan blue staining was above 90%. For intrahepatic lymphocytes, livers were crushed through a stainless mesh (size 60, Sigma) and the cell suspension was placed in a 50-ml tube for 5 min. Lymphoprep (10 ml, Ficoll, Axis-Shield PoC AS, Oslo, Norway) was placed under similar volume of cell suspension in 50-ml tubes. Tubes were centrifuged at 1800 rpm for 18 min. Cells in the interface were collected and centrifuged at 1800 rpm for 10 min, to obtain a pellet of cells depleted of hepatocytes to a final volume of 250 μl. Approximately $1 \times 10^6$ cells/mouse liver, were recovered.

Isolation of Adipocytes and Adipose Tissue-Associated Stromal-Vascular (S/V) Cells Adipose tissue (visceral fat pads) was minced and incubated in Krebs-Ringer bicarbonate buffer (3 mL/g adipose tissue) containing 10mM glucose and 2.5% bovine serum albumin, incubated with 840 U/g collagenase type I (Sigma, Rehovot, Israel)) at 37° C. for 1 hour. Cells were filtered twice through chiffon mesh (100 μm) and centrifuged 50 g for 5 min. Floating adipocytes were separated from pelleted S/V fraction. The infranatant fraction was removed and centrifuged at 200 g for five minutes to pellet the S/V cells.

Flow Cytometry

For metabolic syndrome experiments, the following antibodies were used for flow cytometry: anti-CD4-Pacific Blue, anti-CD8-FITC, anti-IL-17-PE, anti CD25-PercP-Cy5.5 and anti FOX3p PE-Cy725 (all from eBioscience, San Diego, Calif.). Surface staining was performed by incubating cells with antibodies and anti-CD16/32 (blocks Fc, eBioscience) at 4° C. in FACS buffer containing PBS and 0.5% BSA, for 30 min. Cells were washed twice with FACS buffer, resuspended in FACS buffer, and analyzed by flow cytometry. Appropriate isotype controls were used in all experiments. Intracellular staining was performed using Foxp3 staining buffer kit (eBioscience, San Diego, Calif.). Cells were incubated with 1 ml Fixation/Permeabilization solution for 50 min, washed twice with Permeabilization buffer and incubated with anti-Foxp3 Ab for 50 min. Cells were then washed twice with Permeabilization buffer and resuspended with FACS buffer. Analysis was performed using a FACSCalibur instrument (Becton Dickinson, San Jose, Calif.) with FCS express V.3 software (DeNovo software, Los Angeles, Calif.).

For ConA induced hepatitis experiments, flow cytometry was performed immediately following splenocyte and hepatic lymphocyte isolation using $1 \times 10^6$ lymphocytes in 100 μl PBS with 0.1% BSA. To determine the percentage of NKT lymphocytes, FITC anti-mouse CD3 and PE anti-mouse NK1.1 antibodies were used (eBioscience, USA). CD4 and CD8 subsets were detected using FITC anti-mouse CD3 and PE-anti-mouse CD4 or CD8 antibodies. Cells were incubated for 30 min at 4° C. in the dark, washed, and resuspended in 200 μl of PBS with 0.1% BSA. Analytical cell sorting was performed for $1 \times 10^6$ cells from each group using a fluorescence-activated cell sorter (FACSTAR plus, Becton Dickinson). Only live cells were counted, and unstained cells served as controls for background fluorescence. Gates were set on the forward and side scatter to exclude dead cells and red blood cells. Data were analyzed using either the Consort 30 two-color contour plot program (Becton Dickinson, Oxnard, Calif.) or the CELLQuest 25 program.

Administration of Con A and Measurement of Serum Transaminase Activities

Con A was purchased from MP Biomedicals (Ohio, USA), was dissolved (0.5 mg, 20 mg/kg) in 200 µl of 50 mM Tris pH 7, 150 mM NaCl, 4 mM $CaCl_2$, and was injected intravenously into mice (tail vain). Sera from individual mice were obtained 8 or 20 h after Con A injection. Serum activities of alanine aminotransferase (ALT) and aspartate aminotransferase (AST) were measured by an automatic analyzer.

Histological Examination

Livers from individual mice were fixed in 10% formalin, embedded in paraffin, sectioned, and stained with hematoxylin and eosin for histological examination. Specimens were examined under a light microscope.

In Vitro Stimulation of Splenocytes

Splenocytes were prepared as described above and plated at $2.0 \times 10^5$ cells per well in 96-well plates in RPMI-1640 supplemented with 5% FCS, 50 mM 2-mercaptoethanol, 2 mM glutamine, 1% sodium pyruvate, and antibiotics. Titrated volumes of GC, α-GalCer, and ALIB-97 diluted in DMSO were added at final concentrations of 100 ng, 1 µg, and 10 µg/ml. After 72 h of culture, 1 µCi of [$^3$H] thymidine (Amersham Biosciences) was added to each well, and the cells were cultured for an additional 16 to 18 h. Cells were harvested with a cell harvester (Tomtec, Orange, Conn.), and the uptake of radioactivity was measured with a β-plate reader. To evaluate IFN-γ secretion in vitro, supernatants were harvested after 90 h of culture with glycolipids and stored until the cytokine levels were measured by ELISA.

Hepatic MRI Measurement of Fat Content

Hepatic fat content is measured using a double-echo chemical shift gradient-echo magnetic resonance imaging (MRI) sequence that provides in-phase and opposed-phase images in a single acquisition for assessment/quantification of fat in mouse liver. The T1-weighted opposed-phase MR imaging technique is sensitive for detection of relatively small amounts of tissue fat. MRI images are performed with a 1.5-T system (Sigma LX; GE, Milwaukee, USA). Double-echo MR imaging is performed with a repetition time (TR) of 125 msec, double echo times (TEs) of 4 and 6.5 msec, and a flip angle of 80°. Imaging parameters include section thickness of 3 mm, 13-cm field of view, 256*160 matrix, and one signal acquired, with use of a knee coil. Transverse (axial) and coronal images are acquired at the level of the liver with a 3 mm section thickness and no intersection gap. Quantitative assessment of signal intensity (SI) measurements of SI changes between in-phase and opposed-phase images is computed as described in previous reports [Mitchell, D. G, et al., Invest. Radiol 26:1041-1052 (1991); Tomohiro, N. et al., Radiology 218:642-646 (2001)]. The SI index was calculated as follows: SI index=$(SI_{ip}-SI_{op})/SI_{ip}$, where $SI_{ip}$ is SI on in-phase images and $SI_{op}$ is SI on opposed-phase images. The SI index reflects the fraction of SI loss on opposed phase images compared with the SI on in-phase images.

PC-12 Cell Culture

PC-12 cells are grown in Dulbecco's modified Eagle's medium (DMEM) supplemented with 5% fetal calf serum, 10% horse serum, 100 µg/ml streptomycin, and 100 U/ml penicillin. The cultures are maintained in an incubator at 37° C. in a humidified atmosphere of 5% $CO_2$. $5 \times 10^4$ cells/ml are cultured in 24-well plates. Cells are subjected to neurotoxins and neuroprotection tests as described below.

Treatment of PC-12 with Neurotoxins

For A β toxicity, Aβ (25-35) peptide (1-2 µM final concentration) is incubated for 10 minutes at 37° C. before added to cells.

For cholesterol toxicity 5 µM cholesterol are added to the medium. *Serum-free cytotoxicity is tested growing the cells in the medium without serum supplement.

Induction of Experimental Colitis 2,4,6-trinitrobenzene sulfonic acid (TNBS) (Sigma)—colitis is induced by intrarectal installation of TNBS, 1 mg/mouse, dissolved in 100 ml of 50% ethanol as described [Collins, C., et al., Eur. J. Immunol. 26:3114-3118 (1996)].

Clinical Assessment of Colitis

Diarrhea is followed daily throughout the study.

Macroscopic Score of Colitis

Colitis assessment is performed 14 days following colitis induction using standard parameters [Madsen, K. L., et al., Gastroenterology 113:151-159 (1997); Trop, S., et al., Hepatology 27:746-755 (1999)].

Four macroscopic parameters are determined, namely: degree of colonic ulcerations, intestinal and peritoneal adhesions, wall thickness and degree of mucosal edema. Each parameter is graded on a scale from 0 (completely normal) to 4 (most severe) by two experienced blinded examiners.

Grading of Histological Lesions

For histological evaluation of inflammation, distal colonic tissue (last 10 cm) is removed and fixed in 10% formaldehyde. Five paraffin sections from each mouse are then stained with hematoxyllin-eosin by using standard techniques. The degree of inflammation on microscopic cross sections of the colon is graded semiquantitatively from 0 to 4 [Madsen et al., (1997) ibid.; Trop et al., Hepatology 27:746-755 (1999)]. Grade 0: normal with no signs of inflammation; Grade 1: very low level of leukocyte infiltration; Grade 2: low level of leukocyte infiltration; and Grade 3: high level of infiltration with high vascular density, and bowel wall thickening; Grade 4: transmural infiltrates with loss of goblet cells, high vascular density, wall thickening, and disruption of normal bowel architecture. The grading is performed by two experienced blinded examiners.

Model for PD

The neurotoxin 6OHDA (8 µM/rat) is stereotaxically injected in 4 µl into the right substantia nigra of male Sprague-Dawley rats (weighing 250-270 g), for induction of nigral lesion. This animal model show PD-related clinical symptoms within 3 days following 6OHDA injection.

*Stepping Adjustments Test

The number of stepping adjustments is counted for each forelimb during slow sideway movements in forehand and backhand directions over a standard flat surface. The stepping adjustments test is repeated three times for each forelimb.

*Forelimb Placing Test

The forelimb-placing test assesses the rats' ability to make directed forelimb movements in response to a sensory stimulus. Rats are held with their limbs hanging unsupported. They are then raised to the side of a table so that their whiskers make contact with the top surface while the length of their body parallels the edge of the tabletop. Control rats place their forelimb on the tabletop in response to whisker stimulation almost every time, whereas injured rats do not. Each test includes 10 trials of placement of each forelimb and is repeated daily for three consecutive days. The results of both tests are expressed as percentage of forelimb stepping adjustments and placing in the lesioned side, as compared with the nonlesioned side. ANOVA analysis of repeated measures is used to determine significant differences in the motor performance.

*At the end of experiment striata of the animals are collected, and submitted to HPLC analysis for the presence of dopamine and its metabolites 3,4-dihydroxyphenylacetic acid (DOPAC), and homovanillic acid (HVA). The levels of dopamine and metabolites in the lesioned side of the treated animals (relative to the nonlesioned side) are compared to the non-treated animals.

In addition, in some of the animal's brain sections are submitted to immunohistochemistry analysis for tyrosine hydroxylase (TH), a rate-limiting enzyme for dopamine synthesis, which serves as an important marker of dopaminergic cell loss.

Model for ALS

Transgenic mice expressing the human G93A SOD1 (B6SJL-TgN[SOD1-G93A]1Gur), are used. These tg mice model show ALS related clinical symptoms starting at about 14-15 weeks of age, and die at about 18-20 weeks.

Mice are treated with different concentrations of synthetic β-glycolipid derivatives such as the compounds of Formula II, III and IV, in drinking water, starting at week 8 of age (N=7), versus non-treated mice as controls (N=6).

*"Rotarod" Motor Function Test

Mice are weekly tested for motor function using a "Rotarod" device (Panlab, Barcelona) to detect onset and progression of disease-related weakness. The mice are placed on a rotating cylinder with a constant rate of acceleration. When the mice can no longer continue running and fall from the cylinder, the total time they spend on the cylinder and final speed achieved is recorded electronically, thus allowing calculation of the total distance run. Each mouse performs three rotarod trials, and the best performance each week is recorded. A "baseline" distance is established at 12 weeks of age to which subsequent performance is compared. Onset of disease-related weakness is defined as a sustained decrease of more than 30% of baseline maximum running distance. Survival is defined by an accepted artificial endpoint as the time at which the mouse is no longer able to right itself within 30 seconds of being placed on its side.

A clinical 5-point score is used for assessing the ability to move:

4=normal mobility; 3=movement with limited use of the hindlegs; 2=movement with the use of the forelegs; 1=movement only for a short period with the use of the forelegs; and 0=unable to move.

The time to onset and death/survival of treated and control groups are compared using Kaplen-Meier curve analysis (using SPS 12 for Windows®). ANOVA analysis of repeated measures is used to determine significant differences in the motor performance.

Statistical Analysis

Statistical analysis was performed using the student t test. $P \leq 0.05$ was considered significant.

Example 1

Synthesis of β Glycolipids Analogs

Three synthetic novel analogs of β glycolipids, namely AD2897 (ALIB-97), AD2898, and AD2899, were synthesized using the following protocols:

AD2897—(ALIB-97) N-adamantyl-N'-glucosylsphingosine thiourea also indicated as Formula II, was synthesized as follows:

50 mg of β-Glucosylsphingosine were "dissolved" in 50 ml of 0.5N carbonate buffer pH=9. 21 mg 1-Adamantyl isothiocyanate in 30 ml of 0.5N carbonate buffer pH=9 were added. The mixture was stirred overnight at room temperature, evaporated to dryness and the residue dissolved in dichloromethane/methanol, 2:1 (50 ml). 30 ml 0.5N HCl were then added slowly and the mixture transferred to a separatory funnel. The upper phase was removed and another amount of 30 ml HCl was added. The product was washed with a $3^{rd}$ amount of HCl and then twice with $H_2O$. The organic phase was dried on $MgSO_4$, filtered and evaporated to dryness in a rotavapor. The product was then purified by silica gel column chromatography using increasing concentrations of methanol in dichloromethane. The fractions containing the pure compound (as indicated by HPLC) were pooled and evaporated to dryness. The residue was suspended in $H_2O$ and lyophilized to obtain a 50% yield.

FIG. 6 shows the structure of this particular analog (ALIB-97) that was analyzed in detail as described in Examples 3 and 4.

AD2898—Octyl-sulfonamido-glucosylsphingosine, (Glucosylsphingosine-octylsulfonamide) also indicated as Formula III, was synthesized as follows:

Two mg β-Glucosylsphingosine were dissolve in a mixture of 5 ml Ethanol and 5 ml 0.5N carbonate buffer pH=10. 1 mg octane sulfonylchloride was added. The mixture was stirred overnight at room temperature, then evaporated to dryness and the residue dissolved in dichloromethane/methanol, 2:1 (5 ml). 3 ml 0.5N $NaHCO_3$ were added slowly and the mixture transferred to a small separatory funnel. The upper phase removed and another amount of 3 ml $NaHCO_3$ was added. The product was washed with a $3^{rd}$ amount of sodium bicarbonate and then twice with $H_2O$. The organic phase was dried on $MgSO_4$, filtered and evaporated to dryness by a stream of nitrogen. The product was purified by silica gel column chromatography using increasing concentrations of methanol in dichloromethane. The fraction containing the pure compound (as indicated by HPLC) was evaporated to dryness. The residue was suspended in $H_2O$ and lyophilized.

AD2899: Hexadecyl-sulfonamido-glucosylsphingosine, (Glucosylsphingosine-hexadecylsulfonamide) also indicated as Formula IV, was synthesized as follows:

Two mg β-Glucosylsphingosine were dissolve in a mixture of 5 ml Ethanol and 5 ml 0.5N carbonate buffer pH=10. 1 mg hexadecanoylsulfonyl chloride was added. The mixture was stirred overnight at room temperature, then evaporated to dryness and the residue dissolved in dichloromethane/methanol, 2:1 (5 ml). 3 ml 0.5N NaHCO$_3$ were added slowly and the mixture transferred to a small separatory funnel. The upper phase removed and another amount of 3 ml NaHCO$_3$ was added. The product was washed with a 3$^{rd}$ amount of sodium bicarbonate and then twice with H$_2$O. The organic phase was dried on MgSO$_4$, filtered and evaporated to dryness by a stream of nitrogen. The product was purified by a silica gel column chromatography using increasing concentrations of methanol in dichloromethane. The fraction containing the pure compound (as indicated by HPLC) was evaporated to dryness. The residue was suspended in H$_2$O and lyophilized.

The analogs were Formulated in solvent containing 15% Cremophor EL/15% ethanol/70% PBS, prior to use.

Example 2

Effect of Novel Synthetic β Glycolipids on ConA Induced Immune Mediated Hepatitis To determine the clinical and immunological effect of the novel synthetic compounds of the invention, immune-mediated hepatitis was examined using the ConA induced hepatitis model. Therefore, the different synthetic and natural derivatives of β-glycolipids of Formula II, III and IV [AD2897 (ALIB-97), AD2898, and AD2899, respectively], were examined using seven groups of C57Bl/6 mice, as summarized by Table 1. Mice in experimental groups A-G (eight mice in each group) were injected with ConA. Group A mice were administered with 100 μl intraperitoneal injection of solvent only [15% Cremophor EL/15% ethanol/70% PBS] (C:E). Mice in groups B, C, D, E, F, and G were administered with intraperitoneal injection of 1 μg or 10 μg of each of the three analogs Formulated in solvent as described in Experimental Procedures. Animals were sacrificed and examined.

In order to evaluate the potential beneficial effect of the three novel analogues of the invention on immune-mediated hepatitis, the effect of treatment with two concentrations of the three synthetic analogs on liver damage in all tested groups was assessed by determination of serum aspartate aminotransferase (AST), and alanine aminotransferase (ALT) levels.

Figure 1:
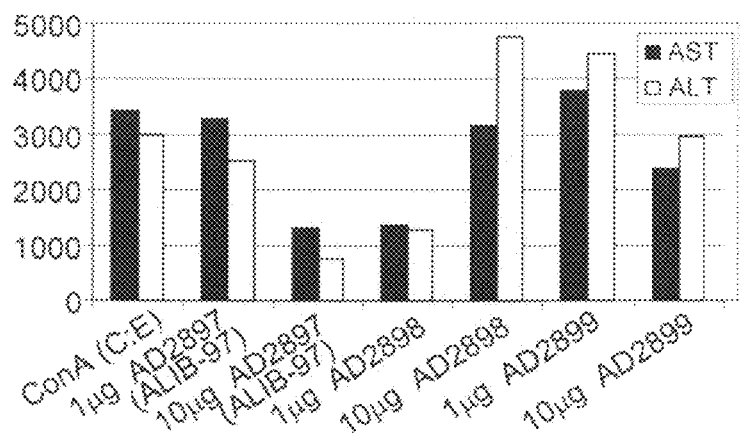
FIG. 1 The novel GC analogs decrease liver injury

As clearly shown by FIG. 1, both ALT and AST levels decreased in animals treated using either AD2897 (ALIB-97) or AD2898 as synthetic analogs, with the former requiring the administration of a 10 μg dosage and the later only a 1 μg dosage. As these liver transaminases provide evidence for hepatic cell injury their decrease in the serum suggest the alleviation of liver damage and immune mediated liver injury.

Assessment of the effect of any of the synthetic analogs on the immune response was next determined by analysis of the cytokine serum level of IFNγ in each animal using a commercial "sandwich" ELISA kit, and by FACS analysis of intrahepatic and intrasplenic (peripheral) lymphocytes levels.

As shown by FIG. 2, mice treated with either AD2898 or AD2899 in both high and low dosages or with a low dosage of AD2897 (ALIB-97), exhibited a decrease in IFNγ serum levels, suggesting a negative effect upon this pro-inflammatory cytokine.

Treatment of animals with a low dosage of the AD2897 analog, a low dosage of the AD2898 analog or a high dosage of the AD2899 analog resulted in a decrease in intrahepatic NKT cell levels and a decrease in the intrahepatic/peripheral ratio of these lymphocytes (FIGS. 3 and 4, respectively). A similar corresponding increase was observed in the peripheral/intrahepatic ratio of the CD4/CD8 ratio (FIG. 5).

Taken together these results indicate that the three novel synthetic β-glycolipids analogs of the invention, AD2897 (ALIB-97), AD2898, and AD2899 (Formula II, III and IV, respectively) are capable of exerting an immunomodulatory effect upon the immune system of animals suffering from immune mediated liver injury.

TABLE 1

| Group: | Treatment |
| --- | --- |
| A | Con A (C:E) |
| B | AD2897 1 μg/mice |
| C | AD2897 10 μg/mice |
| D | AD2898 1 μg/mice |
| E | AD2898 10 μg/mice |
| F | AD2899 1 μg/mice |
| G | AD2899 10 μg/mice |

Example 3

ALIB-97 Ameliorates ConA Induced Hepatitis by Suppressing Type INK T Cells

I. Oral Administration of ALIB-97 Decreased Intrahepatic and Intrasplenic NKT Lymphocytes in B6 Mice As shown by the previous Examples, the different novel analogs clearly affect different immune cell populations in diseased animals. To further investigate the effect of one of the novel analogs of the invention, the ALIB-97 derivative, on spleen and liver cell populations, B6 mice were used by the inventors as control animals. As shown by FIG. 7A, oral administration of ALIB-97 resulted in a significant decrease in hepatic CD3/NK1.1 lymphocytes after 8 hours (73%, p<0.05), as well as in the CD3/CD4 lymphocyte ratio (20%, p=0.08). Hepatic CD3/CD8 lymphocytes were unaffected. In the spleen, reduction of CD3/CD8 and CD3/CD4 cells was observed (30%, p<0.05; and 23%, p=0.07, respectively), and splenic CD3/NK1.1 lymphocytes were markedly increased (>100%, p<0.05). FIGS. 7B and 7C demonstrate the effect of intraperitoneal ALIB-97 administration at 8 and 20 h, respectively. At 8 h, ALIB-97 significantly reduced splenic CD3/CD4 and CD3/NKT cells (p<0.05 and <0.01, respectively). Hepatic CD3/NKT cells were decreased by more than 55% (p<0.05). At 20 h, hepatic CD3/CD4 cells increased by 33% (p=0.01), whereas splenic CD3/CD4 cells were not affected. Taken together, as also shown by Example 2, oral administration of ALIB-97 resulted in a significant decrease in intrahepatic and intrasplenic NKT lymphocytes in healthy B6 mice.

II. Oral Administration of ALIB-97 Ameliorated Con A Hepatitis in B6 Mice

Since abnormalities in NK T cell populations were previously demonstrated in patients with autoimmune disorders, the inventors further examined in detail the observed effect of ALIB-97 on NK T cell population, and the applicability of this effect in amelioration of autoimmune diseases, such as the ConA induced hepatitis. Injection of Con A into mice is known as resulting in elevation of serum ALT and AST levels after approximately six hours. The elevated ALT and AST levels peak between twelve and twenty four hours [Biburger, M. and Tiegs, G. J. Immunol. 175: 1540-50 (2005)]. The inventors therefore examined the levels of these enzymes in B6 mice twenty hours after Con A injection (22 h after oral administration of β-GC and ALIB-97). As was also shown (Example 2) for all three analogs, FIG. 8A demonstrates that serum AST and ALT levels were significantly reduced following oral administration of ALIB-97 compared with the control ($p<0.01$). The effect was equivalent to that of dexamethasone and greater than that of the natural β-GC ($p<0.05$).

III. IP Administration of ALIB-97 Ameliorated Con A Hepatitis in B6, but not in CD1d and Jα18 KO, Mice To examine whether the beneficial effect of ALIB-97 on ConA induced hepatitis was mediated by type I or type II NKT cells, the Jα18−/− and CD1d−/− mice were used. Both Jα18−/− and CD1d−/− mice that lack iNKT cells are known to be relatively resistant to Con A-induced hepatic injury [Kaneko, Y. et al. J. Exp. Med. 191: 105-14 (2000); Takeda, K. et al. Proc. Natl. Acad. Sci. U.S.A. 97: 5498-503 (2000)]. The inventors therefore compared the effects of β-GC and ALIB-97 between B6 and both Jα18−/− and CD1d−/− mice. FIG. 8B shows that Jα18−/− and CD1d−/− mice were indeed relatively resistant to Con A-induced hepatitis, and ALIB-97 did not significantly alter the enzyme levels in these mice. However, intraperitoneal administration (IP) of ALIB-97 to B6 mice significantly reduced AST and ALT levels by more than 60% ($p<0.05$). FIG. 8C shows that the histological findings of degenerative changes in the liver correlate with serum aminotransferase levels.

IV. In Vitro Stimulation of Splenocytes

The inventors next studied in vitro splenocyte cytokine polarization resulting from NKT cell stimulation by β-glycolipids. FIG. 9 shows proliferation by [$^3$H] thymidine incorporation and supernatant IFN-γ levels that were measured over a range of β-glycolipid concentrations. The glycolipid ALIB-97 differed structurally from β-GC by having an adamantanyl residue instead of the fatty acid chain, and also by the feature of replacement of the amide bond with a thiocarbamide (thiourea) bond. FIG. 9B (III) shows that despite these modifications, 100 ng of ALIB-79 activated IFN-γ secretion more than 9-fold in mouse splenocytes. This cytokine activation was even higher than that induced by αGalCer. The response was iNKT cell-dependent, as demonstrated by the absence of these effects in both Jα18−/− and CD1d−/− mice. Interestingly, GC was the sole glycolipid capable of activating IFN-γ secretion in CD1d−/− splenocytes. However, as shown in FIGS. 9A and 9B, cell proliferation was not activated by either β-glycolipid, in contrast to αGalCer, which induced cell proliferation in B6 splenocytes.

V. Oral Administration of ALIB-97 Decreased IFN-γ and IL-10 Serum Levels in B6 Mice One hallmark of iNKT cells is their capacity to produce, within hours of activation, large amounts of cytokines, including the characteristic Th1 cytokine IFN-γ. The inventors next determined the effects of orally administered ALIB-97 on serum cytokines after 20 hours. FIG. 10A shows that oral administration of ALIB-97 to B6 mice resulted in a significant decrease in serum IFN-γ levels compared to the control ($p<0.01$). This change was greater than that induced by dexamethasone and β-GC ($p=0.05$). Orally administered ALIB-97 also affected the serum levels of the immunosuppressive cytokine IL-10 to a greater extant than that observed in response to dexamethasone ($p<0.01$, FIG. 10B).

VI. IP Administration of ALIB-97 Affects Serum Cytokine Secretion

Administration of α-GalCer to mice was previously shown as resulting in significant amounts of IFN-γ in the serum of wild type but not CD1d-deficient animals [Singh, A. K. et al. J. Exp. Med. 194: 1801-11 (2001)]. Next, the inventors determined whether IP administration of ALIB-97 had similar effects on several serum cytokines when compared with oral administration. FIG. 10C. shows that intraperitoneal administration of ALIB-97 caused a marked decrease in serum IFN-γ levels in B6, but not in CD1d−/−, mice. However, in Jα18−/− mice, which have only type II NKT cells, a substantial increase in serum IFN-γ was observed. Serum IL-10, a pro-inflammatory cytokine, was increased following the injection of ALIB-97 in B6, CD1d−/−, and Jα18−/− mice, suggesting a general iNKT mechanism. The inventors further assessed the secretion of two other pro-inflammatory cytokines: TNF-α and IL-6. Serum TNF-α is known to be associated with the mechanism of Con A-induced hepatitis. ALIB-97 had a modest effect on serum TNF-α secretion in B6 mice. Interestingly, the levels of TNF-α were twice as high in both KO mice compared to B6 mice. These levels were decreased following ALIB-97 administration. Serum IL-6 levels were reduced after the injection of ALIB-97 in all three strains of mice. ALIB-97 did not affect the serum levels of IL-4 (data not shown).

VII. IP Administration of ALIB-97 Reduced STAT1 and STAT4 Phosphorylation and Increased the Expression of STAT6 in the Liver To further analyze the potential signal transduction pathways affected by the novel ALIB-97 derivative, phosphorylation of STAT proteins was next examined. FIG. 11A shows the effect of ALIB-97 on several signal transducers and activators of transcription (STAT) proteins in the liver. ALIB-97 increased STAT1 phosphorylation of Tyr 701 in the liver both in B6 and in CD1d−/− mice. STAT6 expression was slightly increased by ALIB-97. However, the endogenous expression of STAT6 in CD1d−/− mice was relatively low, and ALIB-97 markedly induced that expression. FIG. 11B shows that STAT4 expression was strikingly decreased in B6 mice, but remained unchanged in CD1d−/− mice.

Taken together, the ALIB-97 analog was shown by the invention as associated with a potent immune modulatory effect via suppression of type I NK T cells, suggesting that it may serve as an anti-inflammatory agent in NKT-dependent disorders.

Example 4

Use of ALIB-97 for the Treatment of Metabolic Syndrome Associated Disorders

I. ALIB-97, the Novel β-Glycolipide Derivative Alters the Activation of JNK2 and AKT and Therefore is Applicable for Treatment of Metabolic Syndrome Associated Disorders c-Jun N-terminal kinase (JNK) is a member of the subfamily of mitogen-activated protein kinases (MAPKs), and plays a role in obesity and insulin resistance. Insulin resistance is closely associated with chronic inflammation characterized by activation of a network of inflammatory signaling pathways. Alpha and beta-glycosphingolipids were previously described as having an immune-modulatory role, particularly via promotion of Tregs and modulation of their distribution. The inventors therefore examined the potential of the newly synthesized β-glycosphingolipid analogue (ALIB-97) as a modulator of the JNK pathway as a mean to alleviate insulin resistance, by alteration of adipose tissue and stromal tissue derived Tregs.

Therefore, five groups of male C57BL/6 Ob/Ob mice were studied. Mice (6 per group) were fed (per os) daily for 4 weeks with 15 or 45 μg of GC (groups B and C, respectively) and 15 or 45 μg of ALIB-97 (groups D and E, respectively). Control mice (Group A) were administered vehicle only.

Western blots of liver extracts prepared from all experimental groups were analyzed for JNK and AKT activation. As shown by FIG. 12A, JNK2 activation was increased in all studied groups compared to control group. The high dose of 45 μg of GC (group C) resulted in 60% activation of JNK2. Akt is involved in insulin stimulation and glucose transport [Hajduch, 2000], the inventors next examined the effect of ALIB-97 on AKT phosphorylation. FIG. 12B shows that AKT activation was also increased in all groups except for group D where it was decreased. The maximal effect was, again, demonstrated in group C, where AKT activation was increased by 43%.

These results clearly demonstrate that the novel β-glycolipide derivative alters the activation of JNK2 and AKT and therefore may be applicable for treatment of metabolic syndrome associated disorders.

II. ALIB 97 Induces Tregs in Adipose Tissue and in the Adipose-Tissue Associated Stromal Vasculature Obesity is known to induce inflammation derived from adipose tissue. Encouraged by the observe effect of the ALIB-97 derivative on the JNK pathway, the inventors next characterized the effect of this novel derivative on numbers and subsets of fat-associated T cells from adipose tissue and the spleen. Table 2 summarizes the main effects in these organs after administration of ALIB-97, as observed by flow cytometry. A significant alteration was demonstrated in several T cell sub-populations at various organs. Classical Tregs (CD4+ CD25+FOXP3+) in the adipose tissue were significantly induced (FIG. 13A), while CD8+ CD25+FOXP3+ were increased in the spleen. This was associated with a decrease in splenic CD4+FOXP3+ and adipocytic both CD4+ and CD8+ FOXP3+IL17+ cells. Another interesting aspect of changes in the distribution of lymphocyte sub-population, was derived from the inspection of cell ratios between CD4+ IL17+ lymphocytes (associated with autoimmunity) and CD4+CD25+ lymphocytes (associated with immune tolerance) and CD4+ CD25+FOXP3+. When comparing the spleen, adipose tissue and stromal vasculature, the adipose tissue alone had a baseline ratio >1 (leaning towards inflammation). A reversal of this ratio towards tolerance was achieved using GC (FIG. 13B). In a more specific inspection, when examining the ratio between CD4+IL17+ and CD4+ CD25+FOXP3+ cells, again, the smallest ratio towards tolerance was found in the adipose tissue compared with the stromal vasculature and spleen (FIG. 13C). GC administration resulted in a dose dependent shift towards tolerance. This effect is organ specific and was not demonstrated in the neither the spleen nor the stromal vasculature.

TABLE 2

|  | ADIPOCYTES | SVC | SPLEEN |
| --- | --- | --- | --- |
| CD4+IL17+ | ↓ | | |
| CD4+FOXP3+IL17+ | ↓ | | |
| CD4+CD25+FOXP3+ | ↑↑ | | |
| CD4+CD25+IL17+ | | ↑ | |
| CD4+FOXP3+ | | | ↓ |
| CD25+FOXP3+ | | | ↓ |
| CD8+CD25+ | ↓ | | |
| CD8+IL17+ | ↓ | | |
| CD8+FOXP3+IL17 | ↓↓ | | |
| CD8+CD25+FOXP3+IL17+ | ↓ | | ↑ |
| CD8+CD25+IL17+ | ↑ | ↑ | |
| CD8+CD25+FOXP3+ | | ↓ | ↑↑ |
| CD8+FOXP3+ | | | ↑↑ |

Table 2 summarizes the effect of 45 μg ALIB-97 on CD4+ and CD8+ cells at the spleen, adipose tissue and stromal vascular cells (SVC) compared with vehicle (↓/↑ and ↓↓/↑↑- $p \leq 0.05$ and $p \leq 0.01$ respectively)

III. Alteration of Tregs in Adipose Tissue Alleviates the Insulin Resistance

Induction of Tregs in adipose tissue may lead to alleviation in insulin resistance. Therefore, the inventors next examined the effect of GC and the novel ALIB-97 derivative using glucose tolerance test (GTT) as reflecting insulin resistance. As demonstrated by FIG. 14, β-glycolipid treatment for four weeks resulted in lower fasting blood glucose ($p \leq 0.001$ for all study groups). Additionally, glucose tolerance test (GTT) showed decreased insulin resistance as manifested by lower post prandial glucose levels (FIG. 14A). When each time-point of glucose levels was calculated in respect to the initial levels (time 0) in each group prior to glucose loading, the decrease in glucose levels reached statistical significance at 60 minutes in group E (45 μg ALIB-97), 90 minutes in group D (15 μg ALIB-97) and 120 minutes in groups B and C (15 and 45 μg GC, respectively), meaning an earlier effect in ALIB-97 treated mice compared with GC treated. Interestingly, the decrease in glucose levels was dose dependent, as for both types of glycolipids lower glucose level were achieved in higher doses (groups C and E). None of the study groups had a significant change in insulin levels (FIG. 14B), thus indicating the effect of lower blood glucose levels to be a result of decreased insulin resistance.

IV. ALIB-97 Induced Alteration of Tregs in Adipose Tissue Alleviates the Liver Injury in NASH The inventors next examined whether the observed alleviation of insulin resistance caused by ALIB-97 induced alteration of Tregs may be applicable also in alleviating liver injury. Therefore, all experimental groups where tested for ALT and AST serum levels. FIG. 15 shows that both β-glycolipids (ALIB-97 and GC) significantly reduced AST (710 in group A vs. 330, 289 and 124 u/L in groups C, D (p=0.01) and E respectively (p<0.01). 45 µg of ALIB-97 also significantly reduced ALT (370 in group A vs. 165 u/L in group E, respectively, p<0.05).

V. Alteration of Tregs in Adipose Tissue Improves Serum TGs Profile

The inventors further examined the effect of ALIB-97 on serum TG. As demonstrated by FIG. 16, mice in all treated groups exhibited a significant decrease in their serum triglycerides (TGs), compare to control mice. However, serum cholesterol was not affected by the studied β-glycolipids. Also when the effect of β-glycolipids on intra hepatic TGs, was examined, no change was observed (data not shown).

Other parameters examined, for example, TGF-β levels, initial or sacrifice weight and body/liver weight ratio showed no significant difference among the tested groups.

In summary, the ALIB-97 novel derivative of the invention was shown herein as alleviating insulin resistance, reducing hepatic damage as reflected by reduction of serum levels of ALT and AST, and reducing serum TG. These effects are presumably mediated by induction of the JNK2 pathway and alteration of hepatic Tregs by the novel ALIB-97 derivative. These results demonstrate the feasibility of using such derivative for treating metabolic syndrome and disorders associated therewith.

Example 5

Mixed Synthetic Derivatives of β-glycolipids in Diabetic *Psammomys* Model

To determine the effect of different combinations of synthetic derivatives of β-glycolipids, and particularly of the compounds of Formula II, III and IV as well as of mixtures thereof, on diabetes, metabolic syndrome and hepatic steatosis, the diabetic Passamon model is used. The sand rat (*Psammomys obesus*), a model of nutritionally-induced type II diabetes, develops significant Hyperinsulinemia, hyperglycemia and hypertriglyceridemia on a high-energy diet. Seven groups of five-month-old sand rats on high energy diets are studied (n=10 per group). Animals are treated by daily intraperitoneal injections of the compound of Formula I (group A), the compound of Formula III (group B), the compound of Formula IV (group C), a mixture of the compounds of Formula II+III (group D), a mixture of the compounds of Formula II+IV (group E), a mixture of compounds of Formula III+IV (group F) or PBS (group G), for 25 days. On day 25, all *psammomys* are sacrificed and examined.

Determination of hepatic fat content and inflammation is performed by magnetic resonance imaging (MRI), examination of liver biopsies and measurement of serum Alanine aminotransferase (ALT) and Aspartate aminotransferase (AST) levels. Body weight and post prandial serum glucose, insulin, triglyceride and free fatty acid (FFA) levels are assessed. To determine the mechanism of the effect of these derivatives on the Th1/Th2 balance, expression of the transcription factors STAT1, STAT4, STAT5 and STAT6 is determined in splenocytes.

Example 6

The Effect of Synthetic Derivatives of β-glycolipids on Non Alcoholic Fatty Liver Disease (NAFLD) and the Metabolic Syndrome Using the Diabetic Cohen Rat Model To determine the effect of mixtures of different synthetic derivatives of β-glycolipids on diabetes, hepatic steatosis and metabolic syndrome, the Cohen rat model is used by the inventors. The Cohen rat is a lean, non-insulin resistant model of type 2 diabetes that features zone 1 and 2 mixed micro and macrovesicular steatosis and elevated serum transaminases.

Seven groups of Cohen rats are studied (n=10/group). Animals are treated by daily intraperitoneal injections of the compound of Formula II (group A), the compound of Formula III (group B), the compound of Formula IV (group C), a mixture of the compounds of Formula II+III (group D), a mixture of the compounds of Formula II+IV (group E), a mixture of compounds of Formula III+IV (group F) or PBS (group G), for 45 days. Assessment of NAFLD is performed by MR imaging, examination of liver biopsies and measurement of serum transaminases. Metabolic follow up parameters included body weight, oral glucose tolerance test (OGTT), serum lipids and pancreatic histology. Immune modulation is assessed by FACS analysis of intrahepatic and intrasplenic lymphocytes.

Example 7

Treatment of Immune Mediated Colitis

I. Use of the Compounds of Formula II, III and IV for Treatment of Immune Mediated Colitis To determine the clinical and immunological effect of administration of different synthetic and natural derivatives of β-glycolipids such as the compounds of Formula II, III and IV, on a murine model of experimental colitis, eight groups of C57Bl/6 mice, consisting of 10 mice each, are studied. Table 3 summarizes the experimental groups. Colitis is induced by intracolonic installation of trinitrobenzenesulfonic acid (TNBS) on day 1 and 5 in groups A-D. Group A mice are fed regular chow diet. Group B-D mice receive oral (PO) daily of the compounds of Formula II, III and IV, respectively. Groups E-G mice are not treated with TNBS, but receive oral (PO) daily amount of the compounds of Formula II, III and IV, respectively, and serve as control groups.

Mice are followed for macroscopic and microscopic colitis scores. The immunemodulatory effect of GC is determined by FACS analysis of intrahepatic and intrasplenic lymphocytes for NKT, CD4 and CD8 markers, and by measurement of serum IFNγ, IL2, IL12, IL4 and IL10 cytokine levels.

TABLE 3

| Group: | Treatment: |
|---|---|
| A | TNBS |
| B | TNBS with OP compound of Formula I |
| C | TNBS with OP compounds of Formula II |
| D | TNBS with OP compounds of Formula III |
| E | TNBS with OP compounds of Formula I |
| F | OP compounds of Formula II |
| G | OP compounds of Formula III |
| H | OP PBS |

II. Synergistic Effect for Different Mixtures of the Compounds of Formula II, III and IV in the Treatment of Immune Mediated Colitis To determine the possible immuno-modulation effect of different mixtures of the different synthetic derivatives of β-glycolipids, the effect of mixtures of the compounds of Formula II, III and IV is tested using a murine model of colitis.

As summarized in Table 4, seven groups of mice are studied, each consisting of 10 mice. Colitis is induced by intracolonic installation of trinitrobenzenesulfonic acid (TNBS) on day 1 and 5 in groups A to D. Group A mice are fed regular chow diet. Groups B and E mice receive oral (PO) daily amount of a mixture of the compounds of Formula II and III, groups C and F receive a mixture of the compounds of Formula II and IV, groups D and G mice receive oral (PO) daily amount of a mixture of the compounds of Formula III and IV. Groups E to G mice are not treated with TNBS, but receive oral (PO) daily amount of a mixture of Groups B and E mice receive oral (PO) daily amount of a mixture of the compounds of Formula II, III and IV, as described above, and serve as control groups.

Mice are followed for macroscopic and microscopic colitis scores, as well as for survival and functional status and weight.

TABLE 4

| Group: | Treatment: |
|---|---|
| A | TNBS |
| B | TNBS with compounds of Formula II and III (1:1) |
| C | TNBS with compounds of Formula II and IV |
| D | TNBS with compounds of Formula III and IV |
| E | compounds of Formula II and III (1:1) |
| F | compounds of Formula II and IV |
| G | compounds of Formula III and IV |

The immune modulatory effect of beta-glycolipids is determined by FACS analysis of intrahepatic and intrasplenic lymphocytes for NKT, CD4 and CD8 markers, and by measurement of serum cytokine levels.

III. Different Mixtures of Compounds of Formula I, II and III in Colitis-Determination of Different Mixture Ratios To test different combinations of the different synthetic β-glycolipids derivatives, and to identify the most effective mixture combination, different quantitative ratio of the compounds of Formula II, III and IV are checked (1:1, 1:10, and 1:100), using the murine model of colitis.

As summarized in Table 4, sixteen groups of C57BL mice are studied, each consisting of 10 mice. Colitis is induced by intracolonic installation of trinitrobenzenesulfonic acid (TNBS) on day 1 and 5 in all groups. Group A mice are fed regular chow diet. Groups B-F mice receive oral (PO) daily amount of a mixture of the compounds of Formula II and III in different ratio, groups G-K receive a mixture of the compounds of Formula II and IV in different ratio and groups L-P receive a mixture of the compounds of Formula III and IV in different ratio as indicated by the table.

Mice are followed for macroscopic and microscopic colitis scores, as well as for different cell populations by FACS: CD4, CD8, NKT in spleen and liver (not pooled), and for serum cytokines IFNγ and IL4 by ELISA.

TABLE 5

| Group | Day 1 and 5 | Day 1-9 feeding |
|---|---|---|
| A | TNBS 0.5 mg × 2 | — |
| B | TNBS 0.5 mg × 2 | Compounds of Formula II and III (1:1) |
| C | TNBS 0.5 mg × 2 | Compounds of Formula II and III (1:10) |
| D | TNBS 0.5 mg × 2 | Compounds of Formula II and III (1:100) |
| E | TNBS 0.5 mg × 2 | Compounds of Formula III and II (1:10) |
| F | TNBS 0.5 mg × 2 | Compounds of Formula III and II (1:100) |
| G | TNBS 0.5 mg × 2 | Compounds of Formula II and IV (1:1) |
| H | TNBS 0.5 mg × 2 | Compounds of Formula I and III (1:10) |
| I | TNBS 0.5 mg × 2 | Compounds of Formula II and IV (1:100) |
| J | | Compounds of Formula IV and II (1:10) |
| K | | Compounds of Formula IV and II (1:100) |
| L | | Compounds of Formula III and IV (1:1) |
| M | | Compounds of Formula III and IV (1:10) |
| N | | Compounds of Formula III and IV (1:100) |
| O | | Compounds of Formula IV and III (1:10) |
| P | | Compounds of Formula IV and III (1:100) |

Example 8

I. Use of the Compounds of Formula II, III and IV For the Treatment of Immune Hepatocellular Carcinoma The immunomodulatory effect of different synthetic derivatives of β-glycolipids and particularly of the compounds of Formula II, III and IV, demonstrated by the ConA induce hepatitis model, encouraged the inventors to further investigate other immune-related disorders, such as hepatocellular carcinoma (HCC). Therefore, the clinical and immunological consequences of administration of the compounds of Formula I, II and III on hepatocellular carcinoma (HCC) are next examined, using mice transplanted with human Hep3B HCC. Four groups of athymic Balb/c mice, consisting of 8 mice each, are sub lethally irradiated and transplanted with human Hep3B HCC, followed by daily intraperitoneal injections of the compounds of Formula II, III and IV, (in 100 μl PBS) or PBS (100μ for 25 days. Animals are followed for tumor size and weight and for intrahepatic and intrasplenic lymphocyte subpopulations, serum cytokine levels and expression of STAT1, STAT4 and STAT6 in splenocytes. The different test groups are summarized in Table 6.

TABLE 6

| Group: | Treatment: |
|---|---|
| A | Hep3B HCC, the compound of Formula II |
| B | Hep3B HCC, the compound of Formula III |
| C | Hep3B HCC, the compound of Formula IV |
| D | Hep3B HCC, PBS control |

II. Effect of Mixtures of β-Glycolipids on the Treatment of Immune Hepatocellular Carcinoma The inventors further analyze the effect of different combinations of synthetic derivatives of β-glycolipids, and particularly of mixtures of the compounds of Formula II, III and IV, which are shown effective in the ConA hepatitis model, by using the murine HCC model.

Athymic Balb/c mice (n=8/group) are sub lethally irradiated and transplanted with human Hep3B HCC, followed by daily intraperitoneal injections of PBS, the compounds of Formula II+III, II+IV and III+IV (in 100 μl PBS, groups A, B, C and D, respectively) for 25 days. Animals are followed for serum α-fetoprotein (AFP) and for intrahepatic and intrasplenic lymphocyte subpopulations.

Example 9

Examination of the Neuroprotective Effect of Synthetic Derivatives of β-Glycolipids and Combinations Thereof Against Aβ Peptide (Model of AD) in PC12 Neuronal Cell Cultures In order to establish a reliable cell culture system for screening the neuroprotective effect of different potential synthetic derivatives of β-glycolipids, and particularly of the compounds of Formula II, III and IV, the neurotoxic effect of Aβ (25-35), cholesterol and serum-free conditions is first examined in PC-12 cell model.

PC-12 cell culture is a rat pheochromocytoma cell line, which displays phenotypic characteristics of sympathetic neurons. In the past decade, different cellular and molecular experiments have shown that PC-12 cells are an excellent in vitro model for investigating various neurological disorders, such as Alzheimer's disease and Parkinson's disease.

PC-12 cells die in a dose dependent manner in response to exposure to the AD-related Aβ peptide. These cells also suffer from the neurotoxic effects when coming in contact with high cholesterol levels, or under serum-deprivation conditions. On the other hand, these cells benefit from the neuroprotective effect of statins, vitamin E and vitamin C after exposure to the neurotoxic effect of Aβ peptide.

PC-12 cell culture is therefore, a convenient model to test neurotoxicity and to detect neuroprotective drugs capable of overcoming the effects of such toxic conditions. The neuroprotective effect of different tested compounds on neuronal cells cultured in the presence of Aβ peptide neurotoxic is reflected by the increment of the neuronal cell survival.

The capability of the PC-12 cells to exhibit neurotoxic as well as neuroprotective effects makes these cells an authentic model for studying and screening for new neuroprotective drugs.

The inventors are thus demonstrating the neuroprotective effect of administration of synthetic derivatives of β-glycolipids such as the compounds of Formula II, III and IV and of different combinations thereof, against the neurotoxic condition induced by the AD related Aβ peptide in PC-12 neuronal cell culture. The efficacy of treatment with the compounds of Formula II, III and IV is estimated by assessing the percentage of PC-12 cell survival after being exposed to the Aβ (25-35) peptide toxic conditions.

Therefore, PC-12 cells are treated with different concentrations of the compounds of Formula I, II and III ranging between about 0.01 to 1000 microgram per ml.

Cell survival (%) is calculated relative to control cells not exposed to the Aβ peptide or to different synthetic compounds of the invention.

Example 10

Examination of the Neuroprotective Effect of Different Synthetic Derivatives of β-Glycolipids and Combinations Thereof Against 3-NP (Model of HD), MPTP and 6-OHDA (Models of PD), and Glutamate (Model of ALS) in PC12 Neuronal Cell Cultures The neuroprotective effect of synthetic derivatives of β-glycolipids in neuronal-cell model encourages their use in the prevention and treatment of AD, and possibly other neurodegenerative disorders.

In order to assess the potential neuroprotective effect of the compounds of Formula II, III and IV on other neurodegenerative disorders, the rescue of PC-12 cells treated with different neurotoxins (presenting different neurodegenerative disorders) is next tested by the inventors.

For examining the applicability of different synthetic derivatives of β-glycolipids for the treatment of PD, PC12 cells exposed to 6-hydroxydopamine (6OHDA) or to 1-methyl-4-phenyl-1,2,3,6-tetrahydropyridine (MPTP), as neurotoxins, are treated with different concentrations of the compounds of Formula II, III and IV ranging between 0.01 to 1000 microgram per ml.

Treatment of PC12 cells exposed to 3-nitropropionic acid (3-NP) as a neurotoxin, with different concentrations of the compounds of Formula II, III and IV ranging between about 0.01 to 1000 microgram per ml, reflects the feasibility of treating HD with synthetic derivatives of β-glycolipids.

For evaluating the potential neuroprotective effect of synthetic derivatives of β-glycolipids on the ALS model, PC12 cells exposed to glutamate as a neurotoxin, are treated with different concentrations of the compounds of Formula II, III and IV ranging between about 0.01 to 1000 microgram per ml, cell survival is then calculated.

Example 11

β-Glycolipids Effect on AD Symptoms Using a AD-Animal Model

In order to examine the feasibility of using different synthetic derivatives of β-glycolipids for the treatment of AD, an in vivo animal model is used. Transgenic mice model expressing a mutation in the amyloid precursor protein (APP) and in the presenilin1 gene is used as AD model by the inventors. Mice are treated with different concentrations of the compounds of Formula II, III and IV in different modes of delivery such as, drinking water, gavage, and i.p. injection. The treated animals are then evaluated for improvement in clinical parameters.

Example 12

The Effect of Different Synthetic Derivatives of β-Glycolipids on PD Symptoms Using a PD-Animal Model The inventors next evaluate the neuroprotective effect of administration of different synthetic derivatives of β-glycolipids such as the compounds of Formula II, III and IV and of different combinations thereof on Parkinson's disease using an animal model. Rats stereotaxically injected with 6OHDA into the right substantia nigra develop PD-related motor deficits starting 3 days following injection. Rats are treated with different concentrations of the compounds of Formula II, III and IV in different modes of delivery such as drinking water, gavage, and i.p. injection. The treated animals are then evaluated for improvement in the motor deficits using the stepping and placing tests.

Example 13

The Effect of Different Synthetic Derivatives of β-Glycolipids on ALS Onset and Death in an ALS-Animal Model The neuroprotective effect of different synthetic derivatives of β-glycolipids on AD and PD encouraged the inventors to evaluate the feasibility of using these drugs for the treatment of another neurodegenerative disease, ALS. Therefore, ALS tg mice (starting at 8 weeks of age) are treated with synthetic derivatives of β-glycolipids such as the compounds of Formula II, III and IV and of different combinations thereof. The effect is evaluated by measuring performance in the rotarod as described in Experimental procedures, by evaluating disease development using clinical score and by examining the survival of the animals.

Example 14

Effect of Different Synthetic Derivatives of β-Glycolipids on Acute Experimental Autoimmune Encephalomyelitis (EAE)

The significant immunomodulatory effect of different synthetic derivatives of β-glycolipids and their potential neuroprotective effect in cell culture and animal models is further explored by the inventors for investigating their potential neuroprotective effect in animal models for diseases of the central nervous system (CNS). Therefore, the inventors examine the effect of the compounds of Formula II, III and IV on experimental autoimmune encephalomyelitis (EAE), an autoimmune inflammatory disease resulting in demyelination of the white matter in the CNS. In many of its clinical and histopathological aspects, EAE resembles human multiple sclerosis (MS) and acute disseminating encephalomyelitis. EAE can be induced in genetically susceptible animals by a single s.c. injection of myelin associated antigens, such as myelin oligodendrocyte glycoprotein (MOG), or proteolipid protein (PLP), emulsified in CFA and followed by a booster with *Bordetella pertussis*. A characteristic monophasic paralytic disease develops 10-13 days later. EAE serves as a useful experimental model for investigating new therapeutic strategies in MS. Various immunosuppressive agents are found effective in prevention and treatment of EAE, including corticosteroids and copolymer 1. However, patients are so far treated either symptomatically or with immunosuppressive agents, and no satisfactory therapy for MS has as yet been established.

Two mouse models are used for analyzing the potential effect of different synthetic derivatives of β-glycolipids for the treatment of EAE, C57Bl mice immunized with MOG (myelin oligodendrocyte glycoprotein), and SJL mice immunized with PLP (proteolipid protein) are treated with different concentrations of the compounds of Formula II, III and IV and of different combinations thereof.

While this invention has been described in terms of some specific examples, many modifications and variations are possible. It is therefore understood that within the scope of the appended claims, the invention may be realized otherwise than as specifically described.

The invention claimed is:

1. A method of treating, ameliorating or delaying the onset of a pathologic condition in a mammalian subject in need thereof, the method comprising administering to said subject a therapeutically effective amount of:

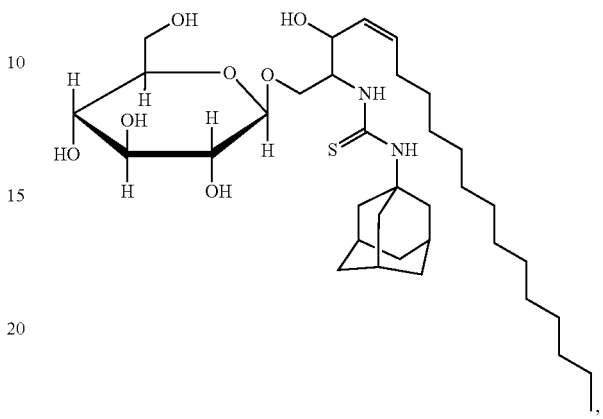

wherein the pathologic condition is metabolic syndrome, insulin resistance, type II diabetes, immune-mediated hepatitis, immune-mediated colitis, hepatocellular carcinoma, melanoma, non-alcoholic fatty liver disease, non-alcoholic steatohepatitis, HCV infection or HBV infection.

2. The method according to claim 1, wherein said method comprises administering a mixture of the compound and a second β-glycolipid, wherein the compound and said second β-glycolipid derivative are at a mass ratio between 1:1 to 1:1000.

3. The method according to claim 1, wherein said administering step comprises oral, intraperitoneal, intravenous, intramuscular, subcutaneous, parenteral, transdermal, intravaginal, intranasal, mucosal, sublingual, topical, rectal, or subcutaneous administration, or any combination thereof.

4. The method according to claim 1, wherein said method leads to activation of JNK2 pathway and thereby modulation of at least one of adipose or stromal tissue derived T regulatory cells.

5. The method of claim 1, wherein the pathologic condition is immune-mediated hepatitis.

6. The method of claim 1, wherein the pathologic condition is metabolic syndrome.

7. The method of claim 1, wherein the pathologic condition is insulin resistance.

8. The method of claim 1, wherein the pathologic condition is immune-mediated colitis.

9. The method of claim 1, wherein the pathologic condition is type II diabetes.

10. The method of claim 1, wherein the pathologic condition is non-alcoholic fatty liver disease.

11. The method of claim 1, wherein the pathologic condition is hepatocellular carcinoma.

12. The method according to claim 1, wherein said method leads to at least one of a decrease in the serum levels of triglycerides, alanine aminotransferase, aspartyl transaminase or glucose or to reduction of insulin resistance.

13. The method according to claim 12 or 4, wherein said pathologic condition is metabolic syndrome, non-alcoholic fatty liver disease or non-alcoholic steatohepatitis.

14. The method according to claim 1, wherein said method, when compared to an untreated subject with the pathologic condition, leads to a decrease in the serum level of at least one of IFN-γ, IL-6 or TNF-α and an increase in the serum level of at least one of IL-10 or IL-4, in a treated subject suffering from the pathologic condition.

15. The method according to claim 1, wherein said method suppresses type I NK T cells and STAT4 expression.

\* \* \* \* \*